(12) United States Patent
Petrukhin et al.

(10) Patent No.: US 7,005,290 B1
(45) Date of Patent: Feb. 28, 2006

(54) BEST'S MACULAR DYSTROPHY GENE

(75) Inventors: Konstantin Petrukhin, Collegeville, PA (US); C. Thomas Caskey, Lansdale, PA (US); Michael Metzker, Fort Washington, PA (US); Claes Wadelius, Upsala (SE)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/622,964

(22) PCT Filed: Feb. 22, 1999

(86) PCT No.: PCT/US99/03790

§ 371 (c)(1),
(2), (4) Date: Dec. 12, 2000

(87) PCT Pub. No.: WO99/43695

PCT Pub. Date: Sep. 2, 1999

Related U.S. Application Data

(60) Provisional application No. 60/075,941, filed on Feb. 25, 1998, provisional application No. 60/122,926, filed on Dec. 25, 1998.

(51) Int. Cl.
C07H 21/04 (2006.01)
C12N 15/63 (2006.01)
C12N 1/21 (2006.01)

(52) U.S. Cl. ............... 435/252.3; 536/23.1; 536/23.5; 530/300; 435/6; 435/91.2; 435/325; 435/320.1; 930/10

(58) Field of Classification Search ............... 536/23.1, 536/23.5; 530/300; 435/6, 91.2, 252.3, 435/325, 320.1; 930/10
See application file for complete search history.

(56) References Cited

OTHER PUBLICATIONS

Molecular and Cellular Biology Products Catalog, Pharmacia Biotech, 1994m pp. 81.*
Boehringer Mannheim Biochemicals Catalog. 1997, pp. 95.*
Petrukhin et al. Identification of the gene responsible for Best macular dystrophy. Nature Genetics 1998, vol. 19, pp. 241-247.*
Marquardt et al. Mutations on a novel gene, VMD2, encoding a protein of unknown properties cause juvenile-onset vitelliform macular dystrophy (Best's Disease). Hum. Mol. Gen. (Sep. 1998) vol. 7, No. 9, pp. 1517-1525.*
Adams et al. Initial assessment of human gene diversity and expression patterns based upon 83 million nucleotides of cDNA-sequence. 1995, Nature, vol. 377 (6547 Suppl) pp. 3-174.*
Adams et al. 1997, EST 19416, Institute for Genomic Research, Acc. No. AA317489, Accessed 8-5-03.*
Baribault, et al., 1989, Mol. Biol. Med., 6:481-492.
Capecchi, 1989, Science, 244:1288-1292.
Capecchi, 1989, Trends in Genet., 5:70-76.
Cunningham & Wells, 1989, Science, 244:1081-1085.
Forsman et al., 1992, Clin. Genet. 42:156-159.
Frohman et al., 1989, Cell, 56:145-147.
Hentze et al., 1986, Proc. Nat. Acad. Sci. 83:7226-7230.
Hopp & Woods, 1981, Proc. Natl. Acad. Sci. USA, 78:3824-3828.
Hou et al., 1996, Human Heredity, 46:211-220.
Jameson & Wolf, 1988, CABIOS (Computer Applications in the Biosciences), 4:181-186.
Kim, et al., 1988, Nucleic Acids Res. 16:8887-8903.
Kim, et al, 1991, Gene, 103:227-233.
Kohler & Milstein, 1975, Nature, 256:495-497.
Lin et al., 1985, Proc. Natl. Acad. Sci. USA, 82:1391-1395.
Mansour et al., 1988, Nature, 336:348-352.
Michael et al., PCR Protocols: A Guide to Methods and Applications, eds., 1990, AcademicPress.
Sedivy et al., 1989, Proc. Natl. Acad. Sci. USA, 86:227-231.
Smithies et al., 1985, Nature 317:230-234.
Sullivan & Daiger, 1996, Mol. Med. Today, 2:380-386.
Thomas et al., 1986, Cell, 44:419-428.
Thomas et al., 1987, Cell, 51:503-512.
Watson et al., Molecular Biology of the Gene. 1987, Fourth Ed., The Benjamin/Cummings Publishing Co., Inc., p. 226.

* cited by examiner

Primary Examiner—Nashaat T. Nashed
Assistant Examiner—Holly Schnizer
(74) Attorney, Agent, or Firm—Vineet Kohli; Joanne M. Giesser

(57) ABSTRACT

Novel human and mouse DNA sequences that encode the gene CG1CE, which, when mutated, is responsible for Best's macular dystrophy, are provided. Provided are genomic CG1CE DNA as well as cDNA that encodes the CG1CE protein. Also provided is CG1CE protein encoded by the novel DNA sequences. Methods of expressing CG1CE protein in recombinant systems are provided. Also provided are diagnostic methods that detect patients having mutant CG1CE genes.

5 Claims, 18 Drawing Sheets

```
   1 ccaaaaaatt gttctcttgg gggttggggc gacaagcggg aagggagggc
  51 attttgggca aattggctta ttgccacgca agggctttaa caccttaggt
 101 tggtgggttc acaggttgca ggcaacccac catggcacac gtatacctat
 151 gtaaccaacc tgcaccatca tgtataccta tgtaaccaac ctggtacatt
 201 ctgcacacgt atcccaggac tttagagtga aaaaaaaagt ggtgtgtaga
 251 aaaatcacct gcaatctcag catagttaac gcttagtaca tttcagagag
 301 agagggtgac aggaagggga ggatgagagt gggtttaaga cacaaggtca
 351 tattataaaa tcagggcttc tggaagttta gtcccaaaac cacacatctc
 401 ataatcccct gcagtgcttg attaaaatgc aacatcacta aggccacaga
 451 ctcagactct ggagaaagat ccagaaaact gcccgtttaa taaacatttg
 501 ggcgattctt acggcctcta aagaccaaga accactgctg cctagagctc
 551 tgctctcttc attgaacaat acaagaggag tgtgtaggta gacacccacc
 601 acttccaaca gcttaggaga gcccttgagt atggattgat gtattaaaat
 651 ttattgaatc acatgctgag attttcacca gctgcccgtg gggatctggg
 701 catttattcc catattgcac tggctggctg gaagccagca gcataaactc
 751 cagggctgtt ctgtcaaccc ccaccagact caccccccctc caccagcccc
 801 ggcaggcttc tccttccatc tctctgaagc aacttactga tgggccctgc
 851 cagccaatca cagccagaat aacgtatgat gtcaccagca gccaatcaga
 901 gctcctcgtc agcatatgca gaattctgtc attttactag ggtgatgaaa
 951 ttcccaagca acaccatcct tttcagataa gggcactgag gctgagagag
1001 gagctgaaac ctacccgggg tcaccacaca caggtggoaa ggctgggacc
1051 agaaaccagg actgttgact gcagcccggt attcattctt tccatagccc
1101 acagggctgt caaagacccc agggcctagt cagaggctcc tccttcctgg
1151 agagttcctg gcacagaagt tgaagctcag cacagccccc taaccccccaa
1201 ctctctctgc aaggcctcag gggtcagaac actggtggag cagatcattt
1251 agcctctgga ttttagggcc atggtagagg gggtgttgcc ctaaattcca
1301 gccctggtct cagcccaaca ccctccaaga agaaattaga ggggccatgg
1351 ccaggctgtg ctagccgttg cttatgagca gattacaaga agggactaag
1401 acaaggactc ctttgtggag gtcctggctt agggagtcaa gtgacggcgg
1451 ctcagcactc acgtgggcag tgccagcctc taagagtggg caggggcact
1501 ggccacagag tccCAGGGAG TCCCACCAGC CTAGTCGCCA GACCTTCTGT
1551 GGGATCATCG GACCCACCTg gaaccccacc tgtgagtaca aggtgcccca
1601 ggtggactgg gatggggctt tgaggccttc agggttggat ggccatcttg
1651 cgtatttgtg tgggatatgc acacacaggc agcacatgcg caggtgtgtg
1701 ggcacctgtg tgtctgtgca aatgccctga ggtgggaatg agcttggtgt
1751 gcatcaggag cgacagccag ccagtgtggc tgcagcaaaa cacacaggga
1801 aagaatggag ggggcatcaa tcactgacaa aattatttat agagctcccc
1851 ctaaaaaaaa gaaggtctct tctttcgata gaagaaggga gagaggggt
1901 ttgtccttat aaatataagg gaggagccgc cctcaaaaa ataagggagg
1951 gaggacceaa gaccccgtgg gttgtgtgtt ttccaggggg agctcgaacc
2001 ctttagaggg agcgtgggag aaccgctgta ttcaggcctc tcgagagaaa
2051 aggagcggcc gcccaaaaaa tatccctccc gggcgataag aaatggtggc
2101 ctctctcaaa aagatgaaga ggaagccgga gttgtatgtg ttgatatttt
2151 taaaactcca ggtagnnnnn nnnnntgctt cagtaaattt ttattgagcg
2201 ccttctacga gaacacaaga ggagcttcca ttctgaggag gaaacaggca
2251 ggaaacaggc agatatcctg tataatttca agtagtgata agtgctctct
2301 agaaatatca agcaaggtga ggagacacag agcaccggtg gcagtggggc
2351 tctatttcca ggttggatgg ttgggaacat ccttttctaaa gggaacctgg
2401 agtgggaagg aaccatgcag gtatctcagg aagagcttcc tccaggcagg
2451 aagatcagca ggtggaaagg ccctggagcc accattcagt aaacatcatt
2501 tgagcatctc taccagctag gttccattat gggaatggga atatggtggt
2551 ggacagggct gcctggtccc ttccatactt ctcacactag ggtggttgag
2601 agagcttggg agctaacgaa caagatgggc tgagaacact gcctagccca
2651 gaggacctga gcttagtgtg tagacattgc tgctgttact gcctttgtcg
2701 ttgtattatt tatttattta tttattgatc ttaagacaga gttttgctct
```

FIG.1A

```
2751 tcttacccag gcttgagtgc aatggcgtga tctcagctca ctgcaacctc
2801 cacctcctgg gatcaagcga ttctcctgcc tcagcctcct gagtagctgg
2851 gattacaggc acccgcacca cgcctggata ttttttttgt attttttagta
2901 gagacagggt ttcaccatgt tggacaggct ggtctcgaac tcctgacctt
2951 aggtgatcca cctgcctcga cttcccaaag tgatgggatt ataggcatga
3001 gccactgcgc ccagtgatta tagaaagtta aaggcacatg gcaatgcaca
3051 cgcctatcta cgtcttccct gccaaagcaa agggcagcct ctgggctcac
3101 tttcttgcgt ttctacttcc aaaaggcagt cagaactggc agggccttgg
3151 agaccacttc atccacctcc tagggtccct atgggagagt tgaggtccag
3201 agcagggaag ggtcctgaca ggctctgacc agggcctctg atccctacaa
3251 accccccaatc ggtgtccctc tctaccagGA CCCAAGCCCA CCTGCTGCAG
3301 CCCACTGCCT GGCCATGACC ATCACTTACA CAAGCCAAGT GGCTAATGCC
3351 CGCTTAGGCT CCTTCTCCCG CCTGCTGCTG TGCTGGCGGG GCAGCATCTA
3401 CAAGCTGCTA TATGGCGAGT TCCTAATCTT CCTGCTCTGC TACTACATCA
3451 TCCGCTTTAT TTATAGgtaa agctggcagg gctgggccgg gggcctggg
3501 aaggatgtgg ctggggctgg gagctgggag ctcctggggg cctcccagcc
3551 agctcagggc ccagtgcacc agtccactac aacactaagc tgggctcctg
3601 accagctcct gggcactgga gctgaggctg cgcgctgggg gctgggcaga
3651 gtaaagaagt cacactgaga ggatgctcaa gccaggccag cagggtttta
3701 gccacccttc ctccaacccc aggaggaccc ctggagccca ggctttgtct
3751 ggccccactc tactggcctg ttttactgaa tcccacacag actcataggc
3801 ccacatagta cattaaaaaa gagagagaga gagagagaga gagagagatg
3851 gagtctcact gtgttgtcca ggctggtctc gaactcctag gctcaagcaa
3901 tcccctgcc ttagcctccc aaggggctgg gattacaggt gtgagctact
3951 gcacttgacc aaccacatgg tactttttt ttttttttt tttttgaga
4001 cagggtttca ctccatcacc caggctggag tgcagtgggg gcaatcttgg
4051 ctcactgtaa cctctgcctc ccaggtgcaa gcgattctcc tgccttagcc
4101 tcctgagtag ctggaattat aggcacacac caccacgcct ggctaatttt
4151 ttttttttttc tgtatttta gtagagacag ggtttcatca tgttggacag
4201 gctggtcttg aaccctgac ctcaagtgat ccacccacct cggcctccca
4251 aagtgctggg attacaggtg tcagccacca tgcacagccc acatggtaca
4301 tttttaaaa ttattttta attaaantgt ttatctaagg ccagtagcag
4351 tgactcgcgt ctgtaatccc agcactttga ggggccaagg tgcggggatc
4401 acttgagcct gggagttcag cgtgggcaac atagtgagac cccgtctcta
4451 ccaaaaattt aaaaaattag ctgggagtgg tggcatttgc ctgtggtccc
4501 agctacttgg gaagctgagg tgtggggatg gctgaagcct gtgaggtcga
4551 ggctgcagtg agctatgatc acaccactgc acttcagcct gagtgacagg
4601 ctatctcaaa agcaaacaaa ataatgttta tctaaacggt aaggtataat
4651 cacagaatat atgatagcat tttaaattga aaaagcatta atgattacat
4701 ggattgtaaa atatcaaata catgaaattc ttgtgttctt aataatgcta
4751 gcaacaaggc acatttggtt tttactaggg caccaaggta ctttaaaaaa
4801 agttagggcc agccacaggg gctcacacct gtaatcccag cactttggga
4851 ggccaaggca ggaggatcac ttgagcccag gagtttagga cctgagcaac
4901 atagggagat cctgatcttg tctctataaa aaattaaaaa attggctagg
4951 cccctttggct tacacccgta atcccagcac tttgggaggc cgaggcgggt
5001 ggatcatgag gtcaggagtt caagaccagc ctggccaaca tagtgaaccc
5051 aatctctact ataaatacaa aaattagccg agtggggtgg cacgcacctg
5101 tagttccagc tactcaggag gatgaggccg gagaatcgct tgagcccggg
5151 aggcagaggc tgcagtgagc cgagaccatg ccattgcact ccagcctagg
5201 tgacagagtg agactccgtc ttaaaataat attaaaatct aaaatgatc
5251 tgggcatggt ggcttatgcc tgtagtccca cccagctctt caggaggctg
5301 aagcggggagg attgcttcag cccaggaggt tgaggctgca gtgagtcatg
5351 actgtgccgc tgcccttgag cctgggtaac agagcaagac cctatctcaa
5401 aacaaacaaa caaacaaaca aacaaacaaa aaccaataaa ccaaaaacat
5451 ttatctaaac aataaaataa aggacagata taatcaccga atatatgata
```

FIG.1B

```
5501 gcattttaaa ttgaaaaagc actaatgact acaatggatt ataaaacatc
5551 aaatacataa aattcttaag ttcctcctaa taccaaatac aaagcacatt
5601 ggtctttggt ttttacttgg gcaccaatgc atgctgaaaa agagtcgttc
5651 attttttaga gtagttttag gttcacagca aaattgagca gaaggtagag
5701 ttctcatgtg tctctttgct cctcaccctg cccccagcct ccccactatc
5751 aacaccccca cactacagtg gtagatttat tacaatccct gaacccacag
5801 tgacacatca ctatcaccca aagttcatag cgtacagcag ggttcactct
5851 tgggcagtac attccatggg tttggataaa tgtgtaatga tgtctccacc
5901 atcacagcat caggcagagt agtttcactg ctctaacaaa atcctctgcc
5951 tattcacccc tctcattaaa gccaaacact ctgtttcctt tttctctttt
6001 agagacagtg tctcgctctg tcaaccaggc tgaagtgcaa tggcaatcac
6051 agcccattgc agcctccaac tcctgggctc aagtgatcct cctatctcag
6101 cctccagtgg ctacgactgc aggcatacgg caacggcacc caactaattt
6151 tttgtagaga tagggtcttg ctatgttgac caggatggtc ttgaactctt
6201 ggtcctgcct tagcctccca gagctctggg attacaggcg tgaaccaccg
6251 tgcccgtccc aaacactctg tttcgacctg cttttaaaca actgaccctt
6301 ggatgcattc aaaggatcag ggtgtctgaa actggcctct gcagcaggac
6351 cttccttcct acacatctcc cagtggccag tgtgaggatt ctccccacaa
6401 gaaaccactg gagggggcct cctcctgtcc gggtttgggg ctgtacaagg
6451 agcatcatgg acctggctca ggcctcagga ggggccctgg gctggggaaa
6501 atgtgggata gcatcgaggc agtcccactc ctacccaggg ccgggctaga
6551 cctggggaca gtctcagcca tctcctcgct gcgtccacac aattccaccc
6601 ccacccccac ccccagGCTG GCCCTCACGG AAGAACAACA GCTGATGTTT
6651 GAGAAACTGA CTCTGTATTG CGACAGCTAC ATCAGCTCA TCCCCATTTC
6701 CTTCGTGCTG Ggtgagttcc cccttctggc tgttccgggt ccctgtggcc
6751 gcccaggctc cagacaggcc aggggaggat cacgaggagc tgcggcaagg
6801 ggctggggag ggggcggggg aacgccagcg gcaggtcggc gcctctctgt
6851 agggaaaggt gcggactgca gccagagaaa ctgaagttag acgttaggta
6901 agacgtcctg ccgttagcaa tgaaaacccc attttctgag ggaagcgctg
6951 acatcatggt ccctggagcc cctgcgcggg aggggagggg gtctggcgga
7001 tttctgggac cagcaggggg accccgggt gacagaaccc ttggggctct
7051 cgcgcctcca tgagaggctc tgcctgcctc tcgctcccga gcgccttcca
7101 ggagggctgg gggctaggcc cgctcgcagc agaaagctgg aggagccgag
7151 gcatcgccgg gcgctgggcc ctgggctctg gccgcagact ggcccctcgc
7201 ccctcgcccc ccgcccctcc tgcccagGCT TCTACGTGAC GCTGGTCGTG
7251 ACCCGCTGGT GGAACCAGTA CGAGAACCTG CCGTGGCCCG ACCGCCTCAT
7301 GAGCCTGGTG TCGGGCTTCG TCGAAGGCAA GGACGAGCAA GGCCGGCTGC
7351 TGCGGCGCAC GCTCATCCGC TACGCCAACC TGGGCAACGT GCTCATCCTG
7401 CGCAGCGTCA GCACCGCAGT CTACAAGCGC TTCCCCAGCG CCCAGCACCT
7451 GGTGCAAGCA Ggtgggcgga ccgggagcaa cggggaggca ccgggcagag
7501 ccaggggccg agatgggcgc ggcaggaacg gaagatgggt ggagccaaag
7551 tcacccggac tcggggact gggtggagcc aggagtgggg tgtggtcaag
7601 atttggggt ccaattgggc gggacagagt cgggtgtctg aaggtggggc
7651 gaggccagga gcccaccctc cgagagtagg agtctgaggc agggataagg
7701 acccttgagg gataatggaa agaagggtga cggcttggga actggtgagg
7751 tactagggtc tacttccctc tgcccttgcc cctcttgatc tccggtttcc
7801 actctggagg tatgggacat tggtctctga caccccctca gcctggcctg
7851 acctggtcct ggttaataag acagacccag gctaggcgtg gtggctctcg
7901 cctgtaatcc cagtgcttta ggaggcaaag gtgggaagat cgcttgagcc
7951 cagctgtttg agacgcacct gagcaacata gcgagacccc catctctaca
8001 aaaacattaa aaattagcag ggcatggtgg cgtgtgcctg tagtctgagg
8051 ctgagtatcg ggaggctgag gcaggaggat cacttgagcc cagcagttcc
8101 aggctgcagt gcgctaagat cgcaccgctg cactccaacc tcggtgacag
8151 agccagaccc tttctctgga aataaataaa taccctgccc acatgctcag
8201 cacagaacag cacctagtag gtgctcagaa attttttttgt tgttgaaaga
```

FIG.1C

```
 8251 aagaggatgg caaaggagtg ctgaggttcc tataggtcag caggtgccgg
 8301 ccatcccttc tgcaggttct cccacccacc gccttcttca ctccactctg
 8351 cagGCTTTAT GACTCCGGCA GAACACAAGC AGTTGGAGAA ACTGAGCCTA
 8401 CCACACAACA TGTTCTGGGT GCCCTGGGTG TGGTTTGCCA ACCTGTCAAT
 8451 GAAGGCGTGG CTTGGAGGTC GAATCCGGGA CCCTATCCTG CTCCAGAGCC
 8501 TGCTGAACgt gagcccactg tacagacagg gctgccgcag agtgggaagg
 8551 gttgtggtcc acaggaaaca aggtttccta caaagagaag ccttgggccc
 8601 ctgagggtct tccgagagcc ggaggtgggg ttgcagaatc ttttccaaca
 8651 gcaatccaca gaccgaggtg gtcccttatc agaggcccct ccctcttctc
 8701 caagtctgtg aggtcctggt tccctttga tagatgagga agctgagaca
 8751 caaagaggtt tagtgagctt cccatggcca cacagccagg aatggaccat
 8801 aggtaccagg ccctggtacc tggagaagag gtggggcga gcccagggtg
 8851 gggcaggtg gtgttcagaa ccccatcccc ctcttctgcc cccagGAGA
 8901 TGAACACCTT GCGTACTCAG TGTGGACACC TGTATGCCTA CGACTGGATT
 8951 AGTATCCCAC TGGTGTATAC ACAGgtgagg actaggctgg tgaggctgcc
 9001 cttttgggaa actgaggcta gaaggaccaa ggaagcagct gggtggggaa
 9051 gggctcacct agaggctaag tggctcccct gggagttggg tccacacttt
 9101 gaagttgggt ctggactttg aagtgccaag ttctaagagt ccaggctcct
 9151 gcctggccca gtccagtaga ggcaatgtga ttatcccat attaaagaga
 9201 ggttggcagg gcacagtggc tcatgcatgt aatcccagca ctttgggaag
 9251 ctgaggcagg tggatcacct gaggtcagga gttcgagacc agcctggcca
 9301 acatggtgaa accccatctc tactgaaaat acagaattag ctgtgtggtg
 9351 gtgcacgcct gtaatcacag ctacttggga ggctgaggca ggagaatagc
 9401 ttgaacccgg gaggtggagg ttgcagtgag ctgagatcat gccactgcac
 9451 tccagcctgg gcgacacagc aagactctgt ctcaaacaaa caaacaaaca
 9501 aacaaacaaa caaacaaaca aagggttaa cagagcccct aagtcacata
 9551 agtgtgcaag tcagaacaag gccttggtct cctgtctcag actcccagcc
 9601 cctggagcat cctgatttca gggttcccac ctagcccttt gctaccacat
 9651 cctcctcctc ctcctcctcc tcccagGTGG TGACTGTGGC GGTGTACAGC
 9701 TTCTTCCTGA CTTGTCTAGT TGGGCGGCAG TTTCTGAACC CAGCCAAGGC
 9751 CTACCCTGGC CATGAGCTGG ACCTCGTTGT GCCCGTCTTC ACGTTCCTGC
 9801 AGTTCTTCTT CTATGTTGGC TGGCTGAAGG TGGGCCTCTC CAGGGCCCTG
 9851 CTGGGCTGGA GGCATGGCCA GAGGGGTCAT GGCCAGCAGC TGCTTGAGAC
 9901 GAGGATGCAG TGTCAGGAAA GGAAGGTCTC ACGGGTAGAA AGCAGCCAGG
 9951 CGTGGTGGCG CACACCTGTA ATCCCAGCTA CTCGGGAGGC TGAGGCAGGA
10001 GAATCGCTTG AACCCGGGAG GCGGAGGTTG TGgtgagttg agatcgtgcc
10051 actgcactcc agcctgggca aaagaatgaa actctatctc aaaaacaaca
10101 acaacaacaa aacaaagccc taaggttcag aagcccctgc cctttagaag
10151 cagagcgaac actctcctat taagatgctg ttgggtgtct ttttcactca
10201 gtagctgtcc agtattctcc acacagcata atagacagat tctaatacaa
10251 atttcttcaa ctcttaattc ctcctttgtg ccaccatttt ttcttctacc
10301 tcctaattta tgaatgggtt agtatgctct gcttctgcat tgagacaaaa
10351 tacagagaga gagaaagatc tatcttaatc ccgccccatt ttagttggaa
10401 aaaaacttta ttaaatcagg caagtaaaat ccgccaagga ttgnnnnnnn
10451 nnnagatgtt ctgaatcaga gagttttctc tcgagctctt tatctttcct
10501 tccttatgtt gcccacccac tctctctcac ttcctacctt cctttatttt
10551 ttggtaatgg gggtgtaagt ctctgtctct gcccttcctg tcactgtgac
10601 acacacacac acacacacac acacacacac acacacacac attcatattc
10651 ctctaaattc cccctgcacc cccagttatc tttggttttct gcagatcaaa
10701 acaaatcaca cttttatgct tgaaattctc cagggtgccc cagtggcctg
10751 caagatgtcc cctggacccc taaggcagac gcgtgtcacc tcttcggggc
10801 tttgttaggg catttagag gttgctatcc aggaatctgc ccacctagac
10851 tgccctttag ttcagcccag cttcagtata tatctctgtt gcatgaatga
```

FIG. 1D

```
10901 ataaaattat gcaactccag gtaagataca tgaggtgaga taaaggcagt
10951 gactcagccg agtgatacac tcagggacag ctgtgggtgt tcagggaagg
11001 actggctcag aagagttaga ggggctgtgt ccagaagtgt gtgggtgcct
11051 acaagtgtgg ggggctggag ccctaaactc tgcctttgaa gacagtggtc
11101 aggcaggaag ggcttcatgg ggtgtggaaa tagcagcagc tgaggtttaa
11151 aggggggaagc tggctttgag gagttctgcc tgagggttta cagagcctca
11201 cctgtcccca agGTGGCAGA GCAGCTCATC AACCCCTTTG GAGAGGATGA
11251 TGATGATTTT GAGACCAACT GGATTGTCGA CAGGAATTTG CAGgtatggg
11301 gagagggaga gaaaccatac catggaccct ccccaaagtg gacccaaaga
11351 gagctcctcc ctcctgcagc cagtcattca ctcacaggat tctcacctca
11401 atctttgagg ctgcaggcag gcacccatct ccccatttca caggcaggga
11451 aactgaggtc cagagagagg gagagatCcc tccaagtcat caggcacata
11501 caaggtcctg cctgggatga tctttctgtg ggacttcttc tgtccctggt
11551 gaccagGTGT CCCTGTTGGC TGTGGATGAG ATGCACCAGG ACCTGCCTCG
11601 GATGGAGCCG GACATGTACT GGAATAAGCC CGAGCCACAG CCCCCCTACA
11651 CAGCTGCTTC CGCCCAGTTC CGTCGAGCCT CCTTTATGGG CTCCACCTTC
11701 AACATCAGgt gtggccagag ccaggggggct gggtgggaag ccctcctag
11751 tgcaggggtc tgcctaggaa cttagaatag cactagttaa tgcatacagg
11801 ttgcttcagt aagtgtcagg cactgtacta tgctctttat aaacattaac
11851 tattttttc ctcccaataa ttctggtttg ttatcccaag ttthcagata
11901 attaaagtac aggttcagag agagtaagtt gtccaaggcc acatagctac
11951 caaatggtgc atttgctact cgaaggacag cctatgatca gtgatgcagt
12001 ggaacgttag gacctggctc ttgtcatcca gaactatgtt ttcttttctt
12051 tttgagacag tatctcgctc tgtcgcccag gttggagcgc agtggcgtga
12101 tcttggctca ctgcaacctc cgcctcctgg gttcaagtga ttctcctgct
12151 tcagcctccc cagtagctgg gattacaggt gcccacaacc acaactggct
12201 aattttgta cttttagtag agatgaggtt tcaccatgtt ggccaggctg
12251 gtctccaact cctgaccagt aatctgcccg ctttggcctc ccaaaatgct
12301 ggaattatag gtgtcaaaac tatgttttct gataagctac gatgcttgga
12351 tgggaagtgg aagtggggtt ccctgggatg ggggagggggc agcaaagtcc
12401 cagcaggcag ccaggccatc acaggtacct cctgaattga ctttgtccta
12451 ccgagtaaag ggctcaggcc acccacagca gccagactta tccccacatg
12501 gtcccacttc cctgattcca tctgaatccc tcttgagctg cagtgggctg
12551 aagggctatc ccagctggtc cttctccccc aggacaacag agttgaaagt
12601 gccttggaga gtgttgggca catgtcaggg ttcatactca agggtttctt
12651 ccacggtatc cagtgctgtt ctcgcttgtt cttttctttt tttttttta
12701 aacggagttt cactcttgtt gcccagagct ggagtgcagt ggcataatct
12751 cggctcactg caacctccgc ctcccagatt caagcaattc tcctgcctca
12801 gcatcctgag tagctgggat tataggtgcc agccaccaag cccggctaat
12851 ttttgtattt ttagtagaga cagtttcacc atgttggcca ggctggtctc
12901 gaactcctga cctcaggtga tccaccctcc tcagcctccc aaagtgctgg
12951 gattacatgt gtgagccact gtgcctggct gcttgttctt ttaagaacca
13001 aatatcctac tagactgcaa tcgagtttaa ctacagtcta tagatactgt
13051 gaggaatggt tgggaaggtc atcaaatgaa ggctggaggc ttgcttaggt
13101 cagaaacatt tctggaggat gactttgagc cctacatggt ctgtacccca
13151 gcagctgaag gttgttgagg gatggggagg gctgaaaaca gaacgataaa
13201 gcatagacct tgtctccaag gaatgcacaa tttatggagg gagctcaaac
13251 ccaagtctca aactctggat acaaggtaca aagtactgga tgtccagaaa
13301 agggacagaa catggaacac agtcatattt gtctgcatgg gaggcggctt
13351 ccagctgggt ctggagctga gccatggaac atgggaagaa tctgaacttg
13401 ggcaagggca ggccatactc tctggtagat aagcttttcct tgcagggtaa
13451 aggtctgggg ctcccgggat gcctgttgct aggaagtcaa atttctcttt
13501 gtggatgtca ctcccagttg gaaccacaaa ttcctggcat tgcccagagt
13551 cactcatggg cctcatctga accactcatg ccagggcacc agtgtttctg
```

FIG.1E

```
13601 actgcctgga gtgaggggtt ttacagggga agtgaatgat gaggaggcct
13651 ttacacgcca ggaggggtgg ttgcggggt tggatgttaa ctctggtcaa
13701 gagggaatca acaaacagtg aggtgagctg ggcctggagg gatcaccggg
13751 aggtacagta cagatcagga gagaggtgag agctggggca tggtgaggaa
13801 gacggtgtgg ccttggcttg ggccaactga gagagaggag cgggggtaag
13851 ggagaagtaa ggccaggtgt tggtcctttg tccactggct cagccctgca
13901 tctcctgttt ctttccagCC TGAACAAAGA GGAGATGGAG TTCCAGCCCA
13951 ATCAGGAGGA CGAGGAGGAT GCTCACGCTG CATCATTGG CCGCTTCCTA
14001 GGCCTGCAGT CCCATGATCA CCATCCTCCC AGGGCAAACT CAAGGACCAA
14051 ACTACTGTGG CCCAAGAGGG AATCCCTTCT CCACGAGGGC CTGCCCAAAA
14101 ACCACAAGGC AGCCAAACAG AACGTTAGGG GCCAGGAAGA CAACAAGGCC
14151 TGGAAGCTTA AGGCTGTGGA CGCCTTCAAG TCTGCCCCAC TGTATCAGAG
14201 GCCAGGCTAC TACAGTGCCC CACAGACGCC CCTCAGCCCC ACTCCCATGT
14251 TCTTCCCCCT AGAACCATCA GCGCCGTCAA AGCTTCACAG TGTCACAGGC
14301 ATAGACACCA AAGACAAAAG CTTAAAGACT GTGAGTTCTG GGGCCAAGAA
14351 AAGTTTTGAA TTGCTCTCAG AGAGCGATGG GGCCTTGATG GAGCACCCAG
14401 AAGTATCTCA AGTGAGGAGG AAAACTGTGG AGTTTAACCT GACGGATATG
14451 CCAGAGATCC CCGAAAATCA CCTCAAAGAA CCTTTGGAAC AATCACCAAC
14501 CAACATACAC ACTACACTCA AAGATCACAT GGATCCTTAT TGGGCCTTGG
14551 AAAACAGgtc tgtcctccac ctgaaccagg ggcactgcat tgccctgtgc
14601 cccaccccag cttcccttgc tctgagccta cccttcctcc acaatttcct
14651 agggttccat cactgccaga gcacactgga cctacgccca gcactggctt
14701 ggggtatata cttggccacc ttcacaggga tcctagggaa gtgttcggga
14751 ccttttctca cttcaccctg gtatcacccg gaagacttct tgggaccagg
14801 tgaaggaaga tgaggttgtg ctgaccagaa tgctgctgga gaactgcccc
14851 agggctgaca ggccaggctt agctgagcag atgttatcac tggccccaac
14901 ttactttgag caagggtggc tgacccaaaa ccatgaggtg gcagtcagct
14951 ggatgacaga tgaacacttc ccccataact atttagggta gtacacaagc
15001 actacaggaa agggtggcag gaactgcctc actcctagga actggtagat
15051 ggtgaggttg agggtgtcca gcgccattag gtcattttct cactgcctgg
15101 gaacctcacc aaaatacttc ttgcttcctt ggggtcagcc caaagctgtc
15151 acaaaatcag atatttccct ttattccaga tttcctggac actgtcaccc
15201 aattataaac accccacttc agacccaatc acgtgggagg aagtgtaact
15251 tcccttttct ggattctcaa gcagttactt tcacgggtca gaacacgcag
15301 ctattatgat tgaaacctta aaagggcaac aatttcaatc ttgcttctag
15351 gctaagacag gaacttggca acatctgtg gcctgttcag caaaggatgt
15401 tcatatttaa gaatcttgtc ttgggctggg tgtggaggca agtgaatcac
15451 aggaggtcag gagtttgaga ccaacctggc caacatgatg aaacccatc
15501 tctaccaaaa aaaatacaaa tcagctggcc gtcgtggtgt gcctgtagtc
15551 ccaacgcagg aggttgaggg gagaattgct tgaacccagg aggtggtggt
15601 tgcagtgaga ttgagcaact gcaatccagc ctgggcgacg gagtgagact
15651 gtctcaaaaa aaaaaaaaa aggatcgtct caacctttgc cctcctactg
15701 caacattttg gtatttgaaa tgaaggtacc ttccatactt atgctgttaa
15751 tactttcatt ctcactagGG ATGAAGCACA TTCCTAACCT GCTTCCTAAT
15801 GGGGATGCTT CGCCAGCCAG GTCCTCACCT GTGTGTACAC CAGCAGGACA
15851 CTGATCCAGT CACAGCCATA CAGCTGTCCA CACTGAAGAA CGTGTCCTAC
15901 AACAGCCTGA ATCAAATGGT TAGCTTAATA GATAAAAATC CCAGACTACT
15951 TCAGCCTTTA ATGCCTTTTA TTCATAAAAA CTGTGAAAGC TAGACTGAAC
16001 CATTGGAAAC ATTTAACTCA GACTCTGGAT TCAGAGTCGG GAACCCTTAG
16051 TTCTATCTGA ATCCAAGACA GCCACACCTT AGTATACTGC CCAAACTAAT
16101 GAGTTTAATA AATACAAATA CTCGT (SEQ.ID.NO.:1)
```

FIG. 1F

```
CAGGGAGTCCCACCAGCCTAGTCGCCAGACCTTCTGTGGGATCATCGGAC 50
CCACCTGGAACCCCACCTGACCCAAGCCCACCTGCTGCAGCCCACTGCCT 100
GGCCATGACCATCACTTACACAAGCCAAGTGGCTAATGCCCGCTTAGGCT 150
CCTTCTCCCGCCTGCTGCTGTGCTGGCGGGGCAGCATCTACAAGCTGCTA 200
TATGGCGAGTTCTTAATCTTCCTGCTCTGCTACTACATCATCCGCTTTAT 250
TTATAGGCTGGCCCTCACGGAAGAACAACAGCTGATGTTTGAGAAACTGA 300
CTCTGTATTGCGACAGCTACATCCAGCTCATCCCCATTTCCTTCGTGCTG 350
GGCTTCTACGTGACGCTGGTCGTGACCCGCTGGTGGAACCAGTACGAGAA 400
CCTGCCGTGGCCCGACCGCCTCATGAGCCTGGTGTCGGGCTTCGTCGAAG 450
GCAAGGACGAGCAAGGCCGGCTGCTGCGGCGCACGCTCATCCGCTACGCC 500
AACCTGGGCAACGTGCTCATCCTGCGCAGCGTCAGCACCGCAGTCTACAA 550
GCGCTTCCCCAGCGCCCAGCACCTGGTGCAAGCAGGCTTTATGACTCCGG 600
CAGAACACAAGCAGTTGGAGAAACTGAGCCTACCACACAACATGTTCTGG 650
GTGCCCTGGGTGTGGTTTGCCAACCTGTCAATGAAGGCGTGGCTTGGAGG 700
TCGAATCCGGGACCCTATCCTGCTCCAGAGCCTGCTGAACGAGATGAACA 750
CCTTGCGTACTCAGTGTGGACACCTGTATGCCTACGACTGGATTAGTATC 800
CCACTGGTGTATACACAGGTGGTGACTGTGGCGGTGTACAGCTTCTTCCT 850
GACTTGTCTAGTTGGGCGGCAGTTTCTGAACCCAGCCAAGGCCTACCCTG 900
GCCATGAGCTGGACCTCGTTGTGCCCGTCTTCACGTTCCTGCAGTTCTTC 950
TTCTATGTTGGCTGGCTGAAGGTGGCAGAGCAGCTCATCAACCCCTTTGG 1000
AGAGGATGATGATGATTTTGAGACCAACTGGATTGTCGACAGGAATTTGC 1050
AGGTGTCCCTGTTGGCTGTGGATGAGATGCACCAGGACCTGCCTCGGATG 1100
GAGCCGGACATGTACTGGAATAAGCCCGAGCCACAGCCCCCCTACACAGC 1150
TGCTTCCGCCCAGTTCCGTCGAGCCTCCTTTATGGGCTCCACCTTCAACA 1200
TCAGCCTGAACAAAGAGGAGATGGAGTTCCAGCCCAATCAGGAGGACGAG 1250
GAGGATGCTCACGCTGGCATCATTGGCCGCTTCCTAGGCCTGCAGTCCCA 1300
TGATCACCATCCTCCCAGGGCAAACTCAAGGACCAAACTACTGTGGCCCA 1350
AGAGGGAATCCCTTCTCCACGAGGGCCTGCCCAAAAACCACAAGGCAGCC 1400
AAACAGAACGTTAGGGGCCAGGAAGACAACAAGGCCTGGAAGCTTAAGGC 1450
TGTGGACGCCTTCAAGTCTGGCCCACTGTATCAGAGGCCAGGCTACTACA 1500
GTGCCCCACAGACGCCCCTCAGCCCCACTCCCATGTTCTTCCCCCTAGAA 1550
CCATCAGCGCCGTCAAAGCTTCACAGTGTCACAGGCATAGACACCAAAGA 1600
CAAAAGCTTAAAGACTGTGAGTTCTGGGGCCAAGAAAAGTTTTGAATTGC 1650
TCTCAGAGAGCGATGGGGCCTTGATGGAGCACCCAGAAGTATCTCAAGTG 1700
AGGAGGAAAACTGTGGAGTTTAACCTGACGGATATGCCAGAGATCCCCGA 1750
AAATCACCTCAAAGAACCTTTGGAACAATCACCAACCAACATACACACTA 1800
CACTCAAAGATCACATGGATCCTTATTGGGCCTTGGAAAACAGGGATGAA 1850
GCACATTCCTAACCTGCTTCCTAATGGGGATGCTTCGCCAGCCAGGTCCT 1900
CACCTGTGTGTACACCAGCAGGACACTGATCCAGTCACAGCCATACAGCT 1950
GTCCACACTGAAGAACGTGTCCTACAACAGCCTGAATCAAATGGTTAGCT 2000
TAATAGATAAAAATCCCAGACTACTTCAGCCTTTAATGCCTTTTATTCAT 2050
AAAAACTGTGAAAGCTAGACTGAACCATTGGAAACATTTAACTCAGACTC 2100
TGGATTCAGAGTCGGGAACCCTTAGTTCTATCTGAATCCAAGACAGCCAC 2150
ACCTTAGTATACTGCCCAAACTAATGAGTTTAATAAATACAAATACTCGT 2200
TAAAAAAAAAAAAAAAAAAAAAAAAAAAAAA(SEQ.ID.NO.:2)
```

FIG.2

```
MTITYTSQVANARLGSFSRLLLCWRGSIYKLLYGEFLIFLLCYYIIRFIY  50
RLALTEEQQLMFEKLTLYCDSYIQLIPISFVLGFYVTLVVTRWWNQYENL 100
PWPDRLMSLVSGFVEGKDEQSRLLRRTLIRYANLGNVLILRSVSTAVYKR 150
FPSAQHLVQAGFMTPAEHKQLEKLSLPHNMFWVPWVWFANLSMKAWLGGR 200
IRDPILLQSLLNEMNTLRTQCGHLYAYDWISIPLVYTQVVTVAVYSFFLT 250
CLVGRQFLNPAKAYPGHELDLVVPVFTFLQLFLYVGWLKVAEQLINPFGE 300
DDDDFETNWIVDRNLQVSLLAVDEMHQDLPRMEPDMYWNKPEPQPPYTAA 350
SAQFRRASFMGSTFNISLNKEEMEFQPNQEDEEDAHAGIIGRFLGLQSHD 400
HHPPRANSRTKLLWPKRESLLHEGLPKNHKAAKQNVRGQEDNKAWKLKAV 450
DAFKSGPLYQRPGYYSAPQTPLSPTPMFFPLEPSAPSKLHSVTGIDTKDK 500
SLKTVSSGAKKSFELLSESDGALMEHPEVSQVRRKTVEFNLTDMPEIPEN 550
HLKEPLEQSPTNIHTTLKDHMDPYWALENRDEAHS (SEQ.ID.NO.:3)
```

FIG.3

```
CAGGGAGTCCCACCAGCCTAGTCGCCAGACCTTCTGTGGGATCATCGGAC 50
CCACCTGGAACCCCACCTGACCCAAGCCCACCTGCTGCAGCCCACTGCCT 100
GGCCATGACCATCACTTACACAAGCCAAGTGGCTAATGCCCGCTTAGGCT 150
CCTTCTCCCGCCTGCTGCTGTGCTGGCGGGGCAGCATCTACAAGCTGCTA 200
TATGGCGAGTTCTTAATCTTCCTGCTCTGCTACTACATCATCCGCTTTAT 250
TTATAGGCTGGCCCTCACGGAAGAACAACAGCTGATGTTTGAGAAACTGA 300
CTCTGTATTGCGACAGCTACATCCAGCTCATCCCCATTTCCTTCGTGCTG 350
GGCTTCTACGTGACGCTGGTCGTGACCCGCTGGTGGAACCAGTACGAGAA 400
CCTGCCGTGGCCCGACCGCCTCATGAGCCTGGTGTCGGGCTTCGTCGAAG 450
GCAAGGACGAGCAAGGCCGGCTGCTGCGGCGCACGCTCATCCGCTACGCC 500
AACCTGGGCAACGTGCTCATCCTGCGCAGCGTCAGCACCGCAGTCTACAA 550
GCGCTTCCCCAGCGCCCAGCACCTGGTGCAAGCAGGCTTTATGACTCCGG 600
CAGAACACAAGCAGTTGGAGAAACTGAGCCTACCACACAACATGTTCTGG 650
GTGCCCTGGGTGTGGTTTGCCAACCTGTCAATGAAGGCGTGGCTTGGAGG 700
TCGAATCCGGGACCCTATCCTGCTCCAGAGCCTGCTGAACGAGATGAACA 750
CCTTGCGTACTCAGTGTGGACACCTGTATGCCTACGACTGGATTAGTATC 800
CCACTGGTGTATACACAGGTGGTGACTGTGGCGGTGTACAGCTTCTTCCT 850
GACTTGTCTAGTTGGGCGGCAGTTTCTGAACCCAGCCAAGGCCTACCCTG 900
GCCATGAGCTGGACCTCGTTGTGCCCGTCTTCACGTTCCTGCAGTTCTTC 950
TTCTATGTTGGCTGGCTGAAGGTGGGCCTCTCCAGGGCCCTGCTGGGCTG 1000
GAGGCATGGCCAGAGGGGTCATGGCCAGCAGCTGCTTGAGACGAGGATGC 1050
AGTGTCAGGAAAGGAAGGTCTCACGGGTAGAAAGCAGCCAGGCGTGGTGG 1100
CGCACACCTGTAATCCCAGCTACTCGGGAGGCTGAGGCAGGAGAATCGCT 1150
TGAACCCGGGAGGCGGAGGTTGTGGTGGCAGAGCAGCTCATCAACCCCTT 1200
TGGAGAGGATGATGATGATTTTGAGACCAACTGGATTGTCGACAGGAATT 1250
TGCAGGTGTCCCTGTTGGCTGTGGATGAGATGCACCAGGACCTGCCTCGG 1300
ATGGAGCCGGACATGTACTGGAATAAGCCCGAGCCACAGCCCCCCTACAC 1350
AGCTGCTTCCGCCCAGTTCCGTCGAGCCTCCTTTATGGGCTCCACCTTCA 1400
ACATCAGCCTGAACAAAGAGGAGATGGAGTTCCAGCCCAATCAGGAGGAC 1450
GAGGAGGATGCTCACGCTGGCATCATTGGCCGCTTCCTAGGCCTGCAGTC 1500
CCATGATCACCATCCTCCCAGGGCAAACTCAAGGACCAAACTACTGTGGC 1550
CCAAGAGGGAATCCCTTCTCCACGAGGGCCTGCCCAAAAACCACAAGGCA 1600
GCCAAACAGAACGTTAGGGGCCAGGAAGACAACAAGGCCTGGAAGCTTAA 1650
GGCTGTGGACGCCTTCAAGTCTGGCCCACTGTATCAGAGGCCAGGCTACT 1700
ACAGTGCCCCACAGACGCCCCTCAGCCCCACTCCCATGTTCTTCCCCCTA 1750
GAACCATCAGCGCCGTCAAAGCTTCACAGTGTCACAGGCATAGACACCAA 1800
AGACAAAAGCTTAAAGACTGTGAGTTCTGGGGCCAAGAAAAGTTTTGAAT 1850
TGCTCTCAGAGAGCGATGGGGCCTTGATGGAGCACCCAGAAGTATCTCAA 1900
GTGAGGAGGAAAACTGTGGAGTTTAACCTGACGGATATGCCAGAGATCCC 1950
CGAAAATCACCTCAAAGAACCTTTGGAACAATCACCAACCAACATACACA 2000
CTACACTCAAAGATCACATGGATCCTTATTGGGCCTTGGAAAACAGGGAT 2050
GAAGCACATTCCTAACCTGCTTCCTAATGGGGATGCTTCGCCAGCCAGGT 2100
CCTCACCTGTGTGTACACCAGCAGGACACTGATCCAGTCACAGCCATACA 2150
GCTGTCCACACTGAAGAACGTGTCCTACAACAGCCTGAATCAAATGGTTA 2200
GCTTAATAGATAAAAATCCCAGACTACTTCAGCCTTTAATGCCTTTTATT 2250
CATAAAAACTGTGAAAGCTAGACTGAACCATTGGAAACATTTAACTCAGA 2300
CTCTGGATTCAGAGTCGGGAACCCTTAGTTCTATCTGAATCCAAGACAGC 2350
CACACCTTAGTATACTGCCCAAACTAATGAGTTTAATAAATACAAATACT 2400
CGTTAAAAAAAAAAAAAAAAAAAAAAAAAAAA(SEQ.ID.NO.:4)
```

FIG.4

MTITYTSQVANARLGSFSRLLLCWRGSIYKLLYGEFLIFLLCYYIIRFIY 50
RLALTEEQQLMFEKLTLYCDSYIQLIPISFVLGFYVTLVVTRWWNQYENL 100
PWPDRLMSLVSGFVEGKDEQGRLLRRTLIRYANLGNVLILRSVSTAVYKR 150
FPSAQHLVQAGFMTPAEHKQLEKLSLPHNMFWVPWVWFANLSMKAWLGGR 200
IRDPILLQSLLNEMNTLRTQCGHLYAYDWISIPLVYTQVVTVAVYSFFLT 250
ICLVGRQFLNPAKAYPGHELDLVVPVFTFLQFFFYVGWLKVGLSRALLGWR 300
HGQRGHGQQLLETRMQCQERKVSRVESSQAWWRTPVIPATREAEAGESLE 350
PGRRRLWWQSSSSTPLERMMMILRPTGLSTGICRCPCWLWMRCTRTCLGW 400
SRTCTGISPSHSPPTQLLPPSSVEPPLWAPPSTSA (SEQ.ID.NO.:5)

FIG.5

Application No. 09/622,964
Amendment Dated: April 28, 2004
Reply to Communication Dated: April 6, 2004
REPLACEMENT SHEET
13/18

| GenBank/SwissProt accession numbers | Protein sequence | SEQ.ID.NO. |
|---|---|---|
| CG1CE_protein | IPISFVLGFY VTLVVTRWWN QYENLPWPDR | 32 (part) |
| af016687 (PID:g2315833) | IPLTFMLGFE VTIIVGRWND IFLNIGWVDN | 33 |
| z73105 (PID:e242363) | IPLTFMLGFE VTIIVRRWND IFANLGWVEN | 34 |
| z73422 (PID:e244423) | IPLEFVLGFE VTIVVDRWTK LWRTVGFIDD | 35 |
| z73422 (PID:e244542) | IPLEFVLGFE VTTVVNRWTK LYQTIGFIDN | 36 |
| p34577 | VPLDWMLGFE IAGVLRREWY LYDIIGFIDN | 37 |
| p34672 | IPLNFMLGFE VTAVVNRWTY LYQIIGFIDN | 38 |
| p34319 | LPLNFVLGFE CNIIIRRWLK LYTSLGNIDN | 39 |
| z68335 (PID:e217363) | IPINFMLGFE VTTVINRWMT QFANLGMIDN | 40 |
| z68753 (PID:e218704) | IPLTFLLGFE VSFVVARWGS ILNGIGWIDD | 41 |
| af025458 (PID:e2429439) | IPVTFMLGFY VSIVYNRWTK VFDNVGWIDT | 42 |
| u28412 (PID:g849242) | LPLTFMLGFE VTTVFERWRS ALNVMPFIES | 43 |
| u70848 (PID:g1572760) | IPLTFLLGFY VSNVVSRWWR QFETLRWPED | 44 |
| z81074 (PID:e351507) | IPLTFLLGFY VSNVVARWWR QFETLYWPED | 45 |
| q09379 | IPLTFLLGFY VAMIVRRWWD CCQLISWPDH | 46 |
| z72509 (PID:e239377) | IPLSFLLGFE VSLIVARWWE QFNCISWPDK | 47 |
| z83221 (PID:e349023) | VPMQPMLGYF IGMVGERWGE SFENVSYIEK | 48 |

FIG.7

```
  1 GTGCCAAGCCATGACTATCACCTACACAAACAAAGTAGCCAATGCCCGCCTCGGTTCGTT  60
  1           M  T  I  T  Y  T  N  K  V  A  N  A  R  L  G  S  F   17

61 CTCGTCCCTCCTCCTGTGCTGGCGAGGCAGCATCTACAAGCTGCTGTATGGAGAATTCCT 120
 18  S  S  L  L  L  C  W  R  G  S  I  Y  K  L  L  Y  G  E  F  L  37

121 TGTCTTCATATTCCTCTACTATTCCATCCGTGGACTCTACAGAATGGTTCTCTCGAGTGA 180
 38  V  F  I  F  L  Y  Y  S  I  R  G  L  Y  R  M  V  L  S  S  D  57

181 TCAGCAGCTGTTGTTTGAGAAGCTGGCTCTGTACTGCGACAGCTACATTCAGCTCATCCC 240
 58  Q  Q  L  L  F  E  K  L  A  L  Y  C  D  S  Y  I  Q  L  I  P  77

241 TATATCCTTCGTTCTGGGTTTCTATGTTACATTGGTGGTGAGCCGCTGGTGGAGCCAGTA 300
 78  I  S  F  V  L  G  F  Y  V  T  L  V  V  S  R  W  W  S  Q  Y  97

301 CGAGAACTTGCCGTGGCCCGACCGCCTCATGATCCAGGTGTCTAGCTTCGTGGAGGGCAA 360
 98  E  N  L  P  W  P  D  R  L  M  I  Q  V  S  S  F  V  E  G  K  117

361 GGATGAGGAAGGCCGTTTGCTGCGGCGCACGCTCATCCGCTACGCCATCCTGGGCCAAGT 420
118  D  E  E  G  R  L  L  R  R  T  L  I  R  Y  A  I  L  G  Q  V  137

421 GCTCATCCTGCGCAGCATCAGCACCTCGGTCTACAAGCGCTTTCCCACTCTTCACCACCT 480
138  L  I  L  R  S  I  S  T  S  V  Y  K  R  F  P  T  L  H  H  L  157

481 GGTGCTAGCAGGTTTTATGACCCATGGGGAACATAAGCAGTTGCAGAAGTTGGGCCTACC 540
158  V  L  A  G  F  M  T  H  G  E  H  K  Q  L  Q  K  L  G  L  P  177

541 ACACAACACATTCTGGGTGCCCTGGGTGTGGTTTGCCAACTTGTCAATGAAGGCCTATCT 600
178  H  N  T  F  W  V  P  W  V  W  F  A  N  L  S  M  K  A  Y  L  197

601 TGGAGGTCGAATCCGGGACACCGTCCTGCTCCAGAGCCTGATGAATGAGGTGTGTACTTT 660
198  G  G  R  I  R  D  T  V  L  L  Q  S  L  M  N  E  V  C  T  L  217

661 GCGTACTCAGTGTGGACAGCTGTATGCCTACGACTGGATAAGTATCCCATTGGTGTACAC 720
218  R  T  Q  C  G  Q  L  Y  A  Y  D  W  I  S  I  P  L  V  Y  T  237

721 ACAGGTGGTGACAGTGGCAGTATACAGCTTTTTCCTTGCATGCTTGATCGGGAGGCAGTT 780
238  Q  V  V  T  V  A  V  Y  S  F  F  L  A  C  L  I  G  R  Q  F  257
```

FIG.8A

```
 781 TCTGAACCCAAACAAGGACTACCCAGGCCATGAGATGGATCTGGTTGTGCCTGTCTTCAC 840
 258  L  N  P  N  K  D  Y  P  G  H  E  M  D  L  V  V  P  V  F  T  277

841 AATCCTGCAATTCTTATTCTACATGGGCTGGCTGAAGGTGGCAGAACAGCTCATCAACCC 900
 278  I  L  Q  F  L  F  Y  M  G  W  L  K  V  A  E  Q  L  I  N  P  297

901 CTTCGGGGAGGACGATGATGATTTTGAGACTAACTGGATCATTGACAGAAACCTGCAGGT 960
 298  F  G  E  D  D  D  D  F  E  T  N  W  I  I  D  R  N  L  Q  V  317

961 GTCCCTGTTGTCCGTGGATGGGATGCACCAGAACTTGCCTCCCATGGAACGTGACATGTA 1020
 318  S  L  L  S  V  D  G  M  H  Q  N  L  P  P  M  E  R  D  M  Y  337

1021 CTGGAACGAGGCAGCGCCTCAGCCGCCCTACACAGCTGCTTCTGCCAGGTCTCGCCGGCA 1080
 338  W  N  E  A  A  P  Q  P  P  Y  T  A  A  S  A  R  S  R  R  H  357

1081 TTCCTTCATGGGCTCCACCTTCAACATCAGCCTAAAGAAAGAAGACTTAGAGCTTTGGTC 1140
 358  S  F  M  G  S  T  F  N  I  S  L  K  K  E  D  L  E  L  W  S  377

1141 AAAAGAGGAGGCTGACACGGATAAGAAAGAGAGTGGCTATAGCAGCACCATAGGCTGCTT 1200
 378  K  E  E  A  D  T  D  K  K  E  S  G  Y  S  S  T  I  G  C  F  397

1201 CTTAGGACTGCAACCCAAAAACTACCATCTTCCCTTGAAAGACTTAAAGACCAAACTATT 1260
 398  L  G  L  Q  P  K  N  Y  H  L  P  L  K  D  L  K  T  K  L  L  417

1261 GTGTTCTAAGAACCCCCTCCTCGAAGGCCAGTGTAAGGATGCCAACCAGAAAAACCAGAA 1320
 418  C  S  K  N  P  L  L  E  G  Q  C  K  D  A  N  Q  K  N  Q  K  437

1321 AGATGTCTGGAAATTTAAGGGTCTGGACTTCTTGAAATGTGTTCCAAGGTTTAAGAGGAG 1380
 438  D  V  W  K  F  K  G  L  D  F  L  K  C  V  P  R  F  K  R  R  457

1381 AGGCTCCCATTGTGGCCCACAGGCACCCAGCAGCCACCCTACTGAGCAGTCAGCACCCTC 1440
 458  G  S  H  C  G  P  Q  A  P  S  S  H  P  T  E  Q  S  A  P  S  477

1441 CAGTTCAGACACAGGTGATGGGCCTTCCACAGATTACCAAGAAATCTGTCACATGAAAAA 1500
 478  S  S  D  T  G  D  G  P  S  T  D  Y  Q  E  I  C  H  M  K  K  497

1501 GAAAACTGTGGAGTTTAACTTGAACATTCCAGAGAGCCCCACAGAACATCTTCAACAGCG 1560
 498  K  T  V  E  F  N  L  N  I  P  E  S  P  T  E  H  L  Q  Q  R  517

1561 CCGTTTGGACCAGATGTCAACCAATATACAGGCTCTAATGAAGGAGCATGCAGAGTCCTA 1620
```

1621  TCCCTACAGGGATGAAGCTGGCACCAAACCTGTTCTCTATGAGTGATGCCTCACAGCCTG  1680
 538  P  Y  R  D  E  A  G  T  K  P  V  L  Y  E                     551

1681  GCCCTGACTTGCAAGGATGCCCAGCAGGGCACTGACCCAGTCAAAGGCACACAAGCAGCG  1740

1741  ACACCCAGGAGTGTGTTCCCACGACAGTCTAGCATGTAACTCAGAACCAAGAGTACTTAA  1800

1801  TAGTCCTGCCTGAAAACACCTGTATTTTACGATCTTTCCCAAACTAAGGAGTTTAATAAA  1860

1861  CGTGAATATTCTTTTAGGTGAAAAAAAAAAAAAAAAAAAAAAAAAAAAAAAAAAAAAA    1916
```

FIG.8C

```
                          1                                                       50
              Human   MTITYTSQVA  NARLGSFSRL  LLCWRGSIYK  LLYGEFLIFL  LCYYIIRFIY
       MouseBestrophin]  MTITYTNKVA  NARLGSFSSL  LLCWRGSIYK  LLYGEFLVFI  FLYYSIRGLY 51                                                      100
              Human   RLALTEEQQL  MFEKLTLYCD  SYIQLIPISF  VLGFYVTLVV  TRWWNQYENL
       MouseBestrophin]  RMVLSSDQQL  LFEKLALYCD  SYIQLIPISF  VLGFYVTLVV  SRWWSQYENL 101                                                      150
              Human   PWPDRLMSLV  SGFVEGKDEQ  GRLLRRTLIR  YANLGNVLIL  RSVSTAVYKR
       MouseBestrophin]  PWPDRLMIQV  SSFVEGKDEE  GRLLRRTLIR  YAILGQVLIL  RSISTSVYKR 151                                                      200
              Human   FPSAQHLVQA  GFMTPAEHKQ  LEKLSLPHNM  FWVPWVWFAN  LSMKAWLGGR
       MouseBestrophin]  FPTLHHLVLA  GFMTHGEHKQ  LQKLGLPHNT  FWVPWVWFAN  LSMKAYLGGR 201                                                      250
              Human   IRDPILLQSL  LNEMNTLRTQ  CGHLYAYDWI  SIPLVYTQVV  TVAVYSFFLT
       MouseBestrophin]  IRDTVLLQSL  MNEVCTLRTQ  CGQLYAYDWI  SIPLVYTQVV  TVAVYSFFLA 251                                                      300
              Human   CLVGRQFLNP  AKAYPGHELD  LVVPVFTFLQ  FFFYVGWLKV  AEQLINPFGE
       MouseBestrophin]  CLIGRQFLNP  NKDYPGHEMD  LVVPVFTILQ  FLFYMGWLKV  AEQLINPFGE 301                                                      350
              Human   DDDDFETNWI  VDRNLQVSLL  AVDEMHQDLP  RMEPDMYWNR  PEPQPPYTAA
       MouseBestrophin]  DDDDFETNWI  IDRNLQVSLL  SVDGMHQNLP  PMERDMYWNE  AAPQPPYTAA 351                                                      400
              Human   SAQFRRASFM  GSTFNISLNK  EEMEFQPNQE  ....DEEDAH  AGIIGRFLGL
       MouseBestrophin]  SARSRRHSFM  GSTFNISLKK  EDLELWSKEE  ADTDKKESGY  SSTIGCFLGL 401                                                      450
              Human   QSHDHHPPRA  NSRTKLLWPK  RESLLHEGLP  KNHKAAKQNV  RGQEDNKAWK
       MouseBestrophin]  QPKNYHLPLK  DLKTKLLCSK  NPLL..EGQC  KD.....ANQ  KNQKD..VWK 451                                                      500
              Human   LKAVDAFKSA  PLYQRPGYYS  APQTPLSPTP  MFFPLEPSAP  SKLHSVTGID
       MouseBestrophin]  FRGLDFLKCV  PRFKRRGSHC  GPQAPSS...  ..HPTEQSAP  SS..SDTG..

501                                                      550
              Human   TKDKSLKTVS  SGAKKSFELL  SESDGALMEH  PEVSQVRRKT  VEFNLTDMPE
       MouseBestrophin]  ..........  ..........  ...DGPSTDY  QEICHMKKKT  VEFNL.NIPE 551                                                      596
              Human   IPENHLKE.P  LEQSPTNIHT  TLKDHMDPYW  ALENRDEAHS  ——————
       MouseBestrophin]  SPTEHLQQRR  LDQMSTNIQA  LMKEHAESY.  ..PYRDEAGT  KPVLYE
```

FIG.9

BEST'S MACULAR DYSTROPHY GENE

CROSS-REFERENCE TO RELATED APPLICATIONS

This application claims the benefit of U.S. Provisional Application No. 60/122,926, filed Dec. 18, 1998 and U.S. Provisional Application No. 60/075,941, filed Feb. 25, 1998, the contents of which are incorporated herein by reference in their entirety.

STATEMENT REGARDING FEDERALLY-SPONSORED R&D

Not applicable.

REFERENCE TO MICROFICHE APPENDIX

Not applicable.

FIELD OF THE INVENTION

The present invention is directed to novel human and mouse DNA sequences encoding a protein which, when present in mutated form, results in the occurrence of Best's Macular Dystrophy.

BACKGROUND OF THE INVENTION

Macular dystrophy is a term applied to a heterogeneous group of diseases that collectively are the cause of severe visual loss in a large number of people. A common characteristic of macular dystrophy is a progressive loss of central vision resulting from the degeneration of the pigmented epithelium underlying the retinal macula. In many forms of macular dystrophy, the end stage of the disease results in legal blindness. More than 20 types of macular dystrophy are known: e.g., age-related macular dystrophy, Stargardt's disease, atypical vitelliform macular dystrophy (VMD1), Usher Syndrome Type 1B, autosomal dominant neovascular inflammatory vitreoretinopathy, familial exudative vitreoretinopathy, and Best's macular dystrophy (also known as hereditary macular dystrophy or Best's vitelliform macular dystrophy (VMD2)). For a review of the macular dystrophies, see Sullivan & Daiger, 1996, Mol. Med. Today 2:380–386.

Best's Macular Dystrophy (BMD) is an inherited autosomal dominant macular dystrophy of unknown biochemical cause. BMD has an age of onset that can range from childhood to after 40. Clinical symptoms include, at early stages, an abnormal accumulation of the yellowish material lipofuscin in the retinal pigmented epithelium (RPE) underlying the macula. This gives rise to a characteristic "egg yolk" appearance of the RPE and gradual loss of visual acuity. With increasing age, the RPE becomes more and more disorganized, as the lipofuscin accumulations disperse and scarring and neovascularization take place. These changes are accompanied by further loss of vision.

The pathological features seen in BMD are in many ways similar to the features seen in age-related macular dystrophy, the leading cause of blindness in older patients in the developed world. Age-related macular dystrophy is an extraordinarily difficult disease to study genetically, since by the time patients are diagnosed, their parents are usually no longer living and their children are still asymptomatic. Thus, family studies which have led to the discovery of the genetic basis of many other diseases have not been practical for age-related macular dystrophy. As there are currently no widely effective treatments for age-related macular dystrophy, it is hoped that study of BMD, and in particular the discovery of the underlying genetic cause of BMD, will shed light on age-related macular dystrophy as well.

Linkage analysis has established that the gene responsible for BMD resides in the pericentric region of chromosome 11, at 11q13, near the markers D11S956, FCER1B, and UGB (Forsman et al., 1992, Clin. Genet. 42:156–159; Hou et al., 1996, Human Heredity 46:211–220). Recently, the gene responsible for BMD was localized to a ~1.7 mB PAC contig lying mostly between the markers D11S1765 and UGB (Cooper et al., 1997, Genomics 41:185–192). Recombination breakpoint mapping in a large Swedish pedigree limited the minimum genetic region containing the BMD gene to a 980 kb interval flanked by the microsatellite markers D11S4076 and UGB (Graff et al., 1997, Hum. Genet. 101: 263–279).

One difficulty in diagnosing BMD is that carriers of the diseased gene for BMD may be asymptomatic in terms of visual acuity and morphological changes of the RPE observable in a routine ophthalmologic examination. There does exist a test, the electro-oculographic examination (EOG), which detects differences in electrical potential between the cornea and the retina, that can distinguish asymptomatic BMD patients from normal individuals. However, the EOG requires specialized, expensive equipment, is difficult to administer, and requires that the patient be present at the site of the equipment when the test is performed. It would be valuable to have an alternative method of diagnosing asymptomatic carriers of mutations in the gene responsible for BMD that is simpler, less expensive, and does not require the presence of the patient while the test is being performed. For example, a diagnostic test that relies on a blood sample from a patient suspected of being an asymptomatic carrier of BMD would be ideal.

SUMMARY OF THE INVENTION

The present invention is directed to novel human and mouse DNA sequences that encode the gene CG1CE, which, when mutated, is responsible for Best's macular dystrophy. The present invention includes genomic CG1CE DNA as well as cDNA that encodes the CG1CE protein. The human genomic CG1CE DNA is substantially free from other nucleic acids and has the nucleotide sequence shown in SEQ.ID.NO.:1. The human cDNA encoding CG1CE protein is substantially free from other nucleic acids and has the nucleotide sequence shown in SEQ.ID.NO.:2 or SEQ.ID.NO.:4. The mouse cDNA encoding CG1CE protein is substantially free from other nucleic acids and has the nucleotide sequence shown in SEQ.ID.NO.:28. Also provided is CG1CE protein encoded by the novel DNA sequences. The human CG1CE protein is substantially free from other proteins and has the amino acid sequence shown in SEQ.ID.NO.:3 or SEQ.ID.NO.:5. The mouse CG1CE protein is substantially free from other proteins and has the amino acid sequence shown in SEQ.ID.NO.:29. Methods of expressing CG1CE protein in recombinant systems are provided. Also provided are diagnostic methods that detect carriers of mutant CG1CE genes.

BRIEF DESCRIPTION OF THE DRAWINGS

FIGS. 1A–F shows the genomic DNA sequence of human CG1CE (SEQ.ID.NO.: 1). Underlined nucleotides in capitals represent exons. The start ATG codon in exon 2 and the stop TAA codon in exon 11 are shown in bold italics. The consensus polyadenylation signal AATAAA in exon 11 is shown in bold. The alternatively spliced part of exon 7 is shown in underlined italics. The exact lengths of two gaps between exons 1 and 2 and between exons 7 and 8 are unknown; these gaps are presented as runs of ten Ns for the sake of convenience. The portion of exon 11 beginning at position 15,788 represents the 3' untranslated region; 132 base pairs downstream of the polyadenylation signal of the CG1CE gene are multiple ESTs, representing the 3'-untranslated region of the ferritin heavy chain gene (FTH). FTH has been mapped to human chromosome 11q13 (Hentze et al., 1986, Proc. Nat. Acad. Sci. 83: 7226–7230); the FTH gene was later shown to be a part of the smallest minimum genetic region containing the BMD gene, as determined by recombination breakpoint mapping in a 12 generation Swedish pedigree (Graff et al., 1997, Hum. Genet. 101: 263–279).

FIG. 2 shows the complete sequence of the short form of human CG1CE cDNA (SEQ.ID.NO.:2). The ATG start codon is at position 105; the TAA stop codon is at position 1,860.

FIG. 3 shows the complete amino acid sequence of the long form of human CG1CE protein (SEQ.ID.NO.:3). This long form of the human CG1CE protein is produced by translation of the short form of CG1CE cDNA.

FIG. 4 shows the complete sequence of the long form of human CG1CE cDNA (SEQ.ID.NO.:4). This long form of the human CG1CE cDNA is produced when an alternative splice donor site is utilized in intron 7. The ATG start codon is at position 105; the TGA stop codon is at position 1410.

FIG. 5 shows the complete amino acid sequence of the short form of the human CG1CE protein (SEQ.ID.NO.:5). This short form of the human CG1CE orotein is produced by translation of the long form of CG1CE cDNA.

FIG. 7 shows a multiple sequence alignment of human CG1CE protein with partial sequences of related proteins from *C. elegans*. Related proteins from *C. elegans* were identified by BLASTP analysis of non-redundant GenBank database. This figure shows that two amino acids mutated in two different Swedish families with BMD (families S1 and SL76) are evolutionarily conserved. 15 of 16 related proteins from *C. elegans* contain a tryptophan at the position of the mutation in family S1, as does the wild-type CG1CE gene. Only one *C. elegans* protein does not have a tryptophan at the position of the mutation. In this protein (accession number p34577), tryptophan is changed for isofunctional phenylalanine (phenylalanine is highly similar to tryptophan in that it also is a hydrophobic aromatic amino acid). Mutation in the BMD family SL76 changes a tyrosine to histidine. Again, all 16 related proteins from *C. elegans* contain tyrosine or isofunctional phenylalanine in this position (tyrosine is highly similar to phenylalanine in that it also is an aromatic amino acid).

FIGS. 8A–C shows the complete sequence of mouse CG1CE cDNA (SEQ.ID.NO.:28) and mouse CG1CE protein (SEQ.ID.NO.:29).

FIGS. 9A–B shows an alignment of the amino acid sequences of the long form of human CG1CE protein (SEQ.ID.NO.:3) and mouse CG1CE protein (SEQ.ID.NO.:29). In this figure, CG1CE is referred to as "bestrophin."

FIG. 10A shows the results of using an antisense CG1CE probe. The antisense probe hybridizes to mouse CG1CE mRNA present in the various cell layers of the retina, labeling with dark bands the cells containing CG1CE mRNA. The antisense probe strongly hybridized to the RPE cells and not to the cells of the other layers of the retina. FIG. 10B shows the results using a sense CG1CE probe as a control. The sense probe does not hybridize to CG1CE mRNA and does not label the RPE cells. FIG. 10C is a higher magnification of the RPE cells from FIG. 10A. Human CG1CE mRNA shows a similar distribution, being confined to the RPE cells of the human retina.

DETAILED DESCRIPTION OF THE INVENTION

Figure 6A:
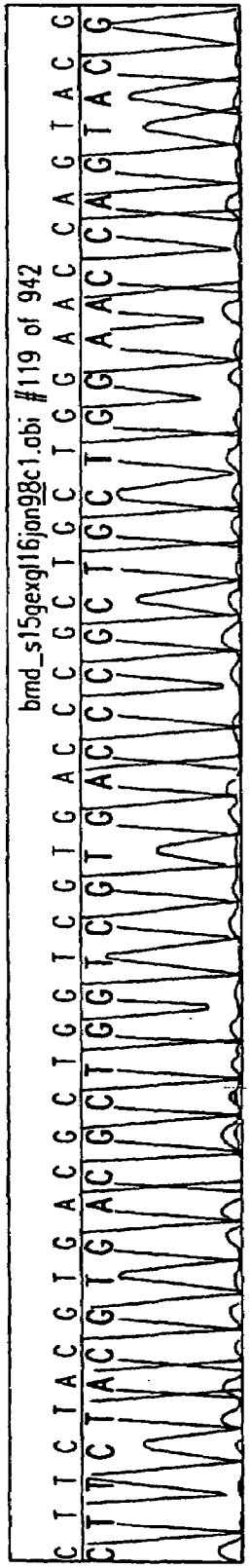
FIG. 6 shows the results of sequencing runs of PCR fragments that represent exon 4 and adjacent intronic regions from three individuals from the Swedish pedigree S1, two of whom are affected with BMD. From top to bottom, the runs are: patient S1-5 (homozygous affected with BMD), sense orientation; patient S1-4 (heteroozygous affected with BMD), sense orientation; patient S1-3 (normal control, unaffected sister of S1-4), sense orientation; patient S1-5 (affected with BMD), anti-sense orientation; patient S1-4 (affected with BMD), anti-sense orientation; patient S1-3 (normal control), anti-sense orientation. Reading from left to right, the mutation shows up at position 31 of the sequence shown in the case of patients S1-5 and S1-4. The mutation in family S1 changes tryptophan to cysteine.
Figure 6B:
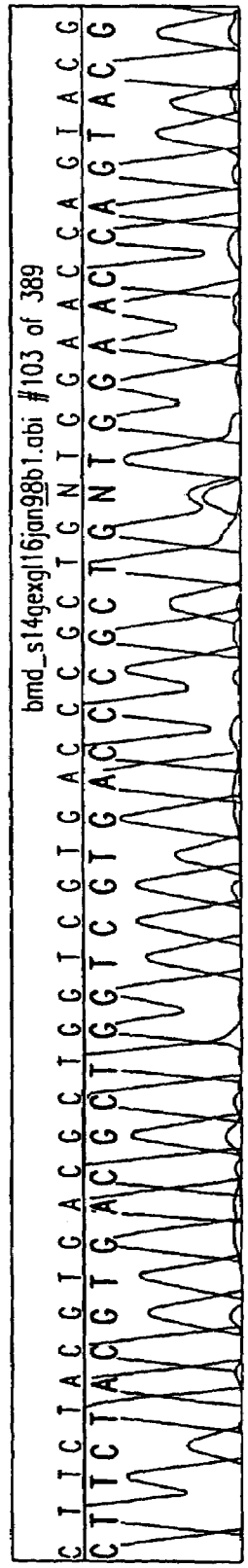
Figure 6C:
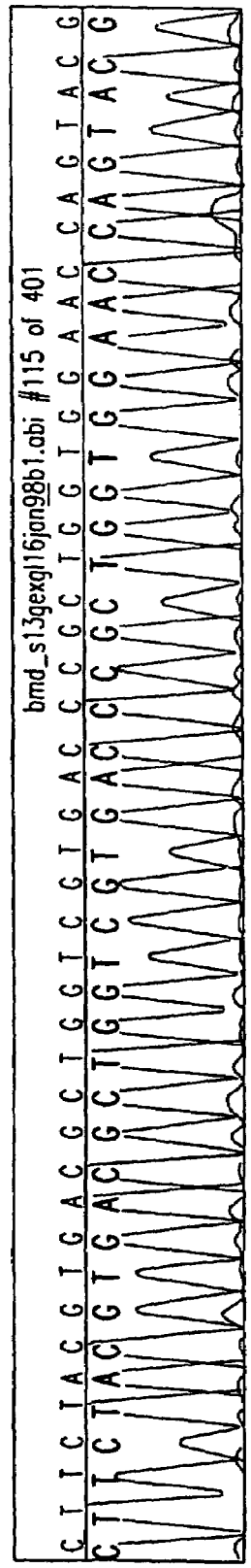
Figure 6D:
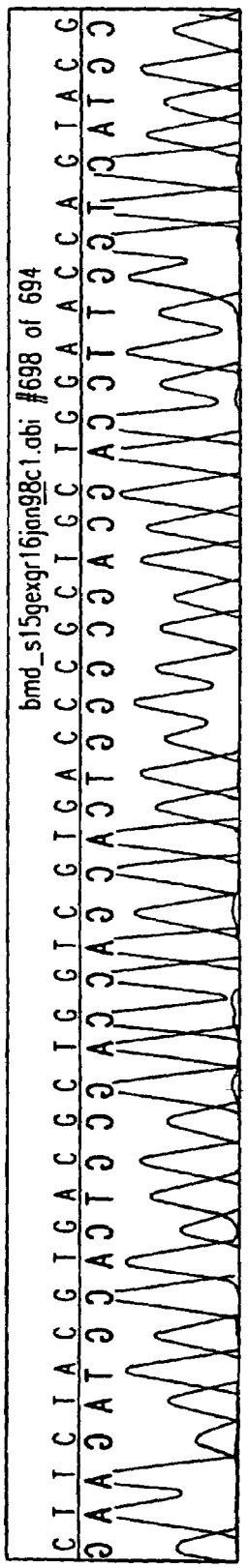
Figure 6E:
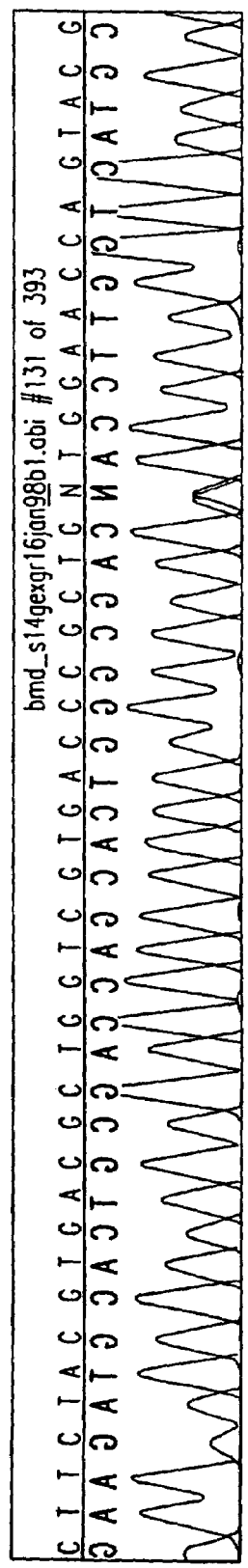
Figure 6F:
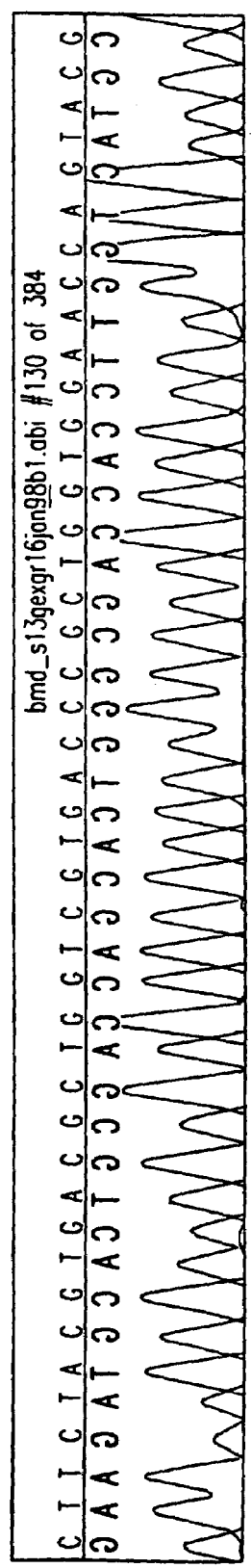

For the purposes of this invention:

"Substantially free from other proteins" means at least 90%, preferably 95%, more preferably 99%, and even more preferably 99.9%, free of other proteins. Thus, a CG1CE protein preparation that is substantially free from other proteins will contain, as a percent of its total protein, no more than 10%, preferably no more than 5%, more preferably no more than 1%, and even more preferably no more than 0.1%, of non-CG1CE proteins. Whether a given CG1CE protein preparation is substantially free from other proteins can be determined by such conventional techniques of assessing protein purity as, e.g., sodium dodecyl sulfate polyacrylamide gel electrophoresis (SDS-PAGE) combined with appropriate detection methods, e.g., silver staining or immunoblotting.

"Substantially free from other nucleic acids" means at least 90%, preferably 95%, more preferably 99%, and even more preferably 99.9%, free of other nucleic acids. Thus, a CG1CE DNA preparation that is substantially free from other nucleic acids will contain, as a percent of its total nucleic acid, no more than 10%, preferably no more than 5%, more preferably no more than 1%, and even more preferably no more than 0.1%, of non-CG1CE nucleic acids. Whether a given CG1CE DNA preparation is substantially free from other nucleic acids can be determined by such conventional techniques of assessing nucleic acid purity as, e.g., agarose gel electrophoresis combined with appropriate staining methods, e.g., ethidium bromide staining, or by sequencing.

A "conservative amino acid substitution" refers to the replacement of one amino acid residue by another, chemically similar, amino acid residue. Examples of such conservative substitutions are: substitution of one hydrophobic residue (isoleucine, leucine, valine, or methionine) for another; substitution of one polar residue for another polar residue of the same charge (e.g., arginine for lysine; glutamic acid for aspartic acid); substitution of one aromatic amino acid (tryptophan, tyrosine, or phenylalanine) for another.

The present invention relates to the identification and cloning of CG1CE, a gene which, when mutated, is responsible for Best's macular dystrophy. That CG1CE is the Best's macular dystrophy gene is supported by various observations:

1. CG1CE maps to the genetically defined region of human chromosome 11q12–q13 that has been shown to contain the Best's macular dystrophy gene. CG1CE is present on two PAC clones, 759J12 and 466A11, that lie precisely in the most narrowly defined region that has been shown to contain CG1CE (Cooper et al., 1997, Genomics 41:185–192; Stöhr et al., 1997, Genome Res. 8:48–56; Graff et al., 1997, Hum. Genet. 101: 263–279).
2. CG1CE is expressed predominately in the retina.
3. In patients having Best's macular dystrophy, CG1CE contains mutations in evolutionarily conserved amino acids.
4. The CG1CE genomic clones contain another gene (FTH) that has been physically associated with the Best's macular dystrophy region (Cooper et al., 1997, Genomics 41:185–192; Stöhr et al., 1997, Genome Res. 8:48–56; Graff et al., 1997, Hum. Genet. 101: 263–279). The FTH and CG1CE genes are oriented tail-to-tail; the distance between their polyadenylation signals is 132 bp.

The present invention provides DNA encoding CG1CE that is substantially free from other nucleic acids. The present invention also provides recombinant DNA molecules encoding CG1CE. The present invention provides DNA molecules substantially free from other nucleic acids comprising the nucleotide sequence shown in FIG. 1 as SEQ.ID.NO.: 1. Analysis of SEQ.ID.NO.: 1 revealed that this genomic sequence defines a gene having 11 exons. These exons collectively have an open reading frame that encodes a protein of 585 amino acids. If an alternative splice donor site is utilized in exon 7, a cDNA containing an additional 203 bases is produced. Although longer, this cDNA contains a shorter open reading frame of 1,305 bases (due to the presence of a change in reading frame that introduces a stop codon) that encodes a protein of 435 amino acids. Thus, the present invention includes two cDNA molecules encoding two forms of CG1CE protein that are substantially free from other nucleic acids and have the nucleotide sequences shown in FIG. 2 as SEQ.ID.NO.:2 and in FIG. 4 as SEQ.ID.NO.:4.

The present invention includes DNA molecules substantially free from other nucleic acids comprising the coding regions of SEQ.ID.NO.:2 and SEQ.ID.NO.:4. Accordingly, the present invention includes DNA molecules substantially free from other nucleic acids having a sequence comprising positions 105–1,859 of SEQ.ID.NO.:2 and positions 105–1,409 of SEQ.ID.NO.:4. Also included are recombinant DNA molecules having a nucleotide sequence comprising positions 105–1,859 of SEQ.ID.NO.:2 and positions 105–1,409 of SEQ.ID.NO.:4.

Portions of the cDNA sequences of SEQ.ID.NO.:2 and SEQ.ID.NO.:4 are found in two retina-specific ESTs deposited in GenBank by The Institute for Genomic Research (accession numbers AA318352 and AA317489). Other ESTSs that correspond to this cDNA are accession numbers AA307119 (from a colon carcinoma), AA205892 (from neuronal cell line), and AA326727 (from human cerebellum). A true mouse ortholog of the CG1CE gene is represented in the mouse EST AA497726 (from mouse testis).

The novel DNA sequences of the present invention encoding CG1CE, in whole or in part, can be linked with other DNA sequences, i.e., DNA sequences to which CG1CE is not naturally linked, to form "recombinant DNA molecules" encoding CG1CE. Such other sequences can include DNA sequences that control transcription or translation such as, e.g., translation initiation sequences, promoters for RNA polymerase II, transcription or translation termination sequences, enhancer sequences, sequences that control replication in microorganisms, sequences that confer antibiotic resistance, or sequences that encode a polypeptide "tag" such as, e.g., a polyhistidine tract or the myc epitope. The novel DNA sequences of the present invention can be inserted into vectors such as plasmids, cosmids, viral vectors, P1 artificial chromosomes, or yeast artificial chromosomes.

Included in the present invention are DNA sequences that hybridize to at least one of SEQ.ID.NOs.: 1, 2, or 4 under stringent conditions. By way of example, and not limitation, a procedure using conditions of high stringency is as follows: Prehybridization of filters containing DNA is carried out for 2 hr. to overnight at 65° C. in buffer composed of 6× SSC, 5× Denhardt's solution, and 100 µg/ml denatured salmon sperm DNA. Filters are hybridized for 12 to 48 hrs at 65° C. in prehybridization mixture containing 100 µg/ml denatured salmon sperm DNA and 5–20×10$^6$ cpm of $^{32}$P-labeled probe. Washing of filters is done at 37° C. for 1 hr in a solution containing 2× SSC, 0.1% SDS. This is followed by a wash in 0.1× SSC, 0.1% SDS at 50° C. for 45 min. before autoradiography.

Other procedures using conditions of high stringency would include either a hybridization carried out in 5× SSC, 5× Denhardt's solution, 50% formamide at 42° C. for 12 to 48 hours or a washing step carried out in 0.2× SSPE, 0.2% SDS at 65° C. for 30 to 60 minutes.

Reagents mentioned in the foregoing procedures for carrying out high stringency hybridization are well known in the art. Details of the composition of these reagents can be found in, e.g., Sambrook, Fritsch, and Maniatis, 1989, *Molecular Cloning: A Laboratory Manual*, second edition, Cold Spring Harbor Laboratory Press. In addition to the foregoing, other conditions of high stringency which may be used are well known in the art.

The degeneracy of the genetic code is such that, for all but two amino acids, more than a single codon encodes a particular amino acid. This allows for the construction of synthetic DNA that encodes the CG1CE protein where the nucleotide sequence of the synthetic DNA differs significantly from the nucleotide sequences of SEQ.ID.NOs.:2 or 4, but still encodes the same CG1CE protein as SEQ.ID.NOs.:2 or 4. Such synthetic DNAs are intended to be within the scope of the present invention.

Mutated forms of SEQ.ID.NOs.: 1, 2, or 4 are intended to be within the scope of the present invention. In particular, mutated forms of SEQ.ID.NOs.: 1, 2, or 4 which give rise to Best's macular dystrophy are within the scope of the present invention. Accordingly, the present invention includes a DNA molecule having a nucleotide sequence that is identical to SEQ.ID.NO.:1 except that the nucleotide at position 7,259 of SEQ.ID.NO.: 1 is T, A, or C rather than G, so that the codon at positions 7,257–7,259 encodes either cysteine or is a stop codon rather than encoding tryptophan. Also included in the present invention is a DNA molecule having a nucleotide sequence that is identical to SEQ.ID.NO.: 1 except that at least one of the nucleotides at position 7,257 or 7,258 has been changed so that the codon at positions 7,257–7,259 does not encode tryptophan.

The present invention includes a DNA molecule having a nucleotide sequence that is identical to positions 105–1,859 of SEQ.ID.NO.:2 except that the nucleotide at position 383 is T, A, or C rather than G, so that the codon at positions 381–383 encodes either cysteine or is a stop codon rather than encoding tryptophan. Also included in the present invention is a DNA molecule having a nucleotide sequence that is identical to positions 105–1,859 of SEQ.ID.NO.:2 except that at least one of the nucleotides at position 381 or 382 has been changed so that the codon at positions 381–383 does not encode tryptophan.

The present invention includes a DNA molecule having a nucleotide sequence that is identical to positions 105–1,409 of SEQ.ID.NO.:4 except that the nucleotide at position 383 is T, A, or C rather than G, so that the codon at positions 381–383 encodes either cysteine or is a stop codon rather than encoding tryptophan. Also included in the present invention is a DNA molecule having a nucleotide sequence that is identical to positions 105–1,409 of SEQ.ID.NO.:4 except that at least one of the nucleotides at position 381 or 382 has been changed so that the codon at positions 381–383 does not encode tryptophan.

The present invention includes a DNA molecule having a nucleotide sequence that is identical to SEQ.ID.NO.: 1 except that the nucleotide at position 7,233 of SEQ.ID.NO.:1 is C, A, or G rather than T, so that the codon at positions 7,233–7,235 does not encode tyrosine. Also included in the present invention is a DNA molecule having a nucleotide sequence that is identical to SEQ.ID.NO.:1 except that at least one of the nucleotides at position 7,234 or 7,235 has been changed so that the codon at positions 7,233–7,235 does not encode tyrosine.

The present invention includes a DNA molecule having a nucleotide sequence that is identical to positions 105–1,859 of SEQ.ID.NO.:2 except that the nucleotide at position 357 is C, A, or G rather than T, so that the codon at positions 357–359 does not encode tyrosine. Also included in the present invention is a DNA molecule having a nucleotide sequence that is identical to positions 105–1,859 of SEQ.ID.NO.:2 except that at least one of the nucleotides at position 358 or 359 has been changed so that the codon at positions 357–359 does not encode tyrosine.

The present invention includes a DNA molecule having a nucleotide sequence that is identical to positions 105–1,409 of SEQ.ID.NO.:4 except that the nucleotide at position 357 is C, A, or G rather than T, so that the codon at positions 357–359 does not encode tyrosine. Also included in the present invention is a DNA molecule having a nucleotide sequence that is identical to positions 105–1,409 of SEQ.ID.NO.:4 except that at least one of the nucleotides at position 358 or 359 has been changed so that the codon at positions 357–359 does not encode tyrosine.

The present invention includes a DNA molecule having a nucleotide sequence that is identical to SEQ.ID.NO.:1 except that the nucleotide at position 3,330 is C rather than A. Also included in the present invention is a DNA molecule having a nucleotide sequence that is identical to SEQ.ID.NO.:1 except that the nucleotide at position 3,330 of SEQ.ID.NO.: 1 is G, C, or T rather than A, so that the codon at positions 3,330–3,332 does not encode threonine. Also included in the present invention is a DNA molecule having a nucleotide sequence that is identical to SEQ.ID.NO.: 1 except that at least one of the nucleotides at position 3,330 or 3,331 has been changed so that the codon at positions 3,330–3,332 does not encode threonine.

The present invention includes a DNA molecule having a nucleotide sequence that is identical to positions 105–1,859 of SEQ.ID.NO.:2 except that the nucleotide at position 120 is C rather than A. Also included in the present invention is a DNA molecule having a nucleotide sequence that is identical to positions 105–1,859 of SEQ.ID.NO.:2 except that the nucleotide at position 120 is G, C, or T rather than A, so that the codon at positions 120–122 does not encode threonine. Also included in the present invention is a DNA molecule having a nucleotide sequence that is identical to positions 105–1,859 of SEQ.ID.NO.:2 except that at least one of the nucleotides at position 120 or 121 has been changed so that the codon at positions 120–122 does not encode threonine.

The present invention includes a DNA molecule having a nucleotide sequence that is identical to positions 105–1,409 of SEQ.ID.NO.:4 except that the nucleotide at position 120 is C rather than A. Also included in the present invention is a DNA molecule having a nucleotide sequence that is identical to positions 105–1,409 of SEQ.ID.NO.:4 except that the nucleotide at position 120 is G, C, or T rather than A, so that the codon at positions 120–122 does not encode threonine. Also included in the present invention is a DNA molecule having a nucleotide sequence that is identical to positions 105–1,409 of SEQ.ID.NO.:4 except that at least one of the nucleotides at position 120 or 121 has been changed so that the codon at positions 120–122 does not encode threonine.

The present invention includes a DNA molecule having a nucleotide sequence that is identical to SEQ.ID.NO.: 1 except that the nucleotide at position 8,939 is A rather than T. Also included in the present invention is a DNA molecule having a nucleotide sequence that is identical to SEQ.ID.NO.: 1 except that the nucleotide at position 8,939 of SEQ.ID.NO.: 1 is A, G, or C, rather than T, so that the codon at positions 8,939–8,941 does not encode tyrosine. Also included in the present invention is a DNA molecule having a nucleotide sequence that is identical to SEQ.ID.NO.:1 except that at least one of the nucleotides at position 8,939–8,941 has been changed so that the codon at positions 8,939–8,941 does not encode tyrosine.

The present invention includes a DNA molecule having a nucleotide sequence that is identical to positions 105–1,859 of SEQ.ID.NO.:2 except that the nucleotide at position 783 is A rather than T, Also included in the present invention is a DNA molecule having a nucleotide sequence that is identical to positions 105–1,859 of SEQ.ID.NO.:2 except that the nucleotide at position 783 is A, G, or C rather than T so that the codon at positions 783–785 does not encode tyrosine. Also included in the present invention is a DNA molecule having a nucleotide sequence that is identical to positions 105–1,859 of SEQ.ID.NO.:2 except that at least one of the nucleotides at position 783–785 has been changed so that the codon at positions 783–785 does not encode tyrosine.

The present invention includes a DNA molecule having a nucleotide sequence that is identical to positions 105–1,409 of SEQ.ID.NO.:4 except that the nucleotide at position 783 is A rather than T. Also included in the present invention is a DNA molecule having a nucleotide sequence that is identical to positions 105–1,409 of SEQ.ID.NO.:4 except that the nucleotide at position 783 is A, G, or C rather than T, so that the codon at positions 783–785 does not encode tyrosine. Also included in the present invention is a DNA molecule having a nucleotide sequence that is identical to positions 105–1,409 of SEQ.ID.NO.:4 except that at least one of the nucleotides at position 783–785 has been changed so that the codon at positions 783–785 does not encode tyrosine.

The present invention includes a DNA molecule having a nucleotide sequence that is identical to SEQ.ID.NO.: 1 except that the nucleotide at position 11,241 is A rather than G. Also included in the present invention is a DNA molecule having a nucleotide sequence that is identical to SEQ.ID.NO.: 1 except that the nucleotide at position 11,241 is A, C, or T, rather than G, so that the codon at positions 11,240–11,242 does not encode glycine. Also included in the present invention is a DNA molecule having a nucleotide sequence that is identical to SEQ.ID.NO.:1 except that at least one of the nucleotides at position 11,240 or 11,241 has been changed so that the codon at positions 11,240–11,242 does not encode glycine.

The present invention includes a DNA molecule having a nucleotide sequence that is identical to positions 105–1,859 of SEQ.ID.NO.:2 except that the nucleotide at position 1,000 is A rather than G. Also included in the present invention is a DNA molecule having a nucleotide sequence that is identical to positions 105–1,859 of SEQ.ID.NO.:2 except that the nucleotide at position 1,000 is A, C, or T rather than G, so that the codon at positions 999–1,001 does not encode glycine. Also included in the present invention is a DNA molecule having a nucleotide sequence that is identical to positions 105–1,859 of SEQ.ID.NO.:2 except that at least one of the nucleotides at position 999 or 1,000 has been changed so that the codon at positions 999–1,001 does not encode glycine.

Another aspect of the present invention includes host cells that have been engineered to contain and/or express DNA sequences encoding CG1CE protein. Such recombinant host cells can be cultured under suitable conditions to produce CG1CE protein. An expression vector containing DNA encoding CG1CE protein can be used for expression of CG1CE protein in a recombinant host cell. Recombinant host cells may be prokaryotic or eukaryotic, including but not limited to, bacteria such as *E. coli*, fungal cells such as yeast, mammalian cells including, but not limited to, cell lines of human, bovine, porcine, monkey and rodent origin, and insect cells including but not limited to *Drosophila* and silkworm derived cell lines. Cell lines derived from mammalian species which are suitable for recombinant expression of CG1CE protein and which are commercially available, include but are not limited to, L cells L-M(TK⁻) (ATCC CCL 1.3), L cells L-M (ATCC CCL 1.2), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C1271 (ATCC CRL 1616), BS-C-1 (ATCC CCL 26) and MRC-5 (ATCC CCL 171).

A variety of mammalian expression vectors can be used to express recombinant CG1CE in mammalian cells. Commercially available mammalian expression vectors which are suitable include, but are not limited to, pMC1neo (Stratagene), pSG5 (Stratagene), pcDNAI and pcDNAIamp, pcDNA3, pcDNA3.1, pCR3.1 (Invitrogen), EBO-pSV2-neo (ATCC 37593), pBPV-1(8-2) (ATCC 37110), pdBPV-MMT-neo(342-12) (ATCC 37224), pRSVgpt (ATCC 37199), pRS-Vneo (ATCC 37198), and pSV2-dhfr (ATCC 37146). Following expression in recombinant cells, CG1CE can be purified by conventional techniques to a level that is substantially free from other proteins.

The present invention includes CG1CE protein substantially free from other proteins. The amino acid sequence of the full-length CG1CE protein is shown in FIG. 3 as SEQ.ID.NO.:3. Thus, the present invention includes CG1CE protein substantially free from other proteins having the amino acid sequence SEQ.ID.NO.:3. Also included in the present invention is a CG1CE protein that is produced from an alternatively spliced CG1CE mRNA where the protein has the amino acid sequence shown in FIG. 5 as SEQ.ID.NO.:5.

Mutated forms of CG1CE proteins are intended to be within the scope of the present invention. In particular, mutated forms of SEQ.ID.NOs.:3 and 5 that give rise to Best's macular dystrophy are within the scope of the present invention. Accordingly, the present invention includes a protein having the amino acid sequence shown in FIG. 3 as SEQ.ID.NO.:3 except that the amino acid at position 93 is cysteine rather than tryptophan. The present invention also includes a protein having the amino acid sequence shown in FIG. 5 as SEQ.ID.NO.:5 except that the amino acid at position 93 is cysteine rather than tryptophan. The present invention includes a protein having the amino acid sequence shown in FIG. 3 as SEQ.ID.NO.:3 except that the amino acid at position 93 is not tryptophan. The present invention also includes a protein having the amino acid sequence shown in FIG. 5 as SEQ.ID.NO.:5 except that the amino acid at position 93 is not tryptophan.

The present invention includes a protein having the amino acid sequence shown in FIG. 3 as SEQ.ID.NO.:3 except that the amino acid at position 85 is histidine rather than tyrosine. The present invention also includes a protein having the amino acid sequence shown in FIG. 5 as SEQ.ID.NO.:5 except that the amino acid at position 85 is histidine rather than tyrosine. The present invention includes a protein having the amino acid sequence shown in FIG. 3 as SEQ.ID.NO.:3 except that the amino acid at position 85 is not tyrosine. The present invention also includes a protein having the amino acid sequence shown in FIG. 5 as SEQ.ID.NO.:5 except that the amino acid at position 85 is not tyrosine.

The present invention includes a protein having the amino acid sequence shown in FIG. 3 as SEQ.ID.NO.:3 except that the amino acid at position 6 is proline rather than threonine. The present invention also includes a protein having the amino acid sequence shown in FIG. 5 as SEQ.ID.NO.:5 except that the amino acid at position 6 is proline rather than threonine. The present invention includes a protein having the amino acid sequence shown in FIG. 3 as SEQ.ID.NO.:3 except that the amino acid at position 6 is not threonine. The present invention also includes a protein having the amino acid sequence shown in FIG. 5 as SEQ.ID.NO.:5 except that the amino acid at position 6 is not threonine.

The present invention includes a protein having the amino acid sequence shown in FIG. 3 as SEQ.ID.NO.:3 except that the amino acid at position 227 is asparagine rather than tyrosine. The present invention also includes a protein having the amino acid sequence shown in FIG. 5 as SEQ.ID.NO.:5 except that the amino acid at position 227 is asparagine rather than tyrosine. The present invention includes a protein having the amino acid sequence shown in FIG. 3 as SEQ.ID.NO.:3 except that the amino acid at position 227 is not tyrosine. The present invention also includes a protein having the amino acid sequence shown in FIG. 5 as SEQ.ID.NO.:5 except that the amino acid at position 227 is not tyrosine.

The present invention includes a protein having the amino acid sequence shown in FIG. 3 as SEQ.ID.NO.:3 except that the amino acid at position 299 is glutamate rather than glycine. The present invention includes a protein having the amino acid sequence shown in FIG. 3 as SEQ.ID.NO.:3 except that the amino acid at position 299 is not glycine. As with many proteins, it is possible to modify many of the amino acids of CG1CE and still retain substantially the same biological activity as the original protein. Thus, the present invention includes modified CG1CE proteins which have amino acid deletions, additions, or substitutions but that still retain substantially the same biological activity as CG1CE. It is generally accepted that single amino acid substitutions do not usually alter the biological activity of a protein (see, e.g., *Molecular Biology of the Gene*, Watson et al., 1987, Fourth Ed., The Benjamin/Cummings Publishing Co., Inc., page 226; and Cunningham & Wells, 1989, Science 244: 1081–1085). Accordingly, the present invention includes polypeptides where one amino acid substitution has been made in SEQ.ID.NOs.:3 or 5 wherein the polypeptides still retain substantially the same biological activity as CG1CE. The present invention also includes polypeptides where two amino acid substitutions have been made in SEQ.ID.NOs.:3 or 5 wherein the polypeptides still retain substantially the same biological activity as CG1CE. In particular, the present invention includes embodiments where the above-described substitutions are conservative substitutions. In particular, the present invention includes embodiments where the above-described substitutions do not occur in positions where the amino acid present in CG1CE is also present in one of the *C. elegans* proteins whose partial sequence is shown in FIG. 7.

FIG. 7 depicts partial amino acid sequences corresponding to positions 76–105 relative to human CG1CE as shown in SEQ ID NO: 3, now SEQ ID NO: 32. SEQ ID NOs 33–48 depict the amino acid substitutions at position 85 and 93 relative to SEQ ID NO: 32 in at least 16 different species of *C. elegans*. Each of the 16 different amino acid sequences depicted in each of SEQ ID NOs: 33–48 correspond to the same position 76–105 relative to the human fragment shown in SEQ ID NO: 32. For example, with the exception of SEQ ID NO: 37, tryptophan is fairly conserved in that it occupies the same position in SEQ ID NO: 32 when compared to 15 of the 16 species of *C. elegans*. More, the amino acid at position 85 in SEQ ID NO: 32 is also very well conserved in that that all of the sequences, i.e., SEQ ID NOs: 33–48 depict the same amino acid at the same position relative to the human fragment (SEQ ID NO: 32).

The CG1CE proteins of the present invention may contain post-translational modifications, e.g., covalently linked carbohydrate.

The present invention also includes chimeric CG1CE proteins. Chimeric CG1CE proteins consist of a contiguous polypeptide sequence of at least a portion of a CG1CE protein fused to a polypeptide sequence of a non-CG1CE protein.

The present invention also includes isolated forms of CG1CE proteins and CG1CE DNA. By "isolated CG1CE protein" or "isolated CG1CE DNA" is meant CG1CE protein or DNA encoding CG1CE protein that has been isolated from a natural source. Use of the term "isolated" indicates that CG1CE protein or CG1CE DNA has been removed from its normal cellular environment. Thus, an isolated CG1CE protein may be in a cell-free solution or placed in a different cellular environment from that in which it occurs naturally. The term isolated does not imply that an isolated CG1CE protein is the only protein present, but instead means that an isolated CG1CE protein is at least 95% free of non-amino acid material (e.g., nucleic acids, lipids, carbohydrates) naturally associated with the CG1CE protein. Thus, a CG1CE protein that is expressed in bacteria or even in eukaryotic cells which do not naturally (i.e., without human intervention) express it through recombinant means is an "isolated CG1CE protein."

A cDNA fragment encoding full-length CG1CE can be isolated from a human retinal cell cDNA library by using the polymerase chain reaction (PCR) employing suitable primer pairs. Such primer pairs can be selected based upon the cDNA sequence for CG1CE shown in FIG. 2 as SEQ.ID.NO.:2 or in FIG. 4 as SEQ.ID.NO.:4. Suitable primer pairs would be, e.g.:

CAGGGAGTCCCACCAGCC (SEQ.ID.NO.:6) and TCCCCATTAGGAAGCAGG (SEQ.ID.NO.:7) for SEQ.ID.NO.:2; and
CAGGGAGTCCCACCAGCC (SEQ.ID.NO.:6) and TCTCCTCTTTGTTCAGGC (SEQ.ID.NO.:8) for SEQ.ID.NO.:4.

PCR reactions can be carried out with a variety of thermostable enzymes including but not limited to AmpliTaq, AmpliTaq Gold, or Vent polymerase. For AmpliTaq, reactions can be carried out in 10 mM Tris-Cl, pH 8.3, 2.0 mM MgCl$_2$, 200 $\mu$M for each dNTP, 50 mM KCl, 0.2 $\mu$M for each primer, 10 ng of DNA template, 0.05 units/$\mu$l of AmpliTaq. The reactions are heated at 95° C. for 3 minutes and then cycled 35 times using the cycling parameters of 95° C., 20 seconds, 62° C., 20 seconds, 72° C., 3 minutes. In addition to these conditions, a variety of suitable PCR protocols can be found in *PCR Primer, A Laboratory Manual*, edited by C. W. Dieffenbach and G. S. Dveksler, 1995, Cold Spring Harbor Laboratory Press; or *PCR Protocols: A Guide to Methods and Applications*, Michael et al., eds., 1990, Academic Press.

A suitable cDNA library from which a clone encoding CG1CE can be isolated would be Human Retina 5'-stretch cDNA library in lambda gt10 or lambda gt11 vectors (catalog numbers HL1143a and HL1132b, Clontech, Palo Alto, Calif.). The primary clones of such a library can be subdivided into pools with each pool containing approximately 20,000 clones and each pool can be amplified separately.

By this method, a cDNA fragment encoding an open reading frame of 585 amino acids (SEQ.ID.NO.:3) or an open reading frame of 435 amino acids (SEQ.ID.NO.:5) can be obtained. This cDNA fragment can be cloned into a suitable cloning vector or expression vector. For example, the fragment can be cloned into the mammalian expression vector pcDNA3.1 (Invitrogen, San Diego, Calif.). CG1CE protein can then be produced by transferring an expression vector encoding CG1CE or portions thereof into a suitable host cell and growing the host cell under appropriate conditions. CG1CE protein can then be isolated by methods well known in the art.

As an alternative to the above-described PCR method, a cDNA clone encoding CG1CE can be isolated from a cDNA library using as a probe oligonucleotides specific for CG1CE and methods well known in the art for screening cDNA libraries with oligonucleotide probes. Such methods are described in, e.g., Sambrook et al., 1989, *Molecular Cloning: A Laboratory Manual*; Cold Spring Harbor Laboratory, Cold Spring Harbor, N.Y.; Glover, D. M. (ed.), 1985, *DNA Cloning: A Practical Approach*, MRL Press, Ltd., Oxford, U.K., Vol. I, II. Oligonucleotides that are specific for CG1CE and that can be used to screen cDNA libraries can be readily designed based upon the cDNA sequence of CG1CE shown in FIG. 2 as SEQ.ID.NO.:2 or in FIG. 4 as SEQ.ID.NO.:4 and can be synthesized by methods well-known in the art.

Genomic clones containing the CG1CE gene can be obtained from commercially available human PAC or BAC libraries available from Research Genetics, Huntsville, Ala. PAC clones containing the CG1CE gene (e.g., PAC 759J 12, PAC 466A11) are commercially available from Research Genetics, Huntsville, Ala. (Catalog number for individual PAC clones is RPCI.C). Alternatively, one may prepare genomic libraries, especially in P1 artificial chromosome vectors, from which genomic clones containing the CG1CE can be isolated, using probes based upon the CG1CE sequences disclosed herein. Methods of preparing such libraries are known in the art (Ioannou et al., 1994, Nature Genet. 6:84–89).

The novel DNA sequences of the present invention can be used in various diagnostic methods relating to Best's macular dystrophy. The present invention provides diagnostic methods for determining whether a patient carries a mutation in the CG1CE gene that predisposes that patient toward the development of Best's macular dystrophy. In broad terms, such methods comprise determining the DNA sequence of a region of the CG1CE gene from the patient and comparing that sequence to the sequence from the corresponding region of the CG1CE gene from a normal person, i.e., a person who does not suffer from Best's macular dystrophy.

Such methods of diagnosis may be carried out in a variety of ways. For example, one embodiment comprises:
- (a) providing PCR primers from a region of the CG1CE gene where it is suspected that a patient harbors a mutation in the CG1CE gene;
- (b) performing PCR on a DNA sample from the patient to produce a PCR fragment from the patient;
- (c) performing PCR on a control DNA sample having a nucleotide sequence selected from the group consisting of SEQ.ID.NOs.: 1, 2 and SEQ.ID.NO.:4 to produce a control PCR fragment;
- (d) determining the nucleotide sequence of the PCR fragment from the patient and the nucleotide sequence of the control PCR fragment;
- (e) comparing the nucleotide sequence of the PCR fragment from the patient to the nucleotide sequence of the control PCR fragment;
- where a difference between the nucleotide sequence of the PCR fragment from the patient and the nucleotide sequence of the control PCR fragment indicates that the patient has a mutation in the CG1CE gene.

In a particular embodiment, the PCR primers are from the coding region of the CG1CE gene, i.e., from the coding region of SEQ. ID. NOs.: 1, 2, or 4.

In a particular embodiment, the DNA sample from the patient is cDNA that has been prepared from an RNA sample from the patient. In another embodiment, the DNA sample from the patient is genomic DNA.

In a particular embodiment, the nucleotide sequences of the PCR fragment from the patient and the control PCR fragment are determined by DNA sequencing.

In a particular embodiment, the nucleotide sequences of the PCR fragment from the patient and the control PCR fragment are compared by direct comparison after DNA sequencing. In another embodiment, the comparison is made by a process that includes hybridizing the PCR fragment from the patient and the control PCR fragment and then using an endonuclease that cleaves at any mismatched positions in the hybrid but does not cleave the hybrid if the two fragments match perfectly. Such an endonuclease is, e.g., S1. In this embodiment, the conversion of the PCR fragment from the patient to smaller fragments after endonuclease treatment indicates that the patient carries a mutation in the CG1CE gene. In such embodiments, it may be advantageous to label (radioactively, enzymatically, immunologically, etc.) the PCR fragment from the patient or the control PCR fragment.

The present invention provides a method of diagnosing whether a patient carries a mutation in the CG1CE gene that comprises:
- (a) obtaining an RNA sample from the patient;
- (b) performing reverse transcription-PCR (RT-PCR) on the RNA sample using primers that span a region of the coding sequence of the CG1CE gene to produce a PCR fragment from the patient where the PCR fragment from the patient has a defined length, the length being dependent upon the identity of the primers that were used in the RT-PCR;
- (c) hybridizing the PCR fragment to DNA having a sequence selected from the group consisting of SEQ. ID. NOs.: 1, 2 and SEQ.ID.NO.:4 to form a hybrid;
- (d) treating the hybrid produced in step (c) with an endonuclease that cleaves at any mismatched positions in the hybrid but does not cleave the hybrid if the two fragments match perfectly;
- (e) determining whether the endonuclease cleaved the hybrid by determining the length of the PCR fragment from the patient after endonuclease treatment where a reduction in the length of the PCR fragment from the patient after endonuclease treatment indicates that the patient carries a mutation in the CG1CE gene.

The present invention provides a method of diagnosing whether a patient carries a mutation in the CG1CE gene that comprises:
- (a) making cDNA from an RNA sample from the patient;
- (b) providing a set of PCR primers based upon SEQ.ID.NO.:2 or SEQ.ID.NO.:4;
- (c) performing PCR on the cDNA to produce a PCR fragment from the patient;
- (d) determining the nucleotide sequence of the PCR fragment from the patient;
- (e) comparing the nucleotide sequence of the PCR fragment from the patient with the nucleotide sequence of SEQ.ID.NO.:2 or SEQ.ID.NO.:4;
- where a difference between the nucleotide sequence of the PCR fragment from the patient with the nucleotide sequence of SEQ.ID.NO.:2 or SEQ.ID.NO.:4 indicates that the patient carries a mutation in the CG1CE gene.

The present invention provides a method of diagnosing whether a patient carries a mutation in the CG1CE gene that comprises:
- (a) preparing genomic DNA from the patient;
- (b) providing a set of PCR primers based upon SEQ.ID.NO.:1, SEQ.ID.NO.:2, or SEQ.ID.NO.:4;
- (c) performing PCR on the genomic DNA to produce a PCR fragment from the patient;
- (d) determining the nucleotide sequence of the PCR fragment from the patient;
- (e) comparing the nucleotide sequence of the PCR fragment from the patient with the nucleotide sequence of SEQ.ID.NO.:2 or SEQ.ID.NO.:4;
- where a difference between the nucleotide sequence of the PCR fragment from the patient with the nucleotide sequence of SEQ.ID.NO.:2 or SEQ.ID.NO.:4 indicates that the patient carries a mutation in the CG1CE gene.

In a particular embodiment, the primers are selected so that they amplify a portion of SEQ.ID.NOs.:2 or 4 that includes at least one position selected from the group consisting of: positions 120, 121, 122, 357, 358, 359, 381, 382, 383, 783, 784, and 785. In another embodiment, the primers are selected so that they amplify a portion of SEQ.ID.NOs.:2 or 4 that includes at least one position selected from the group consisting of: positions 384, 385, and 386. In another embodiment, the primers are selected so that they amplify a portion of SEQ.ID.NO.:2 that includes at least one position selected from the group consisting of: positions 999, 1,000, and 1,001. In another embodiment, the primers are selected so that they amplify a portion of SEQ.ID.NOs.:2 or 4 that includes at least one codon that encodes an amino acid present in CG1CE that is also present in the corresponding position in at least one of the C. elegans proteins whose partial amino acid sequence is shown in FIG. 7.

In a particular embodiment, the present invention provides a diagnostic method for determining whether a person carries a mutation of the CG1CE gene in which the G at position 383 of SEQ.ID.NO.:2 has been changed to a C. This change results in the creation of a Fnu4HI restriction site. By amplifying a PCR fragment spanning position 383 of SEQ.ID.NO.:2 from DNA or cDNA prepared from a person, digesting the PCR fragment with Fnu4HI, and visualizing the digestion products, e.g., by SDS-PAGE, one can easily determine if the person carries the G383C mutation. For example, one could use the PCR primer pair 5'-CTCCTGC-CCAGGCTTCTAC-3' (SEQ.ID.NO.:30) and 5'-CT-TGCTCTGCCTTGCCTTC-3' (SEQ.ID.NO.:31) to amplify a 125 base pair fragment. Heterozygotes for the G383C mutation have three Fnu4HI digestion products: 125 bp, 85 bp, and 40 bp; homozygotes have two: 85 bp and 40 bp; and wild-type individuals have a single fragment of 125 bp.

In a particular embodiment, the present invention provides a diagnostic method for determining whether a person carries a mutation of the CG1CE gene in which the T at position 783 of SEQ.ID.NO.:2 has been changed to an A. This change results in the creation of a PflMI restriction site. By amplifying a PCR fragment spanning position 783 of SEQ.ID.NO.:2 from DNA or cDNA prepared from a person, digesting the PCR fragment with PflMI, and visualizing the digestion products, e.g., by SDS-PAGE, one can easily determine if the person carries the T783A mutation.

The present invention also provides oligonucleotide probes, based upon the sequences of SEQ.ID.NOs.: 1, 2, or 4, that can be used in diagnostic methods related to Best's macular dystrophy. In particular, the present invention includes DNA oligonucleotides comprising at least 18 contiguous nucleotides of at least one of a sequence selected from the group consisting of: SEQ.ID.NOs.: 1, 2 and SEQ.ID.:NO.4. Also provided by the present invention are corresponding RNA oligonucleotides. The DNA or RNA oligonucleotide probes can be packaged in kits.

In addition to the diagnostic utilities described above, the present invention makes possible the recombinant expression of the CG1CE protein in various cell types. Such recombinant expression makes possible the study of this protein so that its biochemical activity and its role in Best's macular dystrophy can be elucidated.

The present invention also makes possible the development of assays which measure the biological activity of the CG1CE protein. Such assays using recombinantly expressed CG1CE protein are especially of interest. Assays for CG1CE protein activity can be used to screen libraries of compounds or other sources of compounds to identify compounds that are activators or inhibitors of the activity of CG1CE protein. Such identified compounds can serve as "leads" for the development of pharmaceuticals that can be used to treat patients having Best's macular dystrophy. In versions of the above-described assays, mutant CG1CE proteins are used and inhibitors or activators of the activity of the mutant CG1CE proteins are discovered.

Such assays comprise:
(a) recombinantly expressing CG1CE protein or mutant CG1CE protein in a host cell;
(b) measuring the biological activity of CG1CE protein or mutant CG1CE protein in the presence and in the absence of a substance suspected of being an activator or an inhibitor of CG1CE protein or mutant CG1CE protein;
where a change in the biological activity of the CG1CE protein or the mutant CG1CE protein in the presence as compared to the absence of the substance indicates that the substance is an activator or an inhibitor of CG1CE protein or mutant CG1CE protein.

The present invention also includes antibodies to the CG1CE protein. Such antibodies may be polyclonal antibodies or monoclonal antibodies. The antibodies of the present invention are raised against the entire CG1CE protein or against suitable antigenic fragments of the protein that are coupled to suitable carriers, e.g., serum albumin or keyhole limpet hemocyanin, by methods well known in the art. Methods of identifying suitable antigenic fragments of a protein are known in the art. See, e.g., Hopp & Woods, 1981, Proc. Natl. Acad. Sci. USA 78:3824–3828; and Jameson & Wolf, 1988, CABIOS (Computer Applications in the Biosciences) 4:181–186.

For the production of polyclonal antibodies, CG1CE protein or an antigenic fragment, coupled to a suitable carrier, is injected on a periodic basis into an appropriate non-human host animal such as, e.g., rabbits, sheep, goats, rats, mice. The animals are bled periodically and sera obtained are tested for the presence of antibodies to the injected antigen. The injections can be intramuscular, intraperitoneal, subcutaneous, and the like, and can be accompanied with adjuvant.

For the production of monoclonal antibodies, CG1CE protein or an antigenic fragment, coupled to a suitable carrier, is injected into an appropriate non-human host animal as above for the production of polyclonal antibodies. In the case of monoclonal antibodies, the animal is generally a mouse. The animal's spleen cells are then immortalized, often by fusion with a myeloma cell, as described in Kohler & Milstein, 1975, Nature 256:495–497. For a fuller description of the production of monoclonal antibodies, see Antibodies: A Laboratory Manual, Harlow & Lane, eds., Cold Spring Harbor Laboratory Press, 1988.

Gene therapy may be used to introduce CG1CE polypeptides into the cells of target organs, e.g., the pigmented epithelium of the retina or other parts of the retina. Nucleotides encoding CG1CE polypeptides can be ligated into viral vectors which mediate transfer of the nucleotides by infection of recipient cells. Suitable viral vectors include retrovirus, adenovirus, adeno-associated virus, herpes virus, vaccinia virus, and polio virus based vectors. Alternatively, nucleotides encoding CG1CE polypeptides can be transferred into cells for gene therapy by non-viral techniques including receptor-mediated targeted transfer using ligand-nucleotide conjugates, lipofection, membrane fusion, or direct microinjection. These procedures and variations thereof are suitable for ex vivo as well as in vivo gene therapy. Gene therapy with CG1CE polypeptides will be particularly useful for the treatment of diseases where it is beneficial to elevate CG1CE activity.

The present invention includes DNA comprising nucleotides encoding mouse CG1CE. Included within such DNA is the DNA sequence shown in FIGS. 8A–C (SEQ. ID. NO.:28). Also included is DNA comprising positions 11–1, 663 of SEQ. ID. NO.:28. Also included are mutant versions of DNA encoding mouse CG1CE. Included is DNA comprising nucleotides that are identical to positions 11–1,663 of SEQ. ID. NO.:28 except that at least one of the nucleotides at positions 26–28, positions 263–265, positions 287–289, positions 689–691, and/or positions 905–907 differs from the corresponding nucleotide at positions 26–28, positions 263–265, positions 287–289, positions 689–691, and/or positions 905–907 of SEQ. ID. NO.:28. Particularly preferred versions of mutant DNAs are those in which the nucleotide change results in a change in the corresponding encoded amino acid. The DNA encoding mouse CG1CE can be in isolated form, can be substantially free from other nucleic acids, and/or can be recombinant DNA.

The present invention includes mouse CG1CE protein (SEQ. ID. NO.:29). This mouse CG1CE protein can be in isolated form and/or can be sustantially free from other proteins. Mutant versions of mouse CG1CE protein are also part of the present invention. Examples of such mutant mouse CG1CE proteins are proteins that are identical to SEQ. ID. NO.:29 except that the amino acid at position 6, position 85, position 93, position 227, and/or position 299 differs from the corresponding amino acid at position 6, position 85, position 93, position 227, and/or position 299 in SEQ. ID. NO.:29.

cDNA encoding mouse CG1CE can be amplified by PCR from cDNA libraries made from mouse eye or mouse testis. Suitable primers can be readily designed based upon SEQ. ID. NO.:28. Alternatively, cDNA encoding mouse CG1CE can be isolated from cDNA libraries made from mouse eye or mouse testis by the use of oligonucleotide probes based upon SEQ. ID. NO.:28.

Figure 10A:
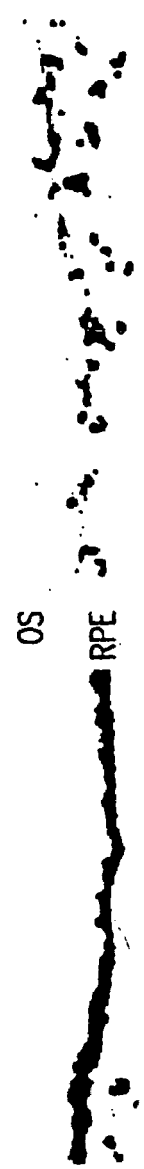
FIGS. 10A–C shows the results of in situ hybridization experiments demonstrating that mouse CG1CE mRNA expression is localized to the retinal pigmented epithelium cells (RPE).
Figure 10B:
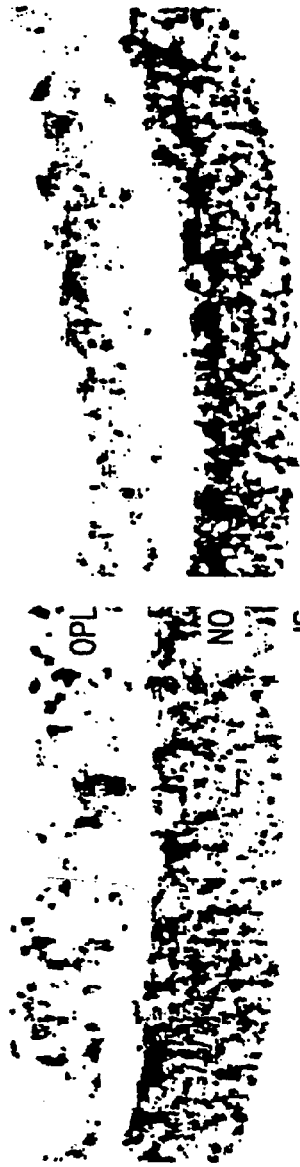
Figure 10C:

In situ hybridization studies demonstrated that mouse CG1CE is specifically expressed in the retinal pigmented epithelium (see FIG. 10).

By providing DNA encoding mouse CG1CE, the present invention allows for the generation of an animal model of Best's macular dystrophy. This animal model can be generated by making "knockout" or "knockin" mice containing altered CG1CE genes. Knockout mice can be generated in which portions of the mouse CG1CE gene have been deleted. Knockin mice can be generated in which mutations that have been shown to lead to Best's macular dystrophy when present in the human CG1CE gene are introduced into the mouse gene. In particular, mutations resulting in changes in amino acids 6, 85, 93, 227, or 299 of the mouse CG1CE protein (SEQ.ID.NO.:29) are contemplated. Such knockout and knockin mice will be valuable tools in the study of the Best's macular dystrophy disease process and will provide important model systems in which to test potential pharmaceuticals or treatments for Best's macular dystrophy.

Methods of producing knockout and knockin mice are well known in the art. For example, the use of gene-targeted ES cells in the generation of gene-targeted transgenic knockout mice is described in, e.g., Thomas et al., 1987, Cell 51:503–512, and is reviewed elsewhere (Frohman et al., 1989, Cell 56:145–147; Capecchi, 1989, Trends in Genet. 5:70–76; Baribault et al., 1989, Mol. Biol. Med. 6:481–492).

Techniques are available to inactivate or alter any genetic region to virtually any mutation desired by using targeted homologous recombination to insert specific changes into chromosomal genes. Generally, use is made of a "targeting vector," i.e., a plasmid containing part of the genetic region it is desired to mutate. By virtue of the homology between this part of the genetic region on the plasmid and the corresponding genetic region on the chromosome, homologous recombination can be used to insert the plasmid into the genetic region, thus disrupting the genetic region. Usually, the targeting vector contains a selectable marker gene as well.

In comparison with homologous extrachromosomal recombination, which occurs at frequencies approaching 100%, homologous plasmid-chromosome recombination was originally reported to only be detected at frequencies between $10^{-6}$ and $10^{-3}$ (Lin et al., 1985, Proc. Natl. Acad. Sci. USA 82:1391–1395; Smithies et al., 1985, Nature 317: 230–234; Thomas et al., 1986, Cell 44:419–428). Nonhomologous plasmid-chromosome interactions are more frequent, occurring at levels $10^5$-fold (Lin et al., 1985, Proc. Natl. Acad. Sci. USA 82:1391–1395) to $10^2$-fold (Thomas et al., 1986, Cell 44:419–428) greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening individual clones (Kim et al., 1988, Nucleic Acids Res. 16:8887–8903; Kim et al., 1991, Gene 103:227–233). Alternatively, a positive genetic selection approach has been developed in which a marker gene is constructed which will only be active if homologous insertion occurs, allowing these recombinants to be selected directly (Sedivy et al., 1989, Proc. Natl. Acad. Sci. USA 86:227–231). One of the most powerful approaches developed for selecting homologous recombinants is the positive-negative selection (PNS) method developed for genes for which no direct selection of the alteration exists (Mansour et al., 1988, Nature 336: 348–352; Capecchi, 1989, Science 244:1288–1292; Capecchi, 1989, Trends in Genet. 5:70–76). The PNS method is more efficient for targeting genes which are not expressed at high levels because the marker gene has its own promoter. Nonhomologous recombinants are selected against by using the Herpes Simplex virus thymidine kinase (HSV-TK) gene and selecting against its nonhomologous insertion with herpes drugs such as gancyclovir (GANC) or FIAU (1-(2-deoxy 2-fluoro-B-D-arabinofluranosyl)-5-iodouracil). By this counter-selection, the percentage of homologous recombinants in the surviving transformants can be increased.

The following non-limiting examples are presented to better illustrate the invention.

EXAMPLE 1

Identification of the Human CG1CE Gene and cDNA Cloning

Construction of Libraries for Shotgun Sequencing

Bacterial strains containing the BMD PACs (P1 Artificial Chromosomes) were received from Research Genetics (Huntsville, Ala.). The minimum tiling path between markers D11S4076 and UGB that represents the minimum genetic region containing the BMD gene includes the following nine PAC clones: 363M5 (140 kb), 519013(120 kb), 527E4 (150 kb), 688P12 (140 kb), 741N15 (170 kb), 756B9 (120 kb), 759J12 (140 kb), 1079D9 (170 kb), and 363P2 (160 kb). Cells were streaked on Luria-Bertani (LB) agar plates supplemented with the appropriate antibiotic. A single colony was picked up and subjected to colony-PCR analysis with corresponding STS primers described in Cooper et al., 1997, Genomics 41:185–192 to confirm the authenticity of PAC clones. A single positive colony was used to prepare a 5-ml starter culture and then 1-L overnight culture in LB medium. The cells were pelleted by centrifugation and PAC DNA was purified by equilibrium centrifugation in cesium chloride-ethidium bromide gradient (Sambrook, Fritsch, and Maniatis, 1989, *Molecular Cloning: A Laboratory Manual*, second edition, Cold Spring Harbor Laboratory Press). Purified PAC DNA was brought to 50 mM Tris pH 8.0, 15 mM MgCl$_2$, and 25% glycerol in a volume of 2 ml and placed in a AERO-MIST nebulizer (CIS-US, Bedford, Mass.). The nebulizer was attached to a nitrogen gas source and the DNA was randomly sheared at 10 psi for 30 sec. The sheared DNA was ethanol precipitated and resuspended in TE (10 mM Tris, 1 mM EDTA). The ends were made blunt by treatment with Mung Bean Nuclease (Promega, Madison, Wis.) at 30° C. for 30 min, followed by phenol/chloroform extraction, and treatment with T4 DNA polymerase (GIBCO/BRL, Gaithersburg, Md.) in multicore buffer (Promega, Madison, Wis.) in the presence of 40 uM dNTPs at 16° C. To facilitate subcloning of the DNA fragments, BstX I adapters (Invitrogen, Carlsbad, Calif.) were ligated to the fragments at 14° C. overnight with T4 DNA ligase (Promega, Madison, Wis.). Adapters and DNA fragments less than 500 bp were removed by column chromatography using a cDNA sizing column (GIBCO/BRL, Gaithersburg, Md.) according to the instructions provided by the manufacturer. Fractions containing DNA greater than 1 kb were pooled and concentrated by ethanol precipitation. The DNA fragments containing BstX I adapters were ligated into the BstX I sites of pSHOT II which was constructed by subcloning the BstX I sites from pcDNA II (Invitrogen, Carlsbad, Calif.) into the BssH II sites of pBlueScript (Stratagene, La Jolla, Calif.). pSHOT II was prepared by digestion with BstX I restriction endonuclease and purified by agarose gel electrophoresis. The gel purified vector DNA was extracted from the agarose by following the Prep-A-Gene (BioRad, Richmond, Calif.) protocol. To reduce ligation of the vector to itself, the digested vector was treated with calf intestinal phosphatase (GIBCO/BRL, Gaithersburg, Md. Ligation reactions of the DNA fragments with the cloning vector were transformed into ultra-competent XL-2 Blue cells (Stratagene, La Jolla, Calif.), and plated on LB agar plates supplemented with 100 µg/ml ampicillin. Individual colonies were picked into a 96 well plate containing 100 µl/well of LB broth supplemented with ampicillin and grown overnight at 37° C. Approximately 25 µl of 80% sterile glycerol was added to each well and the cultures stored at –80° C.

Preparation of Plasmid DNA

Glycerol stocks were used to inoculate 5 ml of LB broth supplemented with 100 µg/ml ampicillin either manually or by using a Tecan Genesis RSP 150 robot (Tecan AG, Hombrechtikon, Switzerland) programmed to inoculate 96 tubes containing 5 ml broth from the 96 wells. The cultures were grown overnight at 37° C. with shaking to provide aeration. Bacterial cells were pelleted by centrifugation, the supernatant decanted, and the cell pellet stored at –20° C. Plasmid DNA was prepared with a QIAGEN Bio Robot 9600 (QIAGEN, Chatsworth, Calif.) according to the Qiawell Ultra protocol. To test the frequency and size of inserts, plasmid DNA was digested with the restriction endonuclease Pvu II. The size of the restriction endonuclease products was examined by agarose gel electrophoresis with the average insert size being 1 to 2 kb.

DNA Sequence Analysis of Shotgun Clones

DNA sequence analysis was performed using the ABI PRISM™ dye terminator cycle sequencing ready reaction kit with AmpliTaq DNA polymerase, FS (Perkin Elmer, Norwalk, Conn.). DNA sequence analysis was performed with M13 forward and reverse primers. Following amplification in a Perkin-Elmer 9600, the extension products were purified and analyzed on an ABI PRISM 377 automated sequencer (Perkin Elmer, Norwalk, Conn.). Approximately 4 sequencing reactions were performed per kb of DNA to be examined (384 sequencing reactions per each of nine PACs).

Assembly of DNA Sequences

Phred/Phrap was used for DNA sequences assembly. This program was developed by Dr. Phil Green and licensed from the University of Washington (Seattle, Wash.). Phred/Phrap consists of the following programs: Phred for base-calling, Phrap for sequence assembly, Crossmatch for sequence comparisons, Consed and Phrapview for visualization of data, Repeatmasker for screening repetitive sequences. Vector and *E. coli* DNA sequences were identified by Crossmatch and removed from the DNA sequence assembly process. DNA sequence assembly was on a SUN Enterprise 4000 server running a Solaris 2.51 operating system (Sun Microsystems Inc., Mountain View, Calif.) using default Phrap parameters. The sequence assemblies were further analyzed using Consed and Phrapview.

Identification of New Microsatellite Genetic Markers from the Best's Macular Dystrophy Region Isolation of CA microsatellites from PAC-specific sublibraries, Southern blotting and hybridization of PAC DNA with a $(dC-dA)_n$ $(dG-dT)_n$ probe (Pharmacia Biotech, Uppsala, Sweden) was used to confirm the presence of CA repeats in nine PAC clones that represent a minimum tiling path. Shotgun PAC-specific sublibraries were constructed from DNA of all 9 PAC clones using a protocol described above. The sublibraries were plated on agar plates, and colonies were transfered to nylon membranes and probed with randomly primed polynucleotide, $(dC-dA)_n$ $(dG-dT)_n$, Hybridization was performed overnight in a solution containing 6× SSC, 20 mM sodium phosphate buffer (pH 7.0), 1% bovine serum albumin, and 0,2% sodium dodecyl sulfate at 65° C. Filters were washed four times for 15 min each in 2× SSC and 0.2% SDS at 65° C. CA-positive subclones were identified for all but one PAC clone (527E4). DNA from these subclones was isolated and sequenced as descrobed above for the shotgun library clones.

Identification of simple repeat sequences in assembled DNA sequences. DNA sequence at the final stage of assembly was checked for the presence of microsatellite repeats using a Consed visualization tool of the Phred/Phrap package.

Polymorphism Analysis and Recombination Mapping

Sequence fragments containing CA repeats were analyzed using the PRIMER program; oligonucleotide pairs flanking each of the CA repeats were synthesized. The forward primer was kinase-labeled with [gamma-$^{32}$P]-ATP. Amplification of the genomic DNA was peformed in a total volume of 10 µl containing 5 ng/µg of genomic DNA; 10 mM Tris-HCl pH 8.3; 1.5 mM MgCl$_2$; 50 mMKCl; 0.01% gelatin; 200 µM dNTPs; 0.2 pmol/µL of both primers; 0.025 unit/µl of Taq polymerase. The PCR program consisted of 94° C. for 3 min followed by 30 cycles of 94° C. for 1 min, 55° C. for 2 min, 72° C. for 2 min and a final elongation step at 72° C. for 10 min. Following amplification, samples were mixed with 2 vol of a formamide dye solution and run on a 6% polyacrylamide sequencing gel. Two newly identified markers detected two recombination events in disease chromosomes of individuals from family S1. This limited the minimum genetic region to the interval covered by 6 PAC clones: 519O13, 759J12, 756B9, 363M5, 363P2, and 741N15.

Identification of the Retina-Specific EST Hit in the pCA759112-2 Clone.

A CA-positive subclone (pCA759J12-2) was identified in the shotgun library generated from the PAC 759j12 DNA by hybridization to the (dC-dA)$_n$ (dG-dT)$_n$ probe. DNA sequence from pCA759J12-2 was queried against the EST sequences in the GenBank database using the BLAST algorithm (S.F. Altschul, et al., 1990, J. Mol. Biol. 215:403–410). The BLAST analysis identified a high degree of similarity between the DNA sequence obtained from the clone pCA759J12-2 and a retina-specific human EST with GenBank accession number AA318352. BLASTX analysis of EST AA318352 revealed a strong homology of the corresponding protein to a group of C. elegans proteins with unknown function (RFP family). The RFP family is known only from C. elegans genome and EST sequences (e.g., C. elegans C29F4.2 and B0564.3) and is named for the amino acid sequence RFP that is invariant among 15 of the 16 family members; members share a conserved 300–400 amino acid sequence including 25 highly conserved aromatic residues.

A human gene partially represented in pCA759J12-2 and EST AA318352 was dubbed CG1CE (Candidate Gene #1 with the homology to the C. elegans group of genes) and selected for detaled analysis.

BioInformatic Analysis of Assembled DNA Sequences

When the assembled DNA sequences from the nine BMD PACs approached 0.5–1-fold coverage, the DNA contigs were randomly concatenated, and prediction abilities of the program package AceDB were utilized to aid in gene identification.

In addition to the DNA sequence generated from the nine PACs mentioned above, Genbank database entries for PACs 466A11 and 363P2 (GeneBank accession numbers AC003025 and AC003023, respectively) were analyzed with the use of the same AceDB package. PAC clones 466A11 and 363P2 represent parts of the PAC contig across the BMD region (Cooper et al., 1997, Genomics 41:185–192); both clones map to the minimum genetic region containing the BMD gene that was determined by recombination breakpoint analysis in a 12-generation Swedish pedigree (Graff et al., 1997, Hum. Genet. 101: 263–279). Datbase entries for PACs 466A11 and 363P2 represent unordered DNA pieces genereated in Phase 1 High Throughput Genome Sequence Project (HTGS phase 1) by Genome Science and Technology Center, University of Texas Southwestern Medical Center at Dallas.

cDNA Sequence and Exon/Intron Organization of the CG1CE Gene

Genomic DNA sequences from PACs 466A11 and 759J12 were compared with the CG1CE cDNA sequence from EST AA318352 using the program Crossmatch which allowed for a rapid and sensitive detection of the location of exons. The identification of intron/exon boundaries was then accomplished by manually comparing visualized genomic and cDNA sequences by using the AceDB package. This analysis allowed the identification of exons 8, 9, and 10 that are represented in EST AA318352. To increase the accuracy of the analysis, the DNA sequence of EST AA318352 was verified by comparison with genomic sequence obtained from pCA759J12-2, PAC 466A11, and shotgun PAC 759J12 subclones. The verified EST AA318352 sequence was reanalyzed by BLAST; two new EST's (accession numbers AA307119 and AA205892) were found to partially overlap with EST AA318352. They were assembled into a contig using the program Sequencher (Perkin Elmer, Norwalk, Conn.), and a consensus sequence derived from three ESTs (AA318352, AA307119, and AA205892) was re-analyzed by BLAST. BLAST analysis identified a fourth EST belonging to this cluster (accession number AA317489); EST AA317489 was included in the consensus cDNA sequence. The consensus sequence derived from the four ESTs (AA318352, AA307119, AA205892, and AA317489) was compared with genomic sequences obtained from pCA759J12-2, PAC 466A11, and shotgun PAC 759J12 subclones using the programs Crossmatch and AceDB. This analysis verified the sequence and corrected sequencing errors that were found in AA318352, AA307119, AA205892, and AA317489. Comparison of cDNA and genomic sequences revealed a total of 7 exons. The order of the exons from 5' end to 3' end was 5'-ex4-ex5-ex6-ex8-ex9-ex10-ex11-3'. BLASTX analysis of the genomic segment located between exons 6 and 8 in PAC 466A11 revealed strong homology of the corresponding protein to a group of C. elegans proteins (RFP family). Since there were no EST hits in the GenBank EST database that covers this stretch of genomic sequence, this part of the CG1CE gene was called exH (Hypothetical ex 7). This finding changed the order of exons in the CG1CE gene to 5'-ex4-ex5-ex6-ex7-ex8-ex9-ex 10-ex11-3'. The BLAST analysis of the DNA region located upstream of the exon 4 identified an additional human EST (AA326727) with a high degree of similarity to genomic sequence. Comparison of DNA and genomic sequences revealed the presence of two additional exons (ex1 and ex2) in the CG1CE gene. This finding changed the order of the exons in the CG1CE gene to 5'-ex1-ex2-ex4-ex5-ex6-ex7-ex8-ex9-ex10-ex11-3'. Bioinformatic analysis did not allow the prediction of boudaries between exons 2 and 4, exons 6 and 7, and exons 7 and 8. In addition, there was no overlap between ESTs represented in exons 1 and 2 from one side and exons 4, 5, 6, 7, 8, 9, 10, and 11 from another. There was the possibility of the presence of additional exons in the CG1CE gene that were not represented in the GenBank EST database.

Identification of an Additional Exon and Determination of the Exact Exon/Intron Boundaries within the CG1CE Gene.

To identify additional exon(s) within the CG1CE gene and verify the exonic composition of this gene, forward and reverse PCR primers from all known exons of the CG1CE gene were synthesized and used to PCR amplify CG1CE cDNA fragments from human retina "Marathon-ready" cDNA (Clontech, Palo Alto, Calif.). In these RT-PCR experiments forward primer from ex1 (LF: CTAGTCGCCAGAC-CTTCTGTG) (SEQ.ID.NO.:9) was paired with a reverse primer from ex4 (GR: CTTGTAGACTGCGGTGCTGA) (SEQ.ID.NO.: 10), forward primer from ex4 (GF: GAAAG-CAAGGACGAGCAAAG) (SEQ.ID.NO.: 11) was paired with a reverse primer from ex6 (ER: AATCCAGTCGTAG-GCATACAGG) (SEQ.ID.NO.: 12), forward primer from ex6 (EF: ACCTTGCGTACTCAGTGTGGA) (SEQ.ID.NO.: 13) was paired with a reverse primer from ex8 (AR: TGTC-GACAATCCAGTTGGTCT) (SEQ.ID.NO.:14), forward primer from ex8 (AF: CCCTTTGGAGAGGATGATGA) (SEQ.ID.NO.: 15) was paired with a reverse primer from ex10 (CR: CTCTGGCATATCCGTCAGGT) (SEQ.ID.NO.: 16), forward primer from ex10 (CF: CTTCAAGTCTGC-CCCACTGT) (SEQ.ID.NO.: 17) was paired with a reverse primer from ex11 (DR: GCATCCCCATTAGGAAGCAG) (SEQ.ID.NO.: 18).

A 50 µl PCR reaction was performed using the Taq Gold DNA polymerase (Perkin Elmer, Norwalk, Conn.) in the reaction buffer supplied by the manufacturer with the addition of dNTPs, primers, and approximately 0.5 ng of human retina cDNA. PCR products were electrophoresed on a 2% agarose gel and DNA bands were excised, purified and subjected to sequence analysis with the same primers that were used for PCR amplification. The assembly of the DNA sequence results of these PCR products revealed that:

(i) exons 1 and 2 from one side and exons 4, 5, 6, 7, 8, 9, 10, and 11 indeed represent fragments of the same gene (ii) an additional exon is present between exons 2 and 4 (named ex3)

(iii) exon 7 (Hypothetical) predicted by the BLASTX analysis is present in the CG1CE cDNA fragment amplified by EF/AR primers.

Comparison of the DNA sequences obtained from RT-PCR fragments with genomic sequences obtained from pCA759J12-2, PAC 466A11, and shotgun PAC 759J12 subclones was performed using the programs Crossmatch and AceDB. This analysis confirmed the presence of the exons originally found in five ESTs (AA318352, AA307119, AA205892, AA317489, and AA326727) and identified an additional exon (exon3) in the CG1CE gene. Exact sequence of exon/intron boundaries within the CG1CE gene were determined for all of the exons. The splice signals in all introns conform to publish consensus sequences. The CG1CE gene appears to span at least 16 kb of genomic sequence. It contains a total of 11 exons.

Two Splice Donor Sites for Intron 7.

Two splicing variants of exon 7 were detected upon sequence analysis of RT-PCR products amplified from human retina cDNA with the primer pair EF/AR. Two variants utilize alternative splice donor sites separated from each other by 203 bp. Both splicing sites conform to the published consensus sequence.

Identification of 5' and 3' Ends of CG1CE cDNA

RACE is an established protocol for the analysis of cDNA ends. This procedure was performed using the Marathon RACE template from human retina, purchased from Clontech (Palo Alto, Calif.). cDNA primers KR (CTAAGCGGGCATTAGCCACT) (SEQ.ID.NO.:19) and LR(TGGGGTTCCAGGTGGGTCCGAT) (SEQ.ID.NO.:20) in combination with a cDNA adaptor primer API (CCATCCTAATACGACTCACTATAGGGC) (SEQ.ID.NO.:21) were used in 5'RACE. cDNA primer DF (GGATGAAGCACATTCCTAACCTGCTTC) (SEQ.ID.NO.:22) in combination with a cDNA adaptor primer API (CCATCCTAATACGACTCACTATAGGGC) (SEQ.ID.NO.:21) was used in 3'RACE. Products obtained from these PCR amplifications were analyzed on 2% agarose gels. Excised fragments from the gels were purified using Qiagen QIAquick spin columns and sequenced using ABI dye-terminator sequencing kits. The products were analyzed on ABI 377 sequencers according to standard protocols.

EXAMPLE 2

Best's Macular Dystrophy is Associated with Mutations in an Evolutionarily Conserved Region of CG1CE Genomic DNA from BMD patients from two Swedish pedigrees having Best's macular dystrophy (families S1 and SL76) was amplified by PCR using the following primer pair:

exG_left  AAAGCTGGAGGAGCCGAG   (SEQ.ID.NO.:23)

exG_right CTCCACCCATCTTCCGTTC  (SEQ.ID.NO.:24)

This primer pair amplifies a genomic fragment that is 412 bp long and contains exon4 and adjacent intronic regions.

The patients were:

Family S1:

S1-3, a normal individual, i.e., not having BMD; sister of S 1-4

S1-4, an individual heterozygous for BMD; and

S1-5, an individual homozygous for BMD.

Patients S1-4 and S1-5 had the clinical symptoms of BMD, including morphological changes observable upon ophthalmologic examination.

Family SL76:

SL76-3, an individual heterozygous for BMD; mother of SL76-2

SL76-2, an individual heterozygous for BMD, son of SL-3.

PCR products produced using the primer sets mentioned above were amplified in 50 µl reactions consisting of Perkin-Elmer 10×PCR Buffer, 200 mM dNTP's, 0.5 ul of Taq Gold (Perkin-Elmer Corp., Foster City, Calif.), 50 ng of patient DNA and 0.2 µM of forward and reverse primers. Cycling conditions were as follows:

1. 94° C. 10 min
2. 94° C. 30 sec
3. 72° C. 2 min (decrease this temperature by 1.1° C. per cycle)
4. 72° C. 2 min
5. Go to step 2 15 more times
6. 94° C. 30 sec
7. 55° C. 2 min
8. 72° C. 2 min
9. Go to step 6 24 more times
10. 72° C. 7 min
11. 4° C.

Products obtained from this PCR amplification were analyzed on 2% agarose gels and excised fragments from the gels were purified using Qiagen QIAquick spin columns and sequenced using ABI dye-terminator sequencing kits. The products were analyzed on ABI 377 sequencers according to standard protocols.

The results are shown in FIG. 6. FIG. 6 shows a chromatogram from sequencing runs on the PCR fragments from patients S1-3, S1-4, and S1-5. The six readings represent sequencing of both strands of the PCR fragments from the patients. As can be seen from FIG. 6, the two patients affected with BMD, patients S1-4 and S1-5, both carry a mutation at position 383 of SEQ.ID.NO.:2. Both copies of the CG1CE gene are mutated in homozygous affected S1-5, while heterozygous affected S1-4 contains both normal and mutated copies of the CG1CE gene. This mutation changes the codon that encodes the amino acid at position 93 of SEQ. ID. NO.:3 from TGG (encoding tryptophan) to TGC (encoding cysteine). Patient S1-3, a normal individual, has the wild-type sequence, TGG, at this codon. This disease mutation that changes this TGG codon to a TGC codon was not found upon sequencing of 50 normal unrelated individulas (100 chromosomes) of North American descent.

Both patients from family SL76 carry a mutation at position 357 of SEQ.ID.NO.:2. This mutation changes the codon that encodes the amino acid at position 85 of SEQ.ID.NO.:3 from TAC (encoding tyrosine) to CAC (encoding histidine). This disease mutation that changes this TAC codon to a CAC codon was not found upon sequencing of 50 normal unrelated individulas (100 chromosomes) of North American descent.

Amino acid positions 85 and 93 of the CG1CE protein are evolutionarily conserved. FIG. 7 demonstrates that position 93 is occupied by tryptophan not only in the CG1CE protein, but also in 15 of 16 related *C. elegans* proteins. The lone *C. elegans* protein in which this residue is not tryptophan contains an isofunctional phenylalanine instead. Phenylalanine and tryptophan, both being hydrophobic, aromatic amino acids, are highly similar. Position 85 is occupied by tyrosine and isofunctional phenylalanine in all 16 related *C. elegans* proteins. Phenylalanine and tyrosine, both being aromatic amino acids, are highly similar.

EXAMPLE 3

Expression of CG1CE

RT-PCR: RT-PCR experiments were performed on "quick-clone" human cDNA samples available from Clontech, Palo Alto, Calif. cDNA samples from heart, brain, placenta, lung, liver, skeletal muscle, kidney, pancreas, and retina were amplified with primers AF (CCCTTTG-GAGAGGATGATGA) (SEQ.ID.NO.:15) and CR (CTCTG-GCATATCCGTCAGGT) (SEQ.ID.NO.: 16) in the following PCR conditions:

| | |
|---|---|
| 1. | 94° C. 10 min |
| 2. | 94° C. 30 sec |
| 3. | 72° C. 2 min (decrease this temperature by 1.1° C. per cycle) |
| 4. | 72° C. 2 min |
| 5. | Go to step 2 15 more times |
| 6. | 94° C. 30 sec |
| 7. | 55° C. 2 min |
| 8. | 72° C. 2 min |
| 9. | Go to step 6 19 more times |
| 10. | 72° C. 7 min |
| 11. | 4° C. |

The CG1CE gene was found to be predominantly expressed in human retina and brain Northern blot analysis: Northern blots containing poly (A+)-RNA from different human tissues were purchased from Clontech, Palo Alto, Calif. Blot #1 contained human heart, brain placenta, lung, liver, skeletal muscle, kidney, and pancreas poly(A+)-RNA. Blot #2 contained stomach, thyroid, spinal cord, lymph node, trachea, adrenal gland, and bone marrow poly(A+)-RNA.

Primers CF (CTTCAAGTCTGCCCCACTGT) (SEQ.ID.NO.: 17) and exC_right (TAGGCTCAGAGCAAGG-GAAG) (SEQ.ID.NO.:25) were used to amplify a PCR product from total genomic DNA. This product was purified on an agarose gel, and used as a probe in Northern blot hybridization. The probe was labeled by random priming with the Amersham Rediprime kit (Arlington Heights, Ill.) in the presence of 50–100 µCi of 3000 Ci/mmole [alpha $^{32}$P]dCTP (Dupont/NEN, Boston, Mass.). Unincorporated nucleotides were removed with a ProbeQuant G-50 spin column (Pharmacia/Biotech, Piscataway, N.J.). The radiolabeled probe at a concentration of greater than $1 \times 10^6$ cpm/ml in rapid hybridization buffer (Clontech, Palo Alto, Calif.) was incubated overnight at 65° C. The blots were washed by two 15 min incubations in 2× SSC, 0.1% SDS (prepared from 20× SSC and 20% SDS stock solutions, Fisher, Pittsburgh, Pa.) at room temperature, followed by two 15 min incubations in 1× SSC, 0.1% SDS at room temperature, and two 30 min incubations in 0.1× SSC, 0.1% SDS at 60° C. Autoradiography of the blots was done to visualize the bands that specifically hybridized to the radiolabeled probe.

The probe hybridized to an mRNA transcript that is uniquely expressed in brain and spinal cord.

Mouse probe for the murine ortholog of the GC1CE gene was generated based on the sequence of an EST with GenBank accession number AA497726. The 246 bp probe was amplified from mouse heart cDNA (Clontech, Palo Alto, Calif.) using the primers mouseCG1CE_L (ACACAACA-CATTCTGGGTGC) (SEQ.ID.NO.:26) and mouseCG1CE_R (TTCAGAAACTGCTTCCCGAT) (SEQ.ID.NO.:27). Due to an extremely low expression level of the CG1CE gene in mouse heart, repetitive amplification steps were used to generate this probe. The authenticity of this probe was verified by sequence analysis of the gel purified DNA band. Northern blot containing poly(A+)-RNA from several rat tissues (heart, brain, spleen, lung, liver, skeletal muscle, kidney, testis) was purchase from Clontech, Palo Alto, Calif. The probe hybridized to an mRNA transcript that is expressed in testis only.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Various publications are cited herein, the disclosures of which are incorporated by reference in their entireties.

SEQUENCE LISTING

```
<160> NUMBER OF SEQ ID NOS: 48

<210> SEQ ID NO 1
<211> LENGTH: 16125
<212> TYPE: DNA
<213> ORGANISM: Homo Sapiens
<220> FEATURE:
<221> NAME/KEY: misc_feature
<222> LOCATION: (1)...(16125)
<223> OTHER INFORMATION: n = A,T,C or G
<220> FEATURE:
<221> NAME/KEY: misc_feature
<222> LOCATION: 2166, 2167, 2168, 2169, 2170, 2171, 2172, 2173, 2174,
      2175, 10444, 10445, 10446, 10447, 10448, 10449, 10450, 10451
<223> OTHER INFORMATION: n = A,T,C or G
```

-continued

```
<220> FEATURE:
<221> NAME/KEY: misc_feature
<222> LOCATION: 10452, 10453, 15338
<223> OTHER INFORMATION: n = A,T,C or G

<400> SEQUENCE: 1
ccaaaaaatt gttctcttgg gggttggggc gacaagcggg aagggagggc attttgggca        60
aattggctta ttgccacgca agggctttaa caccttaggt tggtgggttc acaggttgca       120
ggcaacccac catggcacac gtatacctat gtaaccaacc tgcaccatca tgtataccta       180
tgtaaccaac ctggtacatt ctgcacacgt atcccaggac tttagagtga aaaaaaaagt       240
ggtgtgtaga aaaatcacct gcaatctcag catagttaac gcttagtaca tttcagagag       300
agagggtgac aggaaaggga ggatgagagt gggtttaaga cacaaggtca tattataaaa       360
tcagggcttc tggaagttta gtcccaaaac cacacatctc ataatcccct gcagtgcttg       420
attaaaatgc aacatcccta aggccacaga ctcagactct ggagaaagat ccagaaaact       480
gcccgtttaa taaacatttg ggcgattctt acggcctcta aagaccaaga accactgctg       540
cctagagctc tgctctcttc attgaacaat acaagaggag tgtgtaggta gacacccacc       600
acttccaaca gcttaggaga gcccttgagt atggattgat gtattaaaat ttattgaatc       660
acatgctgag attttcacca gctgcccgtg gggatctggg catttattcc catattgcac       720
tggctggctg gaagccagca gcataaactc cagggctgtt ctgtcaaccc ccaccagact       780
cacccccctc caccagcccc ggcaggcttc tccttccatc tctctgaagc aacttactga       840
tgggccctgc cagccaatca cagccagaat aacgtatgat gtcaccagca gccaatcaga       900
gctcctcgtc agcatatgca gaattctgtc attttactag ggtgatgaaa ttcccaagca       960
acaccatcct tttcagataa gggcactgag gctgagagag gagctgaaac ctacccgggg      1020
tcaccacaca caggtggcaa ggctgggacc agaaaccagg actgttgact gcagcccggt      1080
attcattctt tccatagccc acagggctgt caaagacccc agggcctagt cagaggctcc      1140
tccttcctgg agagttcctg gcacagaagt tgaagctcag cacagccccc taaccccccaa     1200
ctctctctgc aaggcctcag gggtcagaac actggtggag cagatccttt agcctctgga      1260
ttttagggcc atggtagagg gggtgttgcc ctaaattcca gccctggtct cagcccaaca      1320
ccctccaaga agaaattaga ggggccatgg ccaggctgtg ctagccgttg cttctgagca      1380
gattacaaga agggactaag acaaggactc ctttgtggag gtcctggctt agggagtcaa      1440
gtgacggcgg ctcagcactc acgtgggcag tgccagcctc taagagtggg caggggcact      1500
ggccacagag tcccagggag tcccaccagc ctagtcgcca gaccttctgt gggatcatcg      1560
gacccacctg gaaccccacc tgtgagtaca aggtgcccca ggtggactgg gctgggcttt     1620
tgaggccttc agggttggat ggccatcttg cgtatttgtg tgggatatgc acacacaggc      1680
agcacatgcg caggtgtgtg ggcacctgtg tgtctgtgca aatgccctga ggtgggaatg      1740
agcttggtgt gcatcaggag cgacagccag ccagtgtggc tgcagcaaaa cacacaggga      1800
aagaatggag ggggcatcaa tcactgacaa aattatttat agagctcccc ctaaaaaaaa      1860
gaaggtctct tctttcgata gaagaaggga gagaggggt ttgtccttat aaatataagg       1920
gaggagccgc ccctcaaaaa ataagggagg gaggacccaa gaccccgtgg gttgtgtgtt      1980
ttccaggggg agctcgaacc ctttagaggg agcgtgggag aaccgctgta ttcaggcctc      2040
tcgagagaaa aggagcggcc gcccaaaaaa tatccctccc gggcgataag aaatggtggc      2100
ctctctcaaa aagatgaaga ggaagccgga gttgtatgtg ttgatatttt taaaactcca      2160
```

```
ggtagnnnnn nnnnntgctt cagtaaattt ttattgagcg ccttctacga gaacacaaga    2220
ggagcttcca ttctgaggag gaaacaggca ggaaacagga agatatcctg tataatttca    2280
agtagtgata agtgctctct agaaatatca agcaaggtga ggagacacag agcaccggtg    2340
gcagtgggc  tctatttcca ggttggatgg ttgggaacat cctttctaaa gggaacctgg    2400
agtgggaagg aaccatgcag gtatctcagg aagagcttcc tccaggcagg aagatcagca    2460
ggtggaaagg ccctggagcc accattcagt aaacatcatt tgagcatctc taccagctag    2520
gttccattat gggaatggga atatggtggt ggacagggct gcctggtccc ttccatactt    2580
ctcacactag ggtggttgag agagcttggg agctaacgaa caagatgggc tgagaacact    2640
gcctagccca gaggacctga gcttagtgtg tagacattgc tgctgttact gcctttgtcg    2700
ttgtattatt tatttattta tttattgatc ttaagacaga gttttgctct tcttacccag    2760
gcttgagtgc aatggcgtga tctcagctca ctgcaacctc cacctcctgg gatcaagcga    2820
ttctcctgcc tcagcctcct gagtagctgg gattacaggc acccgcacca cgcctggata    2880
atttttttgt attttagta gagacagggt ttcaccatgt tggccaggct ggtctcgaac    2940
tcctgacctt aggtgatcca cctgcctcga cttcccaaag tgctgggatt ataggcatga    3000
gccactgcgc ccagtgatta tagaaagtta aaggcacatg gcaatgcaca cgcctatcta    3060
cgtcttccct gccaaagcaa agggcagcct ctgggctcac tttcttgcgt ttctacttcc    3120
aaaaggcagt cagaactggc agggccttgg agaccacttc atccacctcc tagggtccct    3180
atgggagagt tgaggtccag agcagggaag ggtcctgaca ggctctgacc agggcctctg    3240
atccctacaa accccaatc ggtgtccctc tctaccagga cccaagccca cctgctgcag     3300
cccactgcct ggccatgacc atcacttaca caagccaagt ggctaatgcc cgcttaggct    3360
ccttctcccg cctgctgctg tgctggcggg gcagcatcta caagctgcta tatggcgagt    3420
tcctaatctt cctgctctgc tactacatca tccgctttat ttataggtaa agctggcagg    3480
gctgggccgg ggggcctggg aaggatgtgg ctggggctgg gagctgggag ctcctggggg    3540
cctcccagcc agctcaggc ccagtgcacc agtccactac aacactaagc tgggctcctg     3600
accagctcct gggcactgga gctgaggctg cgcgctgggg gctgggcaga gtaaagaagt    3660
cacactgaga ggctgctcaa gccaggccag cagggtttta gccacccttc ctccaacccc    3720
aggaggaccc ctggagccca ggctttgtct ggccccactc tactggcctg ttttactgaa    3780
tcccacacag actcataggc ccacatagta cattaaaaaa gagagagaga gagagagaga    3840
gagagagatg gagtctcact gtgttgtcca ggctggtctc gaactcctag gctcaagcaa    3900
tccccctgcc ttagcctccc aaggggctgg gattacaggt gtgagctact gcacttgacc    3960
aaccacatgg tacttttttt tttttttttt tttttgaga cagggtttca ctccatcacc    4020
caggctggag tgcagtgggg gcaatcttgg ctcactgtaa cctctgcctc ccaggtgcaa    4080
gcgattctcc tgccttagcc tcctgagtag ctggaattat aggcacacac caccacgcct    4140
ggctaatttt tttttttttc tgtattttta gtagagacag ggtttcatca tgttggccag    4200
gctggtcttg aaccctgac ctcaagtgat ccacccacct cggcctccca aagtgctggg     4260
attacaggtg tcagccacca tgcacagccc acatggtaca ttttttaaaa ttatttttta    4320
attaaaatgt ttatctaagg ccagtagcag tgactcgcgt ctgtaatccc agcactttga    4380
ggggccaagg tgcggggatc acttgagcct gggagttcag cgtgggcaac atagtgagac    4440
cccgtctcta ccaaaaattt aaaaaattag ctggagtggt tggcatttgc ctgtggtccc    4500
agctactgg gaagctgagg tgtggggatg gctgaagcct gtgaggtcga ggctgcagtg    4560
```

```
agctatgatc acaccactgc acttcagcct gagtgacagg ctatctcaaa agcaaacaaa    4620
ataatgttta tctaaacggt aaggtataat cacagaatat atgatagcat tttaaattga    4680
aaaagcatta atgattacat ggattgtaaa atatcaaata catgaaattc ttgtgttctt    4740
aataatgcta gcaacaaggc acatttggtt tttactaggg caccaaggta ctttaaaaaa    4800
agttagggcc agccacaggg gctcacacct gtaatcccag cactttggga ggccaaggca    4860
ggaggatcac ttgagcccag gagtttagga cctgagcaac atagggagat cctgatcttg    4920
tctctataaa aaattaaaaa attggctagg ccctttggct tacacccgta atcccagcac    4980
tttgggaggc cgaggcgggt ggatcatgag gtcaggagtt caagaccagc ctggccaaca    5040
tagtgaaccc aatctctact ataaatacaa aaattagccg agtggggtgg cacgcacctg    5100
tagttccagc tactcaggag gatgaggccg gagaatcgct tgagcccggg aggcagaggc    5160
tgcagtgagc cgagaccatg ccattgcact ccagcctagg tgacagagtg agactccgtc    5220
ttaaaataat attaaaatct taaatgatc tgggcatggt ggcttatgcc tgtagtccca    5280
cccagctctt caggaggctg aagcgggagg attgcttcag cccaggaggt tgaggctgca    5340
gtgagtcatg actgtgccgc tgcccttgag cctgggtaac agagcaagac cctatctcaa    5400
aacaaacaaa caaacaaaca aacaaacaaa aaccaataaa ccaaaaacat ttatctaaac    5460
aataaaataa aggacagata taatcaccga atatatgata gcattttaaa ttgaaaaagc    5520
actaatgact acaatggatt ataaaacatc aaatacataa aattcttaag ttcctcctaa    5580
taccaaatac aaagcacatt ggtctttggt ttttacttgg gcaccaatgc atgctgaaaa    5640
agagtcgttc atttttaga gtagttttag gttcacagca aaattgagca gaaggtagag    5700
ttctcatgtg tctctttgct cctcccctg cccccagcct ccccactatc aacaccccca    5760
cactacagtg gtagatttat tacaatccct gaacccacag tgacacatca ctatcaccca    5820
aagttcatag cgtacagcag ggttcactct tgggcagtac attccatggg tttgataaa    5880 tgtgtaatga tgtctccacc atcacagcat caggcagagt agtttcactg ctctaacaaa    5940
atcctctgcc tattcacccc tctcattaaa gccaaacact ctgtttcctt ttttcctttt    6000
agagacagtg tctcgctctg tcaaccaggc tgaagtgcaa tggcaatcac agcccattgc    6060
agcctccaac tcctgggctc aagtgatcct cctatctcag cctccagtgg ctacgactgc    6120
aggcatacgg caacggcacc caactaattt tttgtagaga tagggtcttg ctatgttgcc    6180
caggctggtc ttgaactctt ggtcctgcct tagcctccca gagctctggg attacaggcg    6240
tgaaccaccg tgcccgtccc aaacactctg tttcgacctg cttttaaaca actgacccct    6300
ggatgcatta aaaggatcag ggtgtctgaa actggcctct gcagcaggac cttccttcct    6360
acacatctcc cagtggccag tgtgaggatt ctccccacaa gaaaccactg gagggggcct    6420
cctcctgtcc gggtttgggg ctgtacaagg agcatcatgg acctggctca ggcctcagga    6480
ggggccctgg gctggggaaa atgtgggata gcatcgaggc agtcccactc ctacccaggg    6540
ccgggctaga cctggggaca gtctcagcca tctcctcgct gcgtccacac aattccaccc    6600 ccaccccac ccccaggctg gccctcacgg aagaacaaca gctgatgttt gagaaactga    6660
ctctgtattg cgacagctac atccagctca tccccatttc cttcgtgctg ggtgagttcc    6720
cccttctggc tgttccgggt ccctgtggcc gcccaggctc cagacaggcc aggggaggat    6780
cacgaggagc tgcggcaagg ggctggggag ggggcggggg aacgccagcg gcaggtcggc    6840
gcctctctgt agggaaaggt gcggactgca gccagagaaa ctgaagttag acgttaggta    6900
```

-continued

```
agacgtcctg ccgttagcaa tgaaaacccc attttctgag ggaagcgctg acatcatggt     6960
ccctggagcc cctgcgcggg aggggagggg gtctggcgga tttctgggac cagcaggggg     7020
accccggggt gacagaaccc ttggggctct cgcgcctcca tgcgaggctc tgcctgcctc     7080
tcgctcccga gcgccttcca ggagggctgg gggctaggcc cgctcgcagc agaaagctgg     7140
aggagccgag gcatcgccgg gcgctgggcc ctgggctctg gccgcagcct ggcccctcgc     7200
ccctcgcccc ccgcccctcc tgcccaggct tctacgtgac gctggtcgtg acccgctggt     7260
ggaaccagta cgagaacctg ccgtggcccg accgcctcat gagcctggtg tcgggcttcg     7320
tcgaaggcaa ggacgagcaa ggccggctgc tgcggcgcac gctcatccgc tacgccaacc     7380
tgggcaacgt gctcatcctg cgcagcgtca gcaccgcagt ctacaagcgc ttccccagcg     7440
cccagcacct ggtgcaagca ggtgggcgga ccggagcaa cggggaggca ccgggcagag     7500
ccagggccg agatgggcgc ggcaggaacg gaagatgggt ggagccaaag tcccccggac     7560
tcggggact gggtggagcc aggagtgggg tgtggtcaag atttgggggt ccaattgggc     7620
gggacagagt cgggtgtctg aaggtggggc gaggccagga gcccaccctc cgagagtagg     7680
agtctgaggc agggctaagg acccttgagg gataatggaa agaagggtga cggcttggga     7740
actggtgagg tactagggtc tacttccctc tgcccttgcc cctcttgatc tccggtttcc     7800
actctggagg tatgggacat tggtctctga caccccctca gcctggcctg acctggtcct     7860
ggttaataag acagacccag gctaggcgtg gtggctctcg cctgtaatcc cagtgcttta     7920
ggaggcaaag gtgggaagat cgcttgagcc cagctgtttg agacgcccct gagcaacata     7980
gcgagacccc catctctaca aaacattaa aaattagcag gcatggtggg cgtgtgcctg     8040
tagtctgagg ctgagtatcg ggaggctgag gcaggaggat cacttgagcc cagcagttcc     8100
aggctgcagt gcgctaagat cgcaccgctg cactccaacc tcggtgacag agccagaccc     8160
tttctctgga aataaataaa taccctgccc acatgtcag cccagaacag cacctagtag     8220
gtgctcagaa atttttttgt tgttgaaaga agaggatgg caaggagtg ctgaggttcc     8280
tataggtcag caggtgccgg ccatcccttc tgcaggttct cccacccacc gccttcttca     8340
ctccactctg caggctttat gactccggca gaacacaagc agttggagaa actgagccta     8400
ccacacaaca tgttctgggt gccctgggtg tggtttgcca acctgtcaat gaaggcgtgg     8460
cttggaggtc gaatccggga ccctatcctg ctccagagcc tgctgaacgt gagcccactg     8520
tacagacagg gctgccgcag agtgggaagg gttgtggtcc acaggaaaca aggtttccta     8580
caaagagaag ccttgggccc ctgagggtct tccgagagcc ggaggtgggg ttgcagaatc     8640
ttttccaaca gcaatccaca gcccgaggtg gtcccttatc agaggcccct ccctcttctc     8700
caagtctgtg aggtcctggt tccctttga tagatgagga agctgagaca caaagaggtt     8760
tagtgagctt cccatggcca cacagccagg aatggaccat aggtaccagg ccctggtacc     8820
tggagaaag gtgggggcga gcccaggtg ggggcaggt gtgttcagaa ccccatcccc     8880
ctcttctgcc ccccaggaga tgaacacctt gcgtactcag tgtggacacc tgtatgccta     8940
cgactggatt agtatcccac tggtgtatac acaggtgagg actaggctgg tgaggctgcc     9000
cttttgggaa actgaggcta gaaggaccaa ggaagcagct ggggtgggaa gggctcacct     9060
agaggctaag tggctcccct gggagttggg tccacacttt gaagttgggt ctggactttg     9120
aagtgccaag ttctaagagt ccaggctcct gcctggccca gtccagtaga ggcaatgtga     9180
ttatccccat attaaagaga ggttggccgg gcacagtggc tcatgcctgt aatcccagca     9240
cttttgggaag ctgaggcagg tggatcacct gaggtcagga gttcgagacc agcctggcca     9300
```

-continued

```
acatggtgaa acccccatctc tactgaaaat acagaattag ctgtgtggtg gtgcacgcct    9360
gtaatcccag ctacttggga ggctgaggca ggagaatcgc ttgaacccgg gaggtggagg    9420
ttgcagtgag ctgagatcat gccactgcac tccagcctgg gcgacacagc aagactctgt    9480
ctcaaacaaa caaacaaaca aacaaacaaa caaacaaaca aaggggttaa cagagcccct    9540
aagtcacata agtgtgcaag tcagaacaag gccttggtct cctgtctcag actcccagcc    9600
cctggagcat cctgatttca gggttcccac ctagcccttt gctaccacat cctcctcctc    9660
ctcctcctcc tcccaggtgg tgactgtggc ggtgtacagc ttcttcctga cttgtctagt    9720
tgggcggcag tttctgaacc cagccaaggc ctaccctggc catgagctgg acctcgttgt    9780
gcccgtcttc acgttcctgc agttcttctt ctatgttggc tggctgaagg tgggcctctc    9840
cagggccctg ctgggctgga ggcatggcca gagggtcat ggccagcagc tgcttgagac    9900
gaggatgcag tgtcaggaaa ggaaggtctc acgggtagaa agcagccagg cgtggtggcg    9960
cacacctgta atcccagcta ctcgggaggc tgaggcagga gaatcgcttg aacccgggag   10020
gcggaggttg tggtgagttg agatcgtgcc actgcactcc agcctgggca aaagaatgaa   10080
actctatctc aaaacaaca caacaacaa acaaagccc taaggttcag aagcccctgc   10140
cctttagaag cagagcgaac actctcctat taagatgctg ttgggtgtct ttttcactca   10200
gtagctgtcc agtattctcc acacagcata atcgacagat tctaatacaa atttcttcaa   10260
ctcttaattc ctcctttgtg ccaccatttt ttcttctacc tcctaattta tgaatgggtt   10320
agtatgctct gcttctgcat tgagacaaaa tacagagaga gagaaagatc tatcttaatc   10380
ccgcccatt ttagttggaa aaaaacttta ttaaatcagg caagtaaaat ccgccaagga   10440
ttgnnnnnnn nnnagatgtt ctgaatcaga gagttttctc tcgagctctt tatctttcct   10500
tccttctgtt gcccacccac tctctctccc ttcctacctt cctttatttt ttggtaatgg   10560
gggtgtaagt ctctgtctct gcccttcctg tcactgtgac acacacacac acacacacac   10620
acacacacac acacacacac attcctattc ctctaaattc ccctgcacc ccagttatc    10680
tttggtttct gcagatcaaa acaaatcaca ctttatgct tgaaattctc cagggtgccc    10740
cagtggcctg caagatgtcc cctggacccc taaggcagac gcgtgtcacc tcttcgggc    10800
tttgttaggg cattttagag gttgctatcc aggaatctgc ccacctagac tgcccttag   10860
ttcagcccag cttcagtata tatctctgtt gcatgaatga ataaaattat gcaactccag   10920
gtaagataca tgaggtgaga taaaggcagt gactcagccg agtgatacac tcagggacag   10980
ctgtgggtgt tcagggaagg actggctcag aagagttaga ggggctgtgt ccagaagtgt   11040
gtgggtgcct acaagtgtgg ggggctggag ccctaaactc tgcctttgaa gacagtggtc   11100
aggcaggaag ggcttcatgg ggtgtggaaa tagcagcagc tgaggtttaa agggggaagc   11160
tggcttttgag gagttctgcc tgagggttta cagagcctca cctgtcccca aggtggcaga   11220
gcagctcatc aaccccttg gagaggatga tgatgatttt gagaccaact ggattgtcga   11280
caggaattg caggtatggg gagagggaga gaaaccatac catggaccttt ccccaaagtg   11340
gacccaaaga gagctcctcc ctcctgcagc cagtcattca ctcacaggat tctcacctca   11400
atctttgagg ctgcaggcag gcacccatct ccccatttca caggcaggga aactgaggtc   11460
cagagagagg gagagattcc tccaagtcat caggcacata caaggtcctg cctgggatga   11520
tctttctgtg ggacttcttc tgtccctggt gaccaggtgt cctgttggc tgtggatgag   11580
atgcaccagg acctgcctcg gatggagccg gacatgtact ggaataagcc cgagccacag   11640
```

```
cccccctaca cagctgcttc cgcccagttc cgtcgagcct cctttatggg ctccaccttc   11700
aacatcaggt gtggccagag ccagggggct gggtgggaag cccctcctag tgcagggtc    11760 tgcctaggaa cttagaatag cactagttaa tgcatacagg ttgcttcagt aagtgtcagg   11820
cactgtacta tgctctttat aaacattaac tattttttc ctcccaataa ttctggtttg    11880
ttatcccaag ttttcagata attaaagtac aggttcagag agagtaagtt gtccaaggcc   11940
acatagctac caaatggtgc atttgctact cgaaggacag cctatgatca gtgatgcagt   12000
ggaacgttag gacctggctc ttgtcatcca gaactatgtt ttcttttctt tttgagacag   12060
tatctcgctc tgtcgcccag gttggagcgc agtggcgtga tcttggctca ctgcaacctc   12120
cgcctcctgg gttcaagtga ttctcctgct tcagcctccc cagtagctgg gattacaggt   12180
gcccacaacc acaactggct aattttgta cttttagtag agatgaggtt tcaccatgtt    12240
ggccaggctg gtctccaact cctgaccagt aatctgcccg ctttggcctc ccaaaatgct   12300
ggaattatag tgtgtcaaaac tatgttttct gataagctac gatgcttgga tgggaagtgg  12360
aagtggggtt ccctgggatg ggggaggggc agcaaagtcc cagcaggcag ccaggccatc   12420
acaggtacct cctgaattga ctttgtccta ccgagtaaag ggctcaggcc acccacagca   12480
gccagactta tccccacatg gtcccacttc cctgattcca tctgaatccc tcttgagctg   12540
cagtgggctg aagggctatc ccagctggtc ctttctcccc aggacaacag agttgaaagt   12600
gccttggaga gtgttgggca catgtcaggg ttcatactca agggtttctt ccacggtatc   12660
cagtgctgtt ctcgcttgtt ctttctttt ttttttta acggagttt cactcttgtt       12720 gcccagagct ggagtgcagt ggcataatct cggctcactg caacctccgc ctcccagatt   12780
caagcaattc tcctgcctca gcctcctgag tagctgggat tataggtgcc agccaccaag   12840
cccggctaat ttttgtattt ttagtagaga cagttttcacc atgttggcca ggctggtctc  12900
gaactcctga cctcaggtga tccaccctcc tcagcctccc aaagtgctgg gattacatgt   12960
gtgagccact gtgcctggct gcttgttctt ttaagaacca aatatcctac tagactgcaa   13020
tcgagtttaa ctacagtcta tagatactgt gaggaatggt tgggaaggtc atcaaatgaa   13080
ggctggaggc ttgcttaggt cagaaacatt tctggaggat gactttgagc cctacatggt   13140
ctgtacccca gcagctgaag gttgttgagg gatggggagg gctgaaaaca gaacgataaa   13200
gcatagacct tgtctccaag gaatgcacaa tttatggagg gagctcaaac ccaagtctca   13260
aactctggat acaaggtaca aagtactgga tgtccagaaa agggacagaa catggaacac   13320
agtcatcttt gtctgcctgg gaggcggctt ccagctgggc ctggagctga gccatggaac   13380 atggaagaa tctgaacttg ggcaagggca ggccatactc tctggtagat aagctttcct    13440
tgcagggtaa aggtctgggg ctcccgggat gcctgttgct aggaagtcaa atttctcttt   13500
gtggatgtca ctcccagttg gaaccacaaa ttcctggcat tgcccagagt cactcatggg   13560
cctcatctga accactcatg ccagggcacc agtgtttctg actgcctgga gtgaggggtt   13620
ttacagggga agtgaatgat gaggaggcct ttacacgcca ggcggggtgg ttgcggggt    13680 tggatgttaa ctctggtcaa gagggaatca acaaacagtg aggtgagctg ggcctggagg   13740
gatcaccggg aggtacagta cagatcagga gagaggtgag agctggggca tggtgaggaa   13800
gacggtgtgg ccttggcttg ggccaactga gagagaggg cggggtaag ggagaagtaa     13860 ggccaggtgt tggtcctttg tccactggct cagccctgca tctcctgttt ctttccagcc   13920
tgaacaaaga gggagatggag ttccagccca atcaggagga cgaggaggat gctcacgctg  13980
gcatcattgg ccgcttccta ggcctgcagt cccatgatca ccatcctccc agggcaaact   14040
```

-continued

```
caaggaccaa actactgtgg cccaagaggg aatcccttct ccacgagggc ctgcccaaaa      14100
accacaaggc agccaaacag aacgttaggg gccaggaaga caacaaggcc tggaagctta      14160
aggctgtgga cgccttcaag tctgccccac tgtatcagag gccaggctac tacagtgccc      14220
cacagacgcc cctcagcccc actcccatgt tcttcccct agaaccatca gcgccgtcaa       14280
agcttcacag tgtcacaggc atagacacca aagacaaaag cttaaagact gtgagttctg      14340
gggccaagaa aagttttgaa ttgctctcag agagcgatgg ggccttgatg gagcacccag      14400
aagtatctca agtgaggagg aaaactgtgg agtttaacct gacggatatg ccagagatcc      14460
ccgaaaatca cctcaaagaa cctttggaac aatcaccaac caacatacac actacactca      14520
aagatcacat ggatccttat tgggccttgg aaaacaggtc tgtcctccac ctgaaccagg      14580
ggcactgcat tgccctgtgc cccaccccag cttcccttgc tctgagccta cccttcctcc      14640
acaatttcct agggttccat cactgccaga gcacactgga cctacgccca gcactggctt      14700
ggggtatata cttggccacc ttcacaggga tcctagggaa gtgttcggga ccttttctca      14760
cttcaccctg gtatcacccg gaagacttct tgggaccagg tgaaggaaga tgaggttgtg      14820
ctgaccagaa tgctgctgga gaactgcccc agggctgaca ggccaggctt agctgagcag      14880
atgttatcac tggccccaac ttactttgag caagggtggc tgacccaaaa ccatgaggtg      14940
gcagtcagct ggatgacaga tgaacacttc ccccataact atttagggta gtacccaagc      15000
actacaggaa agggtggcag gaactgcctc actcctagga actggtagat ggtgaggttg      15060
agggtgtcca gcgcccttag gtcatttct cactgcctgg gaacctcacc aaaatacttc       15120
ttgcttcctt ggggtcagcc caaagctgtc acaaaatcag atatttccct ttattccaga      15180
tttcctggac actgtcaccc aattataaac accccacttc agccccaatc acgtgggagg      15240
aagtgtaact tcccttttct ggattctcaa gcagttactt tcacgggtca gaacacgcag      15300
ctattatgat tgaaaccta aaagggcaac aatttcantc ttgcttctag gctaagacag       15360
gaacttggca aacatctgtg gcctgttcag caaaggatgt tcatatttaa gaatcttgtc      15420
ttgggctggg tgtggaggca agtgaatcac aggaggtcag gagtttgaga ccaacctggc      15480
caacatgatg aaaccccatc tctaccaaaa aaaatacaaa tcagctggcc gtcgtggtgt      15540
gcctgtagtc ccaacgcagg aggttgaggg gagaattgct tgaacccagg aggtggtggt      15600
tgcagtgaga ttgagcaact gcaatccagc ctgggcgacg gagtgagact gtctcaaaaa      15660
aaaaaaaaaa aggatcgtct caacctttgc cctcctactg caacattttg gtatttgaaa      15720
tgaaggtacc ttccatactt atgctgttaa tactttcatt ctcactaggg atgaagcaca      15780
ttcctaacct gcttcctaat ggggatgctt cgccagccag gtcctcacct gtgtgtacac      15840
cagcaggaca ctgatccagt cacagccata cagctgtcca cactgaagaa cgtgtcctac      15900
aacagcctga atcaaatggt tagcttaata gataaaaatc ccagactact tcagccttta      15960 atgccttta ttcataaaaa ctgtgaaagc tagactgaac cattggaaac atttaactca       16020
gactctggat tcagagtcgg gaaccctag ttctatctga atccaagaca gccacacctt       16080
agtatactgc ccaaactaat gagtttaata aatacaaata ctcgt                     16125
```

<210> SEQ ID NO 2
<211> LENGTH: 2229
<212> TYPE: DNA
<213> ORGANISM: Homo Sapiens

<400> SEQUENCE: 2

```
cagggagtcc caccagccta gtcgccagac cttctgtggg atcatcggac ccacctggaa     60
ccccacctga cccaagccca cctgctgcag cccactgcct ggccatgacc atcacttaca    120
caagccaagt ggctaatgcc cgcttaggct ccttctcccg cctgctgctg tgctggcggg    180
gcagcatcta caagctgcta tatggcgagt tcttaatctt cctgctctgc tactacatca    240
tccgctttat ttataggctg cccctcacgg aagaacaaca gctgatgttt gagaaactga    300
ctctgtattg cgacagctac atccagctca tccccatttc cttcgtgctg ggcttctacg    360
tgacgctggt cgtgacccgc tggtggaacc agtacgagaa cctgccgtgg cccgaccgcc    420
tcatgagcct ggtgtcgggc ttcgtcgaag gcaaggacga gcaaggccgg ctgctgcggc    480
gcacgctcat ccgctacgcc aacctgggca cgtgctcat cctgcgcagc gtcagcaccg    540
cagtctacaa gcgcttcccc agcgcccagc acctggtgca agcaggcttt atgactccgg    600
cagaacacaa gcagttggag aaactgagcc taccacacaa catgttctgg gtgccctggg    660
tgtggtttgc caacctgtca atgaaggcgt ggcttggagg tcgaatccgg gaccctatcc    720
tgctccagag cctgctgaac gagatgaaca ccttgcgtac tcagtgtgga cacctgtatg    780
cctacgactg gattagtatc ccactggtgt atacacaggt ggtgactgtg gcggtgtaca    840
gcttcttcct gacttgtcta gttgggcggc agtttctgaa cccagccaag gcctaccctg    900
gccatgagct ggaccctcgtt gtgcccgtct tcacgttcct gcagttcttc ttctatgttg    960
gctggctgaa ggtggcagag cagctcatca ccccctttgg agaggatgat gatgattttg   1020
agaccaactg gattgtcgac aggaaatttgc aggtgtccct gttggctgtg gatgagatgc   1080
accaggacct gcctcggatg gagccggaca tgtactggaa taagcccgag ccacagcccc   1140
cctacacagc tgcttccgcc cagttccgtc gagcctcctt tatgggctcc accttcaaca   1200
tcagcctgaa caaagaggag atggagttcc agcccaatca ggaggacgag gaggatgctc   1260
acgctggcat cattggccgc ttcctaggcc tgcagtccca tgatcaccat cctcccaggg   1320
caaactcaag gaccaaacta ctgtggccca agagggaatc ccttctccac gagggcctgc   1380
ccaaaaacca caaggcagcc aaacagaacg ttagggggcca ggaagacaac aaggcctgga   1440
agcttaaggc tgtggacgcc ttcaagtctg gcccactgta tcagaggcca ggctactaca   1500
gtgccccaca gacgccctc agccccactc ccatgttctt ccccctagaa ccatcagcgc   1560
cgtcaaagct tcacagtgtc acaggcatag acaccaaaga caaaagctta aagactgtga   1620
gttctgggc caagaaaagt tttgaattgc tctcagagag cgatgggcc ttgatggagc   1680
acccagaagt atctcaagtg aggaggaaaa ctgtggagtt taacctgacg gatatgccag   1740
agatccccga aaatcacctc aaagaacctt tggaacaatc accaaccaac atacacacta   1800
cactcaaaga tcacatggat ccttattggg ccttggaaaa cagggatgaa gcacattcct   1860
aacctgcttc ctaatgggga tgcttcgcca gccaggtcct cacctgtgtg tacaccagca   1920
ggacactgat ccagtcacag ccatacagct gtccacactg aagaacgtgt cctacaacag   1980
cctgaatcaa atggttagct taatagataa aaatcccaga ctacttcagc ctttaatgcc   2040
ttttattcat aaaaactgtg aaagctagac tgaaccattg gaaacattta actcagactc   2100
tggattcaga gtcgggaacc cttagttcta tctgaatcca agacagccac accttagtat   2160
actgccccaaa ctaatgagtt taataaatac aaatactcgt taaaaaaaaa aaaaaaaaaa   2220
aaaaaaaaa                                                           2229
```

<210> SEQ ID NO 3
<211> LENGTH: 585

```
<212> TYPE: PRT
<213> ORGANISM: Homo Sapiens

<400> SEQUENCE: 3

Met Thr Ile Thr Tyr Thr Ser Gln Val Ala Asn Ala Arg Leu Gly Ser
 1               5                  10                  15

Phe Ser Arg Leu Leu Cys Trp Arg Gly Ser Ile Tyr Lys Leu Leu
            20                  25                  30

Tyr Gly Glu Phe Leu Ile Phe Leu Cys Tyr Tyr Ile Ile Arg Phe
            35                  40                  45

Ile Tyr Arg Leu Ala Leu Thr Glu Gln Gln Leu Met Phe Glu Lys
 50                  55                  60

Leu Thr Leu Tyr Cys Asp Ser Tyr Ile Gln Leu Ile Pro Ile Ser Phe
 65                  70                  75                  80

Val Leu Gly Phe Tyr Val Thr Leu Val Val Thr Arg Trp Trp Asn Gln
                85                  90                  95

Tyr Glu Asn Leu Pro Trp Pro Asp Arg Leu Met Ser Leu Val Ser Gly
            100                 105                 110

Phe Val Glu Gly Lys Asp Glu Gln Ser Arg Leu Leu Arg Arg Thr Leu
            115                 120                 125

Ile Arg Tyr Ala Asn Leu Gly Asn Val Leu Ile Leu Arg Ser Val Ser
            130                 135                 140

Thr Ala Val Tyr Lys Arg Phe Pro Ser Ala Gln His Leu Val Gln Ala
145                 150                 155                 160

Gly Phe Met Thr Pro Ala Glu His Lys Gln Leu Glu Lys Leu Ser Leu
                165                 170                 175

Pro His Asn Met Phe Trp Val Pro Trp Val Trp Phe Ala Asn Leu Ser
                180                 185                 190

Met Lys Ala Trp Leu Gly Gly Arg Ile Arg Asp Pro Ile Leu Leu Gln
                195                 200                 205

Ser Leu Leu Asn Glu Met Asn Thr Leu Arg Thr Gln Cys Gly His Leu
            210                 215                 220

Tyr Ala Tyr Asp Trp Ile Ser Ile Pro Leu Val Tyr Thr Gln Val Val
225                 230                 235                 240

Thr Val Ala Val Tyr Ser Phe Phe Leu Thr Cys Leu Val Gly Arg Gln
                245                 250                 255

Phe Leu Asn Pro Ala Lys Ala Tyr Pro Gly His Glu Leu Asp Leu Val
            260                 265                 270

Val Pro Val Phe Thr Phe Leu Gln Phe Phe Tyr Val Gly Trp Leu
            275                 280                 285

Lys Val Ala Glu Gln Leu Ile Asn Pro Phe Gly Glu Asp Asp Asp
290                 295                 300

Phe Glu Thr Asn Trp Ile Val Asp Arg Asn Leu Gln Val Ser Leu Leu
305                 310                 315                 320

Ala Val Asp Glu Met His Gln Asp Leu Pro Arg Met Glu Pro Asp Met
                325                 330                 335

Tyr Trp Asn Lys Pro Glu Pro Gln Pro Pro Tyr Thr Ala Ala Ser Ala
                340                 345                 350

Gln Phe Arg Arg Ala Ser Phe Met Gly Ser Thr Phe Asn Ile Ser Leu
                355                 360                 365

Asn Lys Glu Glu Met Glu Phe Gln Pro Asn Gln Glu Asp Glu Glu Asp
            370                 375                 380

Ala His Ala Gly Ile Ile Gly Arg Phe Leu Gly Leu Gln Ser His Asp
385                 390                 395                 400
```

```
His His Pro Pro Arg Ala Asn Ser Arg Thr Lys Leu Leu Trp Pro Lys
            405                 410                 415
Arg Glu Ser Leu Leu His Glu Gly Leu Pro Lys Asn His Lys Ala Ala
        420                 425                 430
Lys Gln Asn Val Arg Gly Gln Glu Asp Asn Lys Ala Trp Lys Leu Lys
    435                 440                 445
Ala Val Asp Ala Phe Lys Ser Gly Pro Leu Tyr Gln Arg Pro Gly Tyr
450                 455                 460
Tyr Ser Ala Pro Gln Thr Pro Leu Ser Pro Thr Pro Met Phe Phe Pro
465                 470                 475                 480
Leu Glu Pro Ser Ala Pro Ser Lys Leu His Ser Val Thr Gly Ile Asp
            485                 490                 495
Thr Lys Asp Lys Ser Leu Lys Thr Val Ser Ser Gly Ala Lys Lys Ser
            500                 505                 510
Phe Glu Leu Leu Ser Glu Ser Asp Gly Ala Leu Met Glu His Pro Glu
    515                 520                 525
Val Ser Gln Val Arg Arg Lys Thr Val Glu Phe Asn Leu Thr Asp Met
530                 535                 540
Pro Glu Ile Pro Glu Asn His Leu Lys Glu Pro Leu Glu Gln Ser Pro
545                 550                 555                 560
Thr Asn Ile His Thr Thr Leu Lys Asp His Met Asp Pro Tyr Trp Ala
            565                 570                 575
Leu Glu Asn Arg Asp Glu Ala His Ser
            580                 585

<210> SEQ ID NO 4
<211> LENGTH: 2429
<212> TYPE: DNA
<213> ORGANISM: Homo Sapiens

<400> SEQUENCE: 4
cagggagtcc caccagccta gtcgccagac cttctgtggg atcatcggac ccacctggaa      60
cccccacctga cccaagccca cctgctgcag cccactgcct ggccatgacc atcacttaca     120
caagccaagt ggctaatgcc cgcttaggct ccttctcccg cctgctgctg tgctggcggg     180
gcagcatcta caagctgcta tatggcgagt tcttaatctt cctgctctgc tactacatca     240
tccgctttat ttataggctg gccctcacgg aagaacaaca gctgatgttt gagaaactga     300
ctctgtattg cgacagctac atccagctca tccccatttc cttcgtgctg ggcttctacg     360
tgacgctggt cgtgacccgc tggtggaacc agtacgagaa cctgccgtgg cccgaccgcc     420
tcatgagcct ggtgtcgggc ttcgtcgaag gcaaggacga gcaaggccgg ctgctgcggg     480
gcacgctcat ccgctacgcc aacctgggca cgtgctcat cctgcgcagc gtcagcaccg      540
cagtctacaa gcgcttcccc agcgcccagc acctggtgca agcaggcttt atgactccgg     600
cagaacacaa gcagttggag aaactgagcc taccacacaa catgttctgg gtgccctggg     660
tgtggtttgc caacctgtca atgaaggcgt ggcttggagg tcgaatccgg acccctatcc     720
tgctccagag cctgctgaac gagatgaaca ccttgcgtac tcagtgtgga cacctgtatg     780
cctacgactg gattagtatc ccactggtgt atacacaggt ggtgactgtg gcggtgtaca     840
gcttcttcct gacttgtcta gttgggcggc agtttctgaa cccagccaag gcctaccctg     900
gccatgagct ggaccttgtt gtgcccgtct tcacgttcct gcagttcttc ttctatgttg     960
gctggctgaa ggtgggcctc tccagggccc tgctgggctg gaggcatggc cagagggggtc    1020
```

-continued

```
atggccagca gctgcttgag acgaggatgc agtgtcagga aaggaaggtc tcacgggtag      1080
aaagcagcca ggcgtggtgg cgcacacctg taatcccagc tactcgggag gctgaggcag      1140
gagaatcgct tgaacccggg aggcggaggt tgtggtggca gagcagctca tcaaccccct      1200
tggagaggat gatgatgatt ttgagaccaa ctggattgtc gacaggaatt tgcaggtgtc      1260
cctgttggct gtggatgaga tgcaccagga cctgcctcgg atggagccgg acatgtactg      1320
gaataagccc gagccacagc cccctacac agctgcttcc gcccagttcc gtcgagcctc       1380
ctttatgggc tccaccttca acatcagcct gaacaaagag gagatggagt tccagcccaa      1440
tcaggaggac gaggaggatg ctcacgctgg catcattggc cgcttcctag gcctgcagtc      1500
ccatgatcac catcctccca gggcaaactc aaggaccaaa ctactgtggc caagaggga       1560 atcccttctc cacgagggcc tgcccaaaaa ccacaaggca gccaaacaga acgttagggg      1620
ccaggaagac aacaaggcct ggaagcttaa ggctgtggac gccttcaagt ctggcccact      1680
gtatcagagg ccaggctact acagtgcccc acagacgccc ctcagcccca ctcccatgtt      1740
cttcccccta gaaccatcag cgccgtcaaa gcttcacagt gtcacaggca tagacaccaa      1800
agacaaaagc ttaaagactg tgagttctgg ggccaagaaa agttttgaat tgctctcaga      1860
gagcgatggg gccttgatgg agcacccaga agtatctcaa gtgaggagga aaactgtgga      1920
gtttaacctg acggatatgc cagagatccc cgaaaatcac ctcaaagaac ctttggaaca      1980
atcaccaacc aacatacaca ctacactcaa agatcacatg gatccttatt gggccttgga      2040
aaacagggat gaagcacatt cctaacctgc ttcctaatgg ggatgcttcg ccagccaggt      2100
cctcacctgt gtgtacacca gcaggacact gatccagtca cagccataca gctgtccaca      2160
ctgaagaacg tgtcctacaa cagcctgaat caaatggtta gcttaataga taaaaatccc      2220
agactacttc agcctttaat gccttttatt cataaaaact gtgaaagcta gactgaacca      2280
ttggaaacat ttaactcaga ctctggattc agagtcggga acccttagtt ctatctgaat      2340
ccaagacagc cacaccttag tatactgccc aaactaatga gtttaataaa tacaaatact      2400
cgttaaaaaa aaaaaaaaa aaaaaaaaa                                        2429
```

<210> SEQ ID NO 5
<211> LENGTH: 435
<212> TYPE: PRT
<213> ORGANISM: Homo Sapiens

<400> SEQUENCE: 5

```
Met Thr Ile Thr Tyr Thr Ser Gln Val Ala Asn Ala Arg Leu Gly Ser
 1               5                   10                  15

Phe Ser Arg Leu Leu Leu Cys Trp Arg Gly Ser Ile Tyr Lys Leu Leu
            20                  25                  30

Tyr Gly Glu Phe Leu Ile Phe Leu Leu Cys Tyr Tyr Ile Ile Arg Phe
        35                  40                  45

Ile Tyr Arg Leu Ala Leu Thr Glu Glu Gln Leu Met Phe Glu Lys
    50                  55                  60

Leu Thr Leu Tyr Cys Asp Ser Tyr Ile Gln Leu Ile Pro Ile Ser Phe
65                  70                  75                  80

Val Leu Gly Phe Tyr Val Thr Leu Val Val Thr Arg Trp Trp Asn Gln
                85                  90                  95

Tyr Glu Asn Leu Pro Trp Pro Asp Arg Leu Met Ser Leu Val Ser Gly
            100                 105                 110

Phe Val Glu Gly Lys Asp Glu Gln Gly Arg Leu Leu Arg Arg Thr Leu
        115                 120                 125
```

```
Ile Arg Tyr Ala Asn Leu Gly Asn Val Leu Ile Leu Arg Ser Val Ser
    130                 135                 140

Thr Ala Val Tyr Lys Arg Phe Pro Ser Ala Gln His Leu Val Gln Ala
145                 150                 155                 160

Gly Phe Met Thr Pro Ala Glu His Lys Gln Leu Glu Lys Leu Ser Leu
                165                 170                 175

Pro His Asn Met Phe Trp Val Pro Trp Val Trp Phe Ala Asn Leu Ser
            180                 185                 190

Met Lys Ala Trp Leu Gly Gly Arg Ile Arg Asp Pro Ile Leu Leu Gln
        195                 200                 205

Ser Leu Leu Asn Glu Met Asn Thr Leu Arg Thr Gln Cys Gly His Leu
    210                 215                 220

Tyr Ala Tyr Asp Trp Ile Ser Ile Pro Leu Val Tyr Thr Gln Val Val
225                 230                 235                 240

Thr Val Ala Val Tyr Ser Phe Phe Leu Thr Cys Leu Val Gly Arg Gln
                245                 250                 255

Phe Leu Asn Pro Ala Lys Ala Tyr Pro Gly His Glu Leu Asp Leu Val
            260                 265                 270

Val Pro Val Phe Thr Phe Leu Gln Phe Phe Phe Tyr Val Gly Trp Leu
        275                 280                 285

Lys Val Gly Leu Ser Arg Ala Leu Leu Gly Trp Arg His Gly Gln Arg
    290                 295                 300

Gly His Gly Gln Gln Leu Leu Glu Thr Arg Met Gln Cys Gln Glu Arg
305                 310                 315                 320

Lys Val Ser Arg Val Glu Ser Ser Gln Ala Trp Trp Arg Thr Pro Val
                325                 330                 335

Ile Pro Ala Thr Arg Glu Ala Glu Ala Gly Glu Ser Leu Glu Pro Gly
            340                 345                 350

Arg Arg Arg Leu Trp Trp Gln Ser Ser Ser Thr Pro Leu Glu Arg
        355                 360                 365

Met Met Met Ile Leu Arg Pro Thr Gly Leu Ser Thr Gly Ile Cys Arg
370                 375                 380

Cys Pro Cys Trp Leu Trp Met Arg Cys Thr Arg Thr Cys Leu Gly Trp
385                 390                 395                 400

Ser Arg Thr Cys Thr Gly Ile Ser Pro Ser His Ser Pro Pro Thr Gln
                405                 410                 415

Leu Leu Pro Pro Ser Ser Val Glu Pro Pro Leu Trp Ala Pro Pro Ser
            420                 425                 430

Thr Ser Ala
        435

<210> SEQ ID NO 6
<211> LENGTH: 18
<212> TYPE: DNA
<213> ORGANISM: Homo Sapiens

<400> SEQUENCE: 6
cagggagtcc caccagcc                                                      18

<210> SEQ ID NO 7
<211> LENGTH: 18
<212> TYPE: DNA
<213> ORGANISM: Homo Sapiens

<400> SEQUENCE: 7
```

-continued tccccattag gaagcagg     18

<210> SEQ ID NO 8
<211> LENGTH: 18
<212> TYPE: DNA
<213> ORGANISM: Homo Sapiens

<400> SEQUENCE: 8
tctcctcttt gttcaggc     18

<210> SEQ ID NO 9
<211> LENGTH: 21
<212> TYPE: DNA
<213> ORGANISM: Homo Sapiens

<400> SEQUENCE: 9
ctagtcgcca gaccttctgt g     21

<210> SEQ ID NO 10
<211> LENGTH: 20
<212> TYPE: DNA
<213> ORGANISM: Homo Sapiens

<400> SEQUENCE: 10
cttgtagact gcggtgctga     20

<210> SEQ ID NO 11
<211> LENGTH: 20
<212> TYPE: DNA
<213> ORGANISM: Homo Sapiens

<400> SEQUENCE: 11
gaaagcaagg acgagcaaag     20

<210> SEQ ID NO 12
<211> LENGTH: 22
<212> TYPE: DNA
<213> ORGANISM: Homo Sapiens

<400> SEQUENCE: 12
aatccagtcg taggcataca gg     22

<210> SEQ ID NO 13
<211> LENGTH: 21
<212> TYPE: DNA
<213> ORGANISM: Homo Sapiens

<400> SEQUENCE: 13
accttgcgta ctcagtgtgg a     21

<210> SEQ ID NO 14
<211> LENGTH: 21
<212> TYPE: DNA
<213> ORGANISM: Homo Sapiens

<400> SEQUENCE: 14
tgtcgacaat ccagttggtc t     21

<210> SEQ ID NO 15
<211> LENGTH: 20
<212> TYPE: DNA
<213> ORGANISM: Homo Sapiens

<400> SEQUENCE: 15 cccctttggag aggatgatga                                              20

<210> SEQ ID NO 16
<211> LENGTH: 20
<212> TYPE: DNA
<213> ORGANISM: Homo Sapiens

<400> SEQUENCE: 16
ctctggcata tccgtcaggt                                               20

<210> SEQ ID NO 17
<211> LENGTH: 20
<212> TYPE: DNA
<213> ORGANISM: Homo Sapiens

<400> SEQUENCE: 17
cttcaagtct gccccactgt                                               20

<210> SEQ ID NO 18
<211> LENGTH: 20
<212> TYPE: DNA
<213> ORGANISM: Homo Sapiens

<400> SEQUENCE: 18
gcatccccat taggaagcag                                               20

<210> SEQ ID NO 19
<211> LENGTH: 20
<212> TYPE: DNA
<213> ORGANISM: Homo Sapiens

<400> SEQUENCE: 19
ctaagcgggc attagccact                                               20

<210> SEQ ID NO 20
<211> LENGTH: 22
<212> TYPE: DNA
<213> ORGANISM: Homo Sapiens

<400> SEQUENCE: 20
tggggttcca ggtgggtccg at                                            22

<210> SEQ ID NO 21
<211> LENGTH: 27
<212> TYPE: DNA
<213> ORGANISM: Homo Sapiens

<400> SEQUENCE: 21
ccatcctaat acgactcact atagggc                                       27

<210> SEQ ID NO 22
<211> LENGTH: 27
<212> TYPE: DNA
<213> ORGANISM: Homo Sapiens

<400> SEQUENCE: 22
ggatgaagca cattcctaac ctgcttc                                       27

<210> SEQ ID NO 23
<211> LENGTH: 18
<212> TYPE: DNA
<213> ORGANISM: Homo Sapiens

```
<400> SEQUENCE: 23
aaagctggag gagccgag                                                      18

<210> SEQ ID NO 24
<211> LENGTH: 19
<212> TYPE: DNA
<213> ORGANISM: Homo Sapiens

<400> SEQUENCE: 24
ctccacccat cttccgttc                                                     19

<210> SEQ ID NO 25
<211> LENGTH: 20
<212> TYPE: DNA
<213> ORGANISM: Homo Sapiens

<400> SEQUENCE: 25
taggctcaga gcaagggaag                                                    20

<210> SEQ ID NO 26
<211> LENGTH: 20
<212> TYPE: DNA
<213> ORGANISM: Mus Musculus

<400> SEQUENCE: 26
acacaacaca ttctgggtgc                                                    20

<210> SEQ ID NO 27
<211> LENGTH: 20
<212> TYPE: DNA
<213> ORGANISM: Mus Musculus

<400> SEQUENCE: 27
ttcagaaact gcttcccgat                                                    20

<210> SEQ ID NO 28
<211> LENGTH: 1916
<212> TYPE: DNA
<213> ORGANISM: Mus Musculus

<400> SEQUENCE: 28
gtgccaagcc atgactatca cctacacaaa caaagtagcc aatgcccgcc tcggttcgtt        60
ctcgtccctc ctcctgtgct ggcgaggcag catctacaag ctgctgtatg gagaattcct       120
tgtcttcata ttcctctact attccatccg tggactctac agaatggttc tctcgagtga       180
tcagcagctg ttgtttgaga agctggctct gtactgcgac agctacattc agctcatccc       240
tatatccttc gttctgggtt tctatgttac attggtggtg agccgctggt ggagccagta       300
cgagaacttg ccgtggcccg accgcctcat gatccaggtg tctagcttcg tggagggcaa       360
ggatgaggaa ggccgtttgc tgcggcgcac gctcatccgc tacgccatcc tgggccaagt       420
gctcatcctg cgcagcatca gcacctcggt ctacaagcgc tttcccactc ttcaccacct       480
ggtgctagca ggttttatga cccatgggga acataagcag ttgcagaagt tgggcctacc       540
acacaacaca ttctgggtgc cctggtgtg gtttgccaac ttgtcaatga aggcctatct       600
tggaggtcga atccgggaca ccgtcctgct ccagagcctg atgaatgagg tgtgtacttt       660
gcgtactcag tgtggacagc tgtatgccta cgactggata agtatcccat ggtgtacac       720 acaggtggtg acagtggcag tatacagctt tttccttgca tgcttgatcg ggaggcagtt       780
tctgaaccca aacaaggact acccaggcca tgagatggat ctggttgtgc ctgtcttcac       840
```

-continued

```
aatcctgcaa ttcttattct acatgggctg gctgaaggtg gcagaacagc tcatcaaccc      900
cttcggggag gacgatgatg attttgagac taactggatc attgacagaa acctgcaggt      960
gtccctgttg tccgtggatg ggatgcacca gaacttgcct cccatggaac gtgacatgta     1020
ctggaacgag gcagcgcctc agccgcccta cacagctgct tctgccaggt ctcgccggca     1080
ttccttcatg ggctccacct tcaacatcag cctaaagaaa gaagactag agctttggtc      1140 aaaagaggag gctgacacgg ataagaaaga gagtggctat agcagcacca taggctgctt     1200
cttaggactg caacccaaaa actaccatct tcccttgaaa gacttaaaga ccaaactatt     1260
gtgttctaag aaccccctcc tcgaaggcca gtgtaaggat gccaaccaga aaaccagaa      1320 agatgtctgg aaatttaagg gtctggactt cttgaaatgt gttccaaggt ttaagaggag     1380
aggctcccat tgtggcccac aggcacccag cagccaccct actgagcagt cagcaccctc     1440
cagttcagac acaggtgatg ggccttccac agattaccaa gaaatctgtc acatgaaaaa     1500
gaaaactgtg gagtttaact tgaacattcc agagagcccc acagaacatc ttcaacagcg     1560
ccgtttggac cagatgtcaa ccaatataca ggctctaatg aaggagcatg cagagtccta     1620
tccctacagg gatgaagctg gcaccaaacc tgttctctat gagtgatgcc tcacagcctg     1680
gccctgactt gcaaggatgc ccagcagggc actgacccag tcaaaggcac acaagcagcg     1740
acacccagga gtgtgttccc acgacagtct agcatgtaac tcagaaccaa gagtacttaa     1800
tagtcctgcc tgaaaacacc tgtatttac gatctttccc aaactaagga gtttaataaa      1860
cgtgaatatt cttttaggtg aaaaaaaaaa aaaaaaaaaa aaaaaaaaaa aaaaaa          1916
```

<210> SEQ ID NO 29
<211> LENGTH: 551
<212> TYPE: PRT
<213> ORGANISM: Mus Musculus

<400> SEQUENCE: 29

```
Met Thr Ile Thr Tyr Thr Asn Lys Val Ala Asn Ala Arg Leu Gly Ser
  1               5                  10                  15

Phe Ser Ser Leu Leu Cys Trp Arg Gly Ser Ile Tyr Lys Leu Leu
             20                  25                  30

Tyr Gly Glu Phe Leu Val Phe Ile Phe Leu Tyr Tyr Ser Ile Arg Gly
         35                  40                  45

Leu Tyr Arg Met Val Leu Ser Ser Asp Gln Gln Leu Leu Phe Glu Lys
 50                  55                  60

Leu Ala Leu Tyr Cys Asp Ser Tyr Ile Gln Leu Ile Pro Ile Ser Phe
 65                  70                  75                  80

Val Leu Gly Phe Tyr Val Thr Leu Val Val Ser Arg Trp Trp Ser Gln
                 85                  90                  95

Tyr Glu Asn Leu Pro Trp Pro Asp Arg Leu Met Ile Gln Val Ser Ser
            100                 105                 110

Phe Val Glu Gly Lys Asp Glu Glu Gly Arg Leu Leu Arg Arg Thr Leu
        115                 120                 125

Ile Arg Tyr Ala Ile Leu Gly Gln Val Leu Ile Leu Arg Ser Ile Ser
    130                 135                 140

Thr Ser Val Tyr Lys Arg Phe Pro Thr Leu His His Leu Val Leu Ala
145                 150                 155                 160

Gly Phe Met Thr His Gly Glu His Lys Gln Leu Gln Lys Leu Gly Leu
                165                 170                 175

Pro His Asn Thr Phe Trp Val Pro Trp Val Trp Phe Ala Asn Leu Ser
```

```
                    180             185             190
Met Lys Ala Tyr Leu Gly Gly Arg Ile Arg Asp Thr Val Leu Leu Gln
            195             200             205

Ser Leu Met Asn Glu Val Cys Thr Leu Arg Thr Gln Cys Gly Gln Leu
    210             215             220

Tyr Ala Tyr Asp Trp Ile Ser Ile Pro Leu Val Tyr Thr Gln Val Val
225             230             235             240

Thr Val Ala Val Tyr Ser Phe Phe Leu Ala Cys Leu Ile Gly Arg Gln
                245             250             255

Phe Leu Asn Pro Asn Lys Asp Tyr Pro Gly His Glu Met Asp Leu Val
            260             265             270

Val Pro Val Phe Thr Ile Leu Gln Phe Leu Phe Tyr Met Gly Trp Leu
            275             280             285

Lys Val Ala Glu Gln Leu Ile Asn Pro Phe Gly Glu Asp Asp Asp Asp
            290             295             300

Phe Glu Thr Asn Trp Ile Ile Asp Arg Asn Leu Gln Val Ser Leu Leu
305             310             315             320

Ser Val Asp Gly Met His Gln Asn Leu Pro Pro Met Glu Arg Asp Met
                325             330             335

Tyr Trp Asn Glu Ala Ala Pro Gln Pro Pro Tyr Thr Ala Ala Ser Ala
            340             345             350

Arg Ser Arg Arg His Ser Phe Met Gly Ser Thr Phe Asn Ile Ser Leu
            355             360             365

Lys Lys Glu Asp Leu Glu Leu Trp Ser Lys Glu Ala Asp Thr Asp
            370             375             380

Lys Lys Glu Ser Gly Tyr Ser Ser Thr Ile Gly Cys Phe Leu Gly Leu
385             390             395             400

Gln Pro Lys Asn Tyr His Leu Pro Leu Lys Asp Leu Lys Thr Lys Leu
                405             410             415

Leu Cys Ser Lys Asn Pro Leu Leu Glu Gly Gln Cys Lys Asp Ala Asn
                420             425             430

Gln Lys Asn Gln Lys Asp Val Trp Lys Phe Lys Gly Leu Asp Phe Leu
            435             440             445

Lys Cys Val Pro Arg Phe Lys Arg Arg Gly Ser His Cys Gly Pro Gln
            450             455             460

Ala Pro Ser Ser His Pro Thr Glu Gln Ser Ala Pro Ser Ser Ser Asp
465             470             475             480

Thr Gly Asp Gly Pro Ser Thr Asp Tyr Gln Glu Ile Cys His Met Lys
                485             490             495

Lys Lys Thr Val Glu Phe Asn Leu Asn Ile Pro Glu Ser Pro Thr Glu
            500             505             510

His Leu Gln Gln Arg Arg Leu Asp Gln Met Ser Thr Asn Ile Gln Ala
            515             520             525

Leu Met Lys Glu His Ala Glu Ser Tyr Pro Tyr Arg Asp Glu Ala Gly
        530             535             540

Thr Lys Pro Val Leu Tyr Glu
545             550

<210> SEQ ID NO 30
<211> LENGTH: 19
<212> TYPE: DNA
<213> ORGANISM: Homo Sapiens

<400> SEQUENCE: 30
```

```
ctcctgccca ggcttctac                                                    19
```

<210> SEQ ID NO 31
<211> LENGTH: 19
<212> TYPE: DNA
<213> ORGANISM: Homo Sapiens

<400> SEQUENCE: 31

```
cttgctctgc cttgccttc                                                    19
```

<210> SEQ ID NO 32
<211> LENGTH: 30
<212> TYPE: PRT
<213> ORGANISM: Homo Sapiens

<400> SEQUENCE: 32

```
Ile Pro Ile Ser Phe Val Leu Gly Phe Tyr Val Thr Leu Val Val Thr
1               5                   10                  15

Arg Trp Trp Asn Gln Tyr Glu Asn Leu Pro Trp Pro Asp Arg
            20                  25                  30
```

<210> SEQ ID NO 33
<211> LENGTH: 30
<212> TYPE: PRT
<213> ORGANISM: C. elegans

<400> SEQUENCE: 33

```
Ile Pro Leu Thr Phe Met Leu Gly Phe Phe Val Thr Ile Ile Val Gly
1               5                   10                  15

Arg Trp Asn Asp Ile Phe Leu Asn Ile Gly Trp Val Asp Asn
            20                  25                  30
```

<210> SEQ ID NO 34
<211> LENGTH: 30
<212> TYPE: PRT
<213> ORGANISM: C. elegans

<400> SEQUENCE: 34

```
Ile Pro Leu Thr Phe Met Leu Gly Phe Phe Val Thr Ile Ile Val Arg
1               5                   10                  15

Arg Trp Asn Asp Ile Phe Ala Asn Leu Gly Trp Val Glu Asn
            20                  25                  30
```

<210> SEQ ID NO 35
<211> LENGTH: 30
<212> TYPE: PRT
<213> ORGANISM: C. elegans

<400> SEQUENCE: 35

```
Ile Pro Leu Glu Phe Val Leu Gly Phe Phe Val Thr Ile Val Val Asp
1               5                   10                  15

Arg Trp Thr Lys Leu Trp Arg Thr Val Gly Phe Ile Asp Asp
            20                  25                  30
```

<210> SEQ ID NO 36
<211> LENGTH: 30
<212> TYPE: PRT
<213> ORGANISM: C. elegans

<400> SEQUENCE: 36

```
Ile Pro Leu Glu Phe Val Leu Gly Phe Phe Val Thr Thr Val Val Asn
1               5                   10                  15
```

Arg Trp Thr Lys Leu Tyr Gln Thr Ile Gly Phe Ile Asp Asn
            20                  25                  30

<210> SEQ ID NO 37
<211> LENGTH: 30
<212> TYPE: PRT
<213> ORGANISM: C. elegans

<400> SEQUENCE: 37

Val Pro Leu Asp Trp Met Leu Gly Phe Phe Ile Ala Gly Val Leu Arg
1               5                   10                  15

Arg Phe Trp Tyr Leu Tyr Asp Ile Ile Gly Phe Ile Asp Asn
            20                  25                  30

<210> SEQ ID NO 38
<211> LENGTH: 30
<212> TYPE: PRT
<213> ORGANISM: C. elegans

<400> SEQUENCE: 38

Ile Pro Leu Asn Phe Met Leu Gly Phe Phe Val Thr Ala Val Val Asn
1               5                   10                  15

Arg Trp Thr Tyr Leu Tyr Gln Ile Ile Gly Phe Ile Asp Asn
            20                  25                  30

<210> SEQ ID NO 39
<211> LENGTH: 30
<212> TYPE: PRT
<213> ORGANISM: C. elegans

<400> SEQUENCE: 39

Leu Pro Leu Asn Phe Val Leu Gly Phe Phe Cys Asn Ile Ile Ile Arg
1               5                   10                  15

Arg Trp Leu Lys Leu Tyr Thr Ser Leu Gly Asn Ile Asp Asn
            20                  25                  30

<210> SEQ ID NO 40
<211> LENGTH: 30
<212> TYPE: PRT
<213> ORGANISM: C. elegans

<400> SEQUENCE: 40

Ile Pro Ile Asn Phe Met Leu Gly Phe Phe Val Thr Thr Val Ile Asn
1               5                   10                  15

Arg Trp Met Thr Gln Phe Ala Asn Leu Gly Met Ile Asp Asn
            20                  25                  30

<210> SEQ ID NO 41
<211> LENGTH: 30
<212> TYPE: PRT
<213> ORGANISM: C. elegans

<400> SEQUENCE: 41

Ile Pro Leu Thr Phe Leu Leu Gly Phe Phe Val Ser Phe Val Val Ala
1               5                   10                  15

Arg Trp Gly Ser Ile Leu Asn Gly Ile Gly Trp Ile Asp Asp
            20                  25                  30

<210> SEQ ID NO 42
<211> LENGTH: 30
<212> TYPE: PRT
<213> ORGANISM: C. elegans

-continued

```
<400> SEQUENCE: 42

Ile Pro Val Thr Phe Met Leu Gly Phe Tyr Val Ser Ile Val Tyr Asn
1               5                   10                  15

Arg Trp Thr Lys Val Phe Asp Asn Val Gly Trp Ile Asp Thr
            20                  25                  30

<210> SEQ ID NO 43
<211> LENGTH: 30
<212> TYPE: PRT
<213> ORGANISM: C. elegans

<400> SEQUENCE: 43

Leu Pro Leu Thr Phe Met Leu Gly Phe Phe Val Thr Thr Val Phe Glu
1               5                   10                  15

Arg Trp Arg Ser Ala Leu Asn Val Met Pro Phe Ile Glu Ser
            20                  25                  30

<210> SEQ ID NO 44
<211> LENGTH: 30
<212> TYPE: PRT
<213> ORGANISM: C. elegans

<400> SEQUENCE: 44

Ile Pro Leu Thr Phe Leu Leu Gly Phe Tyr Val Ser Asn Val Val Ser
1               5                   10                  15

Arg Trp Trp Arg Gln Phe Glu Thr Leu Arg Trp Pro Glu Asp
            20                  25                  30

<210> SEQ ID NO 45
<211> LENGTH: 30
<212> TYPE: PRT
<213> ORGANISM: C. elegans

<400> SEQUENCE: 45

Ile Pro Leu Thr Phe Leu Leu Gly Phe Tyr Val Ser Asn Val Val Ala
1               5                   10                  15

Arg Trp Trp Arg Gln Phe Glu Thr Leu Tyr Trp Pro Glu Asp
            20                  25                  30

<210> SEQ ID NO 46
<211> LENGTH: 30
<212> TYPE: PRT
<213> ORGANISM: C. elegans

<400> SEQUENCE: 46

Ile Pro Leu Thr Phe Leu Leu Gly Phe Tyr Val Ala Met Ile Val Arg
1               5                   10                  15

Arg Trp Trp Asp Cys Cys Gln Leu Ile Ser Trp Pro Asp His
            20                  25                  30

<210> SEQ ID NO 47
<211> LENGTH: 30
<212> TYPE: PRT
<213> ORGANISM: C. elegans

<400> SEQUENCE: 47

Ile Pro Leu Ser Phe Leu Leu Gly Phe Phe Val Ser Leu Ile Val Ala
1               5                   10                  15

Arg Trp Trp Glu Gln Phe Asn Cys Ile Ser Trp Pro Asp Lys
            20                  25                  30
```

```
-continued

<210> SEQ ID NO 48
<211> LENGTH: 30
<212> TYPE: PRT
<213> ORGANISM: C. elegans

<400> SEQUENCE: 48

Val Pro Met Gln Pro Met Leu Gly Tyr Phe Ile Gly Met Val Gly Glu
1               5                   10                  15

Arg Trp Gly Glu Ser Phe Glu Asn Val Ser Tyr Ile Glu Lys
            20                  25                  30
```

What is claimed is:

1. An isolated DNA comprising a nucleotide sequence encoding a polypeptide having an amino acid sequence selected from the group consisting of SEQ ID NO:3, SEQ ID NO:5, and SEQ ID NO:29.

2. The DNA of claim 1 comprising a nucleotide sequence selected from the group consisting of: SEQ ID NO:1, SEQ ID NO:2, SEQ ID NO:4, SEQ ID NO:28, positions 105–1,859 of SEQ ID NO:2, positions 105–1,409 of SEQ ID NO:4, and positions 11–1,663 of SEQ ID NO:28.

3. An isolated DNA comprising a sequence that is identical to SEQ ID NO:2 except that it contains a different nucleotide at a position selected from the group consisting of positions 120, 121, 122, 357, 358, 359, 381, 382, 383, 783, 784, 785, 999, 1000, and 1001.

4. An expression vector comprising the DNA of claim 1.

5. A recombinant host cell comprising the DNA of claim 1.

* * * * *